US006855716B2

(12) United States Patent
Ohno et al.

(10) Patent No.: US 6,855,716 B2
(45) Date of Patent: Feb. 15, 2005

(54) DIHYDROPYRIMIDINE COMPOUNDS AND COMPOSITIONS CONTAINING THE SAME

(75) Inventors: Seiji Ohno, Kawasaki (JP); Akiko Okajima, Kawasaki (JP); Seiji Niwa, Kawasaki (JP); Morikazu Kito, Kawasaki (JP); Akira Takahara, Kawasaki (JP); Yukitsugu Ono, Kawasaki (JP); Yuki Kajigaya, Kawasaki (JP); Tomoko Takeda, Kawasaki (JP); Hajime Koganei, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/025,589

(22) Filed: Dec. 26, 2001

(65) Prior Publication Data

US 2002/0143023 A1 Oct. 3, 2002

Related U.S. Application Data

(63) Continuation of application No. PCT/JP00/04107, filed on Jun. 22, 2000.

(30) Foreign Application Priority Data

Jun. 23, 1999 (JP) ............................................ 11-177493
Sep. 30, 1999 (JP) ............................................ 11-277717

(51) Int. Cl.[7] .................... A61K 31/505; A61K 31/506; C07D 239/20; C07D 403/04
(52) U.S. Cl. ........................ 514/256; 514/269; 514/274; 514/275; 544/315; 544/316; 544/318; 544/331; 544/332; 544/333; 544/335
(58) Field of Search ............................... 544/315, 316, 544/318, 331, 332, 333, 335; 514/256, 269, 274, 275

(56) References Cited

U.S. PATENT DOCUMENTS

| | | | |
|---|---|---|---|
| 4,675,321 A | | 6/1987 | Baldwin et al. ............. 514/274 |
| 5,767,129 A | | 6/1998 | Yuen ........................... 514/307 |
| 6,172,066 B1 | * | 1/2001 | Nagarathnam et al. ..... 514/252 |
| 6,320,049 B1 | * | 11/2001 | Sidler et al. ................. 544/316 |
| 6,339,696 B1 | * | 1/2002 | Chan et al. .................. 514/274 |
| 6,350,762 B1 | | 2/2002 | Niwa et al. .................. 514/334 |
| 6,350,766 B1 | | 2/2002 | Uneyama et al. ........... 514/356 |
| 6,436,943 B1 | * | 8/2002 | Stoltefuss et al. .......... 514/256 |

FOREIGN PATENT DOCUMENTS

| | | |
|---|---|---|
| EP | 0 237 347 | 9/1987 |
| WO | WO 93/13128 | 7/1993 |
| WO | WO 96/14846 | 5/1996 |
| WO | WO 97/17969 | 5/1997 |
| WO | WO 97/42956 | 11/1997 |
| WO | WO 98/49144 | 5/1998 |
| WO | WO 98/51311 | 11/1998 |
| WO | WO 99/01437 | 1/1999 |
| WO | WO 99/01438 | 1/1999 |
| WO | WO99/32446 | 7/1999 |
| WO | WO 99/32446 | 7/1999 |
| WO | WO 99/54312 | 10/1999 |
| WO | WO 99/54326 | 10/1999 |
| WO | WO 99/54329 | 10/1999 |

OTHER PUBLICATIONS

Oliver P. Kleidernigg, et al., Separation of Enantiomers of 4–Aryldihydropyrimidines by Direct Enantioselective HPLC. A Critical Comparison of Chiral Stationary Phases; Institute of Organic Chemistry, Karl–Franzens–university Graz, Heinrichstrasse 28, A–8010 Graz, Austria; Tetrahedron: Asymmetry, vol. 8, No. 12, pp. 2057–2067, 1997.

Brian Cox, et al.; Monthly Focus: Central & Peripheral Nervous Sytems, N–Type Calcium Channel Blockers in Pain and Stroke; Glaxo Wellcome, Medicinal Sciences & Lead Discovery, Medicines Research Centre, Gunneis Wood Road, Stevenage, Hertfordshire, SG1 2NY, UK; Exp. Opin. Ther. Patents (1998) 8(10): pp. 1237–1250.

Dodd, et al.; Excitotoxic Mechanisms in the Pathogenesis of Dementia; Clinical Research Laboratory, Royal Brisbane Hospital Foundation, Australia; Neurochem Int Sep. 25, 1994 (3): pp. 203–219 (Abstract only).

Atsushi Kuno et al., "Studies on Cerebral Protective Agents. II. Novel 4–Arylpyrimidine Derivatives with Anti–Anoxic and Anti–Lipid Peroxidation Activities," *Chem. Pharm. Bull.* 40(9) 2423–2431 (1992).

Hitetsura Cho, et al., "Dihydropyrimidines: Novel Calcium Antagonists with Potent and Long–Lasting Vasodilative and Antihypertensive Activity," *J. Med. Chem.*, 1989, 32, 2399–2406.

(List continued on next page.)

*Primary Examiner*—Richard L. Raymond
(74) *Attorney, Agent, or Firm*—Oblon, Spivak, McClelland, Maier & Neustadt, P.C.

(57) ABSTRACT

Dihydropyrimidine derivatives of the following formula or analogs thereof have selective N-type calcium channel antagonistic activity, and they are used as therapeutic agents for various diseases participating in the N-type calcium channels.

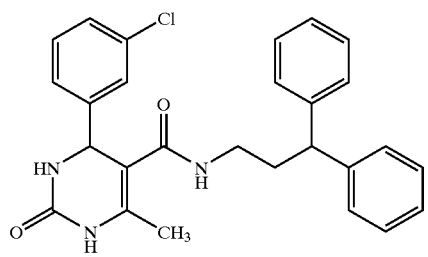

17 Claims, No Drawings

OTHER PUBLICATIONS

YS Sadanandam et al., "Synthesis and Biological Evaluation of New 3,4–dihydro–6–methyl–5–N–methyl–carboamoyl–4–(substituted phenyl)–2–(1H)pyrimidinones and Pyrimidinethiones," *Eur J. Med. Chem.*, (1992) 27, 87–92.

Lange, et al.; Dopamine/Glutamate Interactions in Parkinson's Disease; Department of Neuropsychology and Behavioural Neurobiology, University of Freilburg, Germany; Neurosci Biobehav Rev Jul. 1997; 21(4): pp. 393–400 (Abstract only).

Kieburtz, et al.; Excitotoxicity and Dopaminergic Dysfunction in the Acquired Immunodeficiency Syndrome Dementia Complex, Therapeutic Implications; Department of Neurology, University of Rochester Medical Center, NY 14642; Arch Neurol Dec. 1991; 48(12): pp. 1281–1284 (Abstract only).

Imaizumi, et al.; The Role of Voltage–Gated Ca2+ Channels in Anoxic Injury of Spinal Cord White Matter; Department of Neurology, Yale University School of Medicine, New Haven, CT 06516, USA; Brain Res Jan. 30, 1999; 817(1–2): pp. 84–92 (Abstract only).

Madden, et al.; Treatment with Conotoxin, an 'N–Type' Calcium Channel Blocker, in Neuronal Hypoxicischemic Injury; Department of Neurosciences, University of California, San Diego 92161; Brain Res Dec. 24, 1990; 537(1–2): pp. 256–262 (Abstract only).

White, et al.; Effect of Subcutaneous Administration of Calcium Channel Blocker on Nerve Injury–Induced Hyperalgesia; Department of Anaesthesia and Pain Management, Royal North Shore Hospital, St. Leonards, N.S.W., 2065, Austrilia. dmwhite@med.usyd.edu.au; Brain Res Aug. 10, 1998; 801(1–2): pp. 50–58 (Abstract only).

Basilico, et al.; Influence of Omega–Conotoxin on Morphine Analgesia and Withdrawl Syndrome in Rats; Institute of Pharmacology, Faculty of Sciences, University of Milan, Italy; Eur J Pharmacol Jul. 21, 1992: 218(1): pp. 75–81 (Abstract only).

Pierce, et al.; Calcium–Mediated Second Messengers Modulate the Expression of Behavioral Sensitization to Cocaine; Department of Pharmacology and Psychiatry, Boston University School of Medicine, Boston, Massachusetts 02118–2394, USA; J Pharmacol Exp Ther Sep. 1998; 286(3): pp. 1171–1176 (Abstract only).

Monje et al, "A New Conus Peptide Ligand for Ca Channel Subtypes", Neuropharmacology vol. 32, No. 11, pp. 1141–1149 (1993).

Uneyama et al., "Blockade of N–Type $Ca^{2+}$ Current by Cilnidipine (FRC–8653) in Acutely Dissociated Rat Sympathetic Neurones", British Journal of Pharmacology, (1997) 122, 37–42.

* cited by examiner

DIHYDROPYRIMIDINE COMPOUNDS AND COMPOSITIONS CONTAINING THE SAME

This application is a continuation of PCT/JP00/04107, filed Jun. 22, 2000.

BACKGROUND OF THE INVENTION

The present invention relates to new dihydropyrimidine derivatives and the use of the dihydropyrimidine derivatives as medicines. The activation of N-type calcium channel is observed in various diseases, for example, acute stage of ischemic cerebrovascular disorders caused by cerebral infarction or intracerebral bleeding (including subarachnoidal hemorrhage); progressive neurodegenerative diseases such as Alzheimer's disease, AIDS related dementia and Parkinson's disease, dementia due to cerebrovascular disorder and ALS; neuropathy caused by head injury; various pains such as pain caused by spinal injury, diabetes or thromboangiitis obliterans, postoperative pain, migraine and visceral pain; various diseases associated with psychogenic stress such as bronchial asthma, unstable angina and irritable colitis; emotional disorder and withdrawal symptoms after addiction to drugs such as ethanol addiction withdrawal symptoms. The compounds of the present invention can inhibit the activation of the N-type calcium channel. The present invention provides compounds usable as therapeutic agents for these diseases.

DESCRIPTION OF THE BACKGROUND

Calcium channels are now classified into subtypes of L, N, P, Q, R and T. Each subtype of calcium channels is organ-specifically distributed. It is known that particularly N-type calcium channel is widely distributed in pars centralis, peripheral nerves and adrenomedullary cells and participates in neuronal cell death, regulation of blood catecholamine level and control of senses such as perception.

It has been confirmed that omega conotoxin GVIA and omega conotoxin MVIIA, which are peptides selectively inhibiting N-type calcium channel, inhibit the release of excitatory neurotransmitters in the sliced brain preparation. It is also confirmed in animal experiments that they inhibit the progress of neuronal necrosis associated with cerebrovascular disorders. It is generally considered that compounds having a N-type calcium channel blocking action are clinically effective in the treatment of acute stage of ischemic cerebrovascular disorders caused by cerebral infarction or intracerebral bleeding (including subarachnoidal hemorrhage); progressive neurodegenerative diseases such as Alzheimer's disease, AIDS related dementia and Parkinson's disease, dementia due to cerebrovascular disorder and ALS; and neuropathy caused by head injury. Further, it is confirmed in animal tests that omega conotoxin MVIIA relieves a pain induced by formaldehyde, hot plate and peripheral neuropathy. Accordingly, omega conotoxin MVIIA is considered to be clinically effective against various pains such as pain caused by spinal injury, diabetes or thromboangiitis obliterans, postoperative pain, migraine and visceral pain. In addition, because omega conotoxin GVIA inhibits the release of catecholamine from cultured sympathetic ganglion cells, catecholamine secretion from canine adrenal medulla and the contraction of the isolated blood vessel by electric stimulation of the perivascular nerve, it is considered that compounds having N-type calcium channel-blocking effects are clinically effective against various diseases related to psychogenic stress such as bronchial asthma, unstable angina and irritable colitis [Neuropharmacol., 32, 1141 (1993)].

Some peptidergic and non-peptidergic compounds which selectively affect N-type calcium channels have been ever disclosed (see, for example, WO 9313128, WO 9849144, WO9901437, WO9901438 and WO9932446). However, none of them was actually used as a medicine. Some of the compounds which affect N-type calcium channels are also effective against various types of calcium channels of other than N-type [British Journal of Pharmacology, 122 (1) 37–42, 1997]. For example, compounds having an antagonistic effect on L-type calcium channels which are very closely related to hypotensive effect, could not be used for diseases for which N-type calcium channel antagonists will be used (such as cerebral stroke, neuralgia, terminal cancer pain and pain of spinal injury). Under these circumstances, the development of a highly active antagonist selective toward N-type calcium channel has been eagerly demanded. Recently, improvement in QOL (Quality of life) of the patients is demanded, and medicines to be taken orally are considered to be necessary. However, N-type calcium channel antagonists well-known in the art were yet unsatisfactory for solving this problem because some of them are peptides which cannot be absorbed in the digestive organs or some of them are chemically unstable and, therefore, decomposed in the digestive organs.

DISCLOSURE OF THE INVENTION

SUMMARY OF THE INVENTION

The object of the present invention is to provide new compounds having a selective antagonistic effect on N-type calcium channels.

Another object of the present invention is to provide antagonists to N-type calcium channels.

Still another object of the present invention is to provide chemically stable, oral antagonists to N-type calcium channels.

A further object of the present invention is to provide a therapeutic agent for any of acute stage of ischemic cerebrovascular disorders caused by cerebral infarction or intracerebral bleeding, Alzheimer's disease, AIDS related dementia, Parkinson's disease, progressive neurodegenerative diseases, neuropathy caused by head injury, pain caused by thromboangiitis obliterans, postoperative pain, migraine, visceral pain, bronchial asthma, unstable angina, irritable colitis and withdrawal symptoms after addiction to drugs.

A further object of the present invention is to provide a pharmaceutical composition.

DETAILED DESCRIPTION OF THE PREFERRED EMBODIMENTS

After synthesizing various dihydropyrimidine derivatives and examining the N-type calcium channel inhibiting effect (determined by fluorescent dye method) and L-type calcium channel inhibiting effect (determined by the relaxation after KCl contraction of samples of thoracic aorta extracted from rats) of them for the purpose of solving the above-described problems, the inventors have found that specified, new dihydropyrimidine derivatives have an excellent effect of selectively antagonizing N-type calcium channels. After examining the physicochemical properties of those compounds, the inventors have found that the stability of them is improved particularly in an acidic solution. The present invention has been completed on the basis of this finding.

Namely, the present invention provides dihydropyrimidine derivatives of the following general formula (1), tautomers thereof and pharmaceutically acceptable salts thereof.

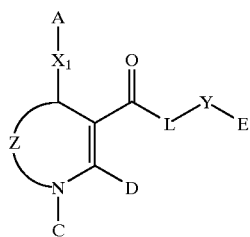

(1)

wherein Z represents a group of the following general formula (Z1) or (Z2), which is bonded to the nitrogen atom at a symbol "*".

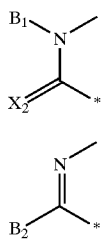

(Z1)

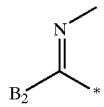

(Z2)

wherein $B_1$ represents hydrogen atom, a lower alkyl group which may contain a hetero atom in the chain thereof, a lower alkylcarbonyl group, an aryl-lower alkyl group, a heteroaryl-lower alkyl group, a hydroxy-lower alkyl group, a halogeno-lower alkyl group, an amino-lower alkyl group, a carboxy-lower alkyl group, a lower alkyloxycarbonyl-lower alkyl group or a group of the following general formula (3) or (4):

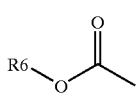

(3)

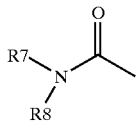

(4)

wherein $R^6$ to $R^8$ each represent hydrogen atom, a linear, branched or cyclic, saturated or unsaturated hydrocarbon group having 1 to 6 carbon atoms, an alkyl group substituted with a cyclic alkyl group which may contain a hetero atom, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an amino-lower alkyl group, an amino-lower alkenyl group, a carboxy-lower alkyl group, a carboxy-lower alkenyl group, an aryl-lower alkyl group, an aryl-lower alkenyl group, a diaryl-lower alkyl group, a heteroaryl-lower alkyl group, a heteroaryl-lower alkenyl group, a cyano-lower alkyl group or a cyano-lower alkenyl group, and the chains of $R^6$ to $R^8$ may contain a hetero atom, or $R^7$ and $R^8$ may together form a ring which may contain a hetero atom, $B_2$ represents an amino group, a lower alkyl group which may contain a hetero atom in the chain thereof, a lower alkylamino group, a lower alkylthio group, an aryl-lower alkyl group, a heteroaryl-lower alkyl group, a hydroxy-lower alkyl group, a halogeno-lower alkyl group, a substituted or unsubstituted aryl group or a substituted or unsubstituted heteroaryl group, $X_2$ represents oxygen atom or sulfur atom, A represents a group of the following general formula (2), or 1-naphthyl, 2-naphthyl, indole-2-yl, indole-3-yl, thiophene-3-yl, thiophene-2-yl, furan-3-yl, furan-2-yl, pyridine-4-yl, pyridine-3-yl or pyridine-2-yl group:

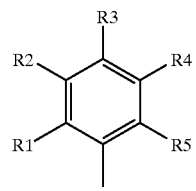

(2)

wherein $R^1$, $R^2$, $R^3$, $R^4$ and $R^5$ may be the same or different from each other and each represent hydrogen atom, a halogen atom, hydroxyl group, carboxyl group, amino group, cyano group, nitro group, a lower alkyl group, a lower alkoxyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, an amino-lower alkyl group, an amino-lower alkoxyl group, an amino-lower alkenyl group, a carboxy-lower alkyl group, a carboxy-lower alkoxyl group, a carboxy-lower alkenyl group, an aryl-lower alkoxyl group or an aroyl group, C represents hydrogen atom, a lower alkyl group, a hydroxy-lower alkyl group, an aryl-lower alkyl group, a heteroaryl-lower alkyl group, an amino-lower alkyl group or a carboxy-lower alkyl group, D represents hydrogen atom, a lower alkyl group, dimethoxymethyl group, cyano group, an aryl-lower alkyl group, a heteroaryl-lower alkyl group, a hydroxy-lower alkyl group, a halogeno-lower alkyl group, an amino-lower alkyl group, a carboxy-lower alkyl group or a group of the following general formula (5) or (6):

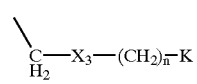

(5)

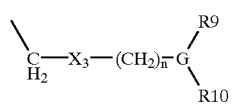

(6)

wherein $X_3$ represents O, S or N—$R_8$, n represents an integer of 0 to 6, K in general formula (5) represents hydrogen atom, a halogen atom, hydroxyl group, carboxyl group, amino group, cyano group, nitro group, azido group, a substituted or unsubstituted aryl group or a substituted or unsubstituted heteroaryl group, G in the general formula (6) represents N or C—H, wherein $R^8$ to $R^{10}$ may be the same or different from each other, and they each represent hydrogen atom, a linear, branched or cyclic, saturated or unsaturated hydrocarbon group having 1 to 6 carbon atoms, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an amino-lower alkyl group, an amino-lower alkenyl group, a carboxy-lower alkyl group, a carboxy-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains may contain a hetero atom, or $R^9$ and $R^{10}$ may together form a ring which may contain a hetero atom, E represents hydrogen atom, a group of the following general formula (7), a substituted or unsubstituted heteroaryl group, cyclopentyl group, cyclohexyl group, morpholine-1-yl group, pyrrolidine-1-yl group, pyrrolidinone-1-yl group, piperidine-1-yl group, piperidinone-1-yl group, piperazine-1-yl group, homopiperidine-1-yl group or homopiprazine-1-yl group:

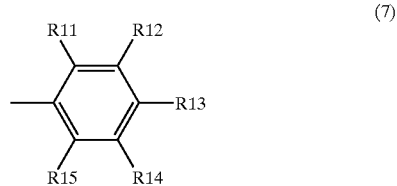

(7)

wherein $R^{11}$, $R^{12}$, $R^{13}$, $R^{14}$ and $R^{15}$ may be the same or different from each other and each represent hydrogen atom, a halogen atom, hydroxyl group, carboxyl group, amino group, cyano group, nitro group, a lower alkyl group, a lower alkoxyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, an amino-lower alkyl group, an amino-lower alkoxyl group, an amino-lower alkenyl group, a carboxy-lower alkyl group, a carboxy-lower alkoxyl group, a carboxy-lower alkenyl group, an aryl-lower alkyl group, an aryl-lower alkoxyl group, a lower alkoxycarbonyl group, an aroyl group, a substituted or unsubstituted aryl group, a substituted or unsubstituted heteroaryl group or a saturated cyclic hydrocarbon having 3 to 8 carbon atoms, which may contain a hetero atom in the chain thereof and/or the ring thereof, $X_1$ represents an interatomic bond, —$CH_2$—, —$CH_2CH_2$—, —CH=CH— or —C≡C—, L represents >N—F or oxygen atom wherein F represents hydrogen atom, a lower alkyl group which may contain a hetero atom in the chain thereof, a hydroxy-lower alkyl group, an amino-lower alkyl group, a carboxy-lower alkyl group or a lower alkyloxycarbonyl-lower alkyl group, Y represents an interatomic bond, a saturated or unsaturated linear hydrocarbon group having 1 to 6 carbon atoms, which may contain a hetero atom in the group thereof, or a group of the following general formula (8):

(8)

wherein $R_{16}$ represents hydrogen atom, a substituted or unsubstituted, saturated or unsaturated linear, branched or cyclic hydrocarbon group having 1 to 6 carbon atoms, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an amino-lower alkyl group, an amino-lower alkenyl group, a carboxy-lower alkyl group, a carboxy-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains of $R^{16}$ may contain a hetero atom, and m represents an integer of 0 to 5.

The present invention provides an N-type calcium channel antagonist containing the above-described dihydropyrimidine derivative, a tautomer thereof or a pharmaceutically acceptable salt thereof as the active ingredient.

The present invention also provides a therapeutic agent containing the above-described dihydropyrimidine derivative, a tautomer thereof or a pharmaceutically acceptable salt thereof as the active ingredient, for any of acute stage of ischemic cerebrovascular disorders caused by cerebral infarction or intracerebral bleeding, Alzheimer's disease, AIDS related dementia, Parkinson's disease, progressive neurodegenerative diseases, dementia due to cerebrovascular disorder, pain caused by thromboangiitis obliterans, postoperative pain, migraine, visceral pain, bronchial asthma, unstable angina, irritable colitis and withdrawal symptoms after addiction to drugs.

The present invention further provides a pharmaceutical composition containing the dihydropyrimidine derivative represented by the above general formula (1), a tautomer thereof or a pharmaceutically acceptable salt thereof, a carrier and/or a diluent.

BEST MODE FOR CARRYING OUT THE INVENTION

The term "lower" herein indicates that the group has 1 to 6 carbon atoms. Alkyl groups themselves and also alkyl groups in alkenyl groups, alkynyl groups, alkoxyl groups, alkylamino groups, alkylthio groups and alkanoyl groups may be either linear or branched. Examples of these alkyl groups are methyl group, ethyl group, propyl group, isopropyl group, butyl group, secondary and tertiary butyl groups, pentyl group and hexyl group. Among them, those having 1 to 3 carbon atoms are preferred. The aryl-lower alkyl groups include, for example, benzyl group. The heteroaryl-lower alkyl groups include, for example, pyridylmethyl group. The aryl-lower alkoxyl groups include, for example, benzyloxy group. The hetero atoms include nitrogen, oxygen, sulfur, etc. The halogen atoms include fluorine, chlorine, bromine and iodine atoms. In the present specification, the aryl groups are both substituted and unsubstituted aryl groups. They are preferably phenyl group and substituted phenyl group, and the substituents are particularly preferably halogens, alkyl groups and alkoxyl groups. The heteroaryl groups are substituted or unsubstituted heteroaryl groups such as, preferably, pyridyl group, furyl group and thienyl group, and also substituted pyridyl, furyl and thienyl groups. Halogens, alkyl groups and alkoxyl groups are particularly preferred as the substituents. The aroyl groups include, for example, benzoyl group and pyridylcarbonyl group. The hydrocarbon groups indicate alkyl groups, alkenyl groups and alkynyl groups. The saturated hydrocarbon groups indicate alkyl groups such as methyl group, ethyl group, propyl group, isopropyl group, butyl group, pentyl group, hexyl group and sec. and tert. butyl groups. The unsaturated hydrocarbon groups indicate alkenyl groups and alkynyl groups. The alkenyl groups include propenyl group, butenyl group, pentenyl group, etc. The alkynyl groups include ethynyl group, propinyl group, butynyl group, etc. Examples of the cyclic hydrocarbon groups include cyclopentyl group and cyclohexyl group. Examples of the cyclic hydrocarbon groups which may contain a hetero atom in the chain thereof include piperidyl group, pyrrolidinyl group and piperadinyl group. The hydrocarbon groups and alkyl groups which may contain a hetero atom in the chain or group thereof include alkoxyl groups, alkylamino groups, alkylthio groups, alkoxymethyl groups and alkylaminoethyl groups.

The groups represented by $R^6$ to $R^8$ in the groups of general formula (3) or (4) in the group represented by $B_1$ in the general formula (1) each represent hydrogen atom, a linear, branched or cyclic, saturated or unsaturated hydrocarbon group having 1 to 6 carbon atoms, an alkyl group substituted with a cyclic alkyl group which may contain a hetero atom, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an amino-lower alkyl group, an amino-lower alkenyl group, a carboxy-lower alkyl group, a carboxy-lower alkenyl group, an aryl-lower alkyl group, an aryl-lower alkenyl group, a diaryl-lower alkyl group, a heteroaryl-lower alkyl group, a heteroaryl-lower alkenyl group, a cyano-lower alkyl group or a cyano-lower alkenyl group, and the chains of $R^6$ to $R^8$ may contain a hetero atom, or $R^7$ and $R^8$ may together form a ring which may contain a hetero atom. The linear, branched or cyclic, saturated or unsaturated hydrocarbons having 1 to 6 carbon atoms herein include methyl group, ethyl group, propyl group, isopropyl group, cyclopentyl group, cyclohexyl group, allyl group and vinyl group. The substituents in the substituted or unsubstituted aryl groups or substituted or unsubstituted heteroaryl groups in the groups represented by $R^6$ to $R^8$ include those described above with reference to $R^1$ to $R^5$ in general formula (2).

The amino-lower alkyl groups include, for example, 3-aminopropyl group, and the carboxy-lower alkyl groups include, for example carboxymethyl group.

The aryl-lower alkyl groups, aryl-lower alkenyl groups, diaryl-lower alkyl groups, heteroaryl-lower alkyl groups and heteroaryl-lower alkenyl groups include, for example, 3-phenylpropyl group, 3-phenyl-2-propene-1-yl group, 3,3-diphenylpropyl group, 3-(pyridine-2-yl)propyl group and 3-(pyridine-2-yl)-2-propene-1-yl group, respectively.

$R^7$ and $R^8$ may together form a ring which may contain a hetero atom. The rings are 3- to 8-membered rings such as piperidine-1-yl group, piperidine-4-yl group, pyrrolidine-1-yl group, pyrrolidine-3-yl group, piperidinone-1-yl group, pyrrolidinone-1-yl group, piperazine-1-yl group and morpholine-4-yl group.

$B_1$ is preferably hydrogen atom, a group of the general formula (3) or a group of general formula (4). In them, hydrogen atom is particularly preferred. The groups represented by $R^6$ to $R^8$ in the groups of general formulae (3) and (4) are each preferably hydrogen atom, a linear, saturated hydrocarbon group having 1 to 6 carbon atoms (particularly an alkyl group), an aryl-lower alkyl group wherein the aryl group may be substituted and the lower alkyl group may contain a hetero atom, an aryl-lower alkenyl group, a diaryl-lower alkyl group or a heteroaryl-lower alkyl group. When $B_1$ is a lower alkyloxycarbonyl-lower alkyl group, preferably, L is oxygen atom, Y is an interatomic bond and E is hydrogen atom. When $R^6$ to $R^8$ are each a linear, branched or cyclic, saturated or unsaturated hydrocarbon group having 1 to 6 carbon atoms, a substituted or unsubstituted aryl group, a hydroxy-lower alkyl group, a hydroxy-lower alkenyl group, a halogeno-lower alkyl group, a halogeno-lower alkenyl group, a carboxy-lower alkyl group, a carboxy-lower alkenyl group, a substituted or unsubstituted aryl-lower alkyl group, a substituted or unsubstituted aryl-lower alkenyl group, a substituted or unsubstituted heteroaryl-lower alkyl group or a substituted or unsubstituted heteroaryl-lower alkenyl group, it is preferred that L is oxygen atom, Y is an interatomic bond and E is hydrogen atom.

The substituents in the substituted or unsubstituted aryl group or substituted or unsubstituted heteroaryl group represented by $B_2$ in general formula (1) are, for example, halogen atoms (such as fluorine, chlorine, bromine and iodine atoms), hydroxyl group, carboxyl group, amino group, cyano group, nitro groups, lower alkyl groups, lower alkoxyl groups, halogeno-lower alkyl groups, hydroxy-lower alkyl groups and lower-alkoxycarbonyl groups.

The lower alkylamino groups and lower alkylthio groups represented by $B_2$ are, for example, methylamino group, dimethylamino group, diethylamino group and methylthio group.

The groups represented by $B_2$ are preferably phenyl group, aryl groups, heteroaryl groups, lower alkyl groups, amino group, lower alkylamino groups, lower alkylthio groups and lower alkyl groups. They are more preferably phenyl group, pyridyl group, methylthio group, amino group and methyl group. Phenyl group is the most preferred.

As the groups represented by $X_2$, oxygen is preferred.

1-Naphthyl group, 2-naphthyl group, indole-2-yl group and indole-3-yl group represented by A in above general formulae (1) are either unsubstituted or substituted. The substituents are those listed above for $R^1$ to $R^5$ in general formula (2).

Thiophene-3-yl group, thiophene-2-yl group, furan-3-yl group, furan-2-yl group, pyridine-4-yl group, pyridine-3-yl group and pyridine-2-yl group represented by A are also either unsubstituted or substituted. When two or more substituents are contained therein, they may form a ring together. The substituents are those described above with reference to 1-naphthyl group or the like. The rings formed by those groups include benzothiophene, benzofuran, quinoline, isoquinoline, etc.

A is preferably a group represented by general formula (2). In these groups, those wherein one or two of $R^1$ to $R^5$ represent a halogen atom, particularly chlorine atom, are preferred. When two of $R^1$ to $R^5$ represent a halogen atom, preferably, one of them is $R^4$ and the other is $R^3$. More preferably, one of $R^1$ to $R^5$ is a halogen atom, particularly chlorine atom. Most preferably, $R^4$ represents chlorine atom, and the rest is each hydrogen atom.

In above general formula (1), C is preferably hydrogen atom.

K represented by general formula (5) in the groups represented by D in above general formula (1) represents hydrogen atom, a halogen atom, hydroxyl group, carboxyl group, amino group, cyano group, nitro group, azido group, a substituted or unsubstituted aryl group or a substituted or unsubstituted heteroaryl group. K is preferably hydrogen atom, hydroxyl group, carboxyl group or amino group. The substituents in the substituted or unsubstituted aryl groups or substituted or unsubstituted heteroaryl groups represented by K are those described above with reference to $R^1$ to $R^5$ in general formula (2).

The groups represented by $R^9$ or $R^{10}$ in the groups represented by general formula (6) in the groups represented by D in above general formula (1) each represent hydrogen atom, a linear, branched or cyclic, saturated or unsaturated hydrocarbon group having 1 to 6 carbon atoms, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an amino-lower alkyl group, an aryl-lower alkyl group, a carboxy-lower alkyl group, a carboxy-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains may contain a hetero atom, or $R^9$ and $R^{10}$ may together form a ring which may contain a hetero atom. The linear, branched or cyclic, saturated or unsaturated hydrocarbon group having 1 to 6 carbon atoms herein include, for example, methyl group, ethyl group, propyl group, isopropyl group, cyclopentyl group, cyclohexyl group, allyl group and vinyl group. Methyl group and ethyl group are preferred. The substituents in the substituted or unsubstituted aryl groups or substituted or unsubstituted heteroaryl groups represented by $R^9$ or $R^{10}$ are those described above with reference to $R^1$ to $R^5$ in general formula (2).

$R^9$ and $R^{10}$ may be bonded together to form a ring with G. The ring may contain a hetero atom. The rings herein are 3- to 8-membered rings such as cyclopentyl group, cyclohexyl group, piperidine-1-yl group, piperidine-4-yl group, pyrrolidine-1-yl group, pyrrolidine-3-yl group, piperidinone-1-yl group pyrrolidinone-1-yl group, piperazine-1-yl group and morpholine-4-yl group.

Group D in general formula (1) is preferably a lower alkyl group, methoxymethyl group, 2-aminoethoxymethyl group, 2-hydroxyethoxymethyl group, 2-carboxyethoxymethyl group, a group of general formula (5) or a group of general formula (6). Group D is more preferably a lower alkyl group, a group of general formula (5) or a group of general formula (6). Group D is particularly preferably methyl group, a group of general formula (5) wherein $X_3$ represents oxygen atom, n represents an integer of 2 or 3 and K represents a halogen atom (particularly chlorine atom), such as 2-chloroethoxymethyl group, or a group of general formula (6) wherein $X_3$ represents oxygen atom, n represents an integer of 0 to 3 (particularly 2 or 3) and $R^9$ and $R^{10}$ are bonded together to form a 5- to 7-membered ring with G (G is preferably N or C—H), such as 2-cyclohexylethoxymethyl group or 2-piperidinoethoxymethyl group.

E is preferably hydrogen atom, a group of general formula (7), or a substituted or unsubstituted heteroaryl group. E is more preferably a group of general formula (7) or thiophene-3-yl group, thiophene-2-yl group, furan-3-yl group, furan-2-yl group, pyridine-4-yl group, pyridine-3-yl group, pyridine-2-yl group or imidazole-1-yl group. E is particularly preferably a group of general formula (7). When E is hydrogen, it is preferred that L is oxygen atom and Y is an interatomic bond.

$X_1$ is preferably an interatomic bond.

L is preferably >N—F. When L is oxygen atom, Z is preferably $Z_1$.

F is preferably hydrogen atom.

Y is preferably a group of general formula (8) wherein m represents an integer of 1 to 4 (particularly 1 to 3) and $R_{16}$ represents an aryl group (particularly preferably phenyl group), a heteroaryl group, a substituted or unsubstituted cyclic alkyl group (containing or not containing a hetero atom) having 1 to 6 carbon atoms or a substituted or unsubstituted hydrocarbon group having 3 or 4 carbon atoms. Y is preferably a group of general formula (8) wherein $R^{16}$ represents an aryl group, or Y is preferably a group of general formula (8) wherein $R^{16}$ represents a saturated or unsaturated hydrocarbon group having 3 or 4 carbon atoms. Y is most preferably 3,3-diphenylpropyl group, 3-phenylpropyl group or 3-phenyl-2-propene-1-yl group. When Y is an interatomic bond, preferably L is oxygen atom and E is hydrogen atom.

In the present invention, it is preferred that in general formula (1), Z is $Z_1$ and L is >N—F.

When Z is $Z_1$ and L is >N—F in general formula (1), preferably A is a group of general formula (2), $B_1$ is hydrogen atom and $X_1$ is an interatomic bond.

When Z is $Z_1$ and L is >N—F in general formula (1), preferably A is a group of general formula (2), $B_1$ is hydrogen atom, $X_1$ is an interatomic bond and E is a group of general formula (7) or thiophene-3-yl group, thiophene-2-yl group, furan-3-yl group, furan-2-yl group, pyridine-4-yl group, pyridine-3-yl group, pyridine-2-yl group or imidazole-1-yl group.

When Z is $Z_1$ and L is >N—F in general formula (1), preferably A is a group of general formula (2), $B_1$, C and F are each hydrogen atom, E is a group of general formula (7) and $X_1$ is an interatomic bond.

When Z is $Z_1$ and L is >N—F in general formula (1), preferably A is a group of general formula (2), $B_1$, C and F are each hydrogen atom, D is a lower alkyl group, E is a group of general formula (7) and $X_1$ is an interatomic bond.

When Z is $Z_1$ and L is >N—F in general formula (1), preferably A is a group of general formula (2), $B_1$, C and F are each hydrogen atom, D is a group of general formula (5), wherein $X_3$ is oxygen atom and n is an integer of 1 to 3, E is a group of general formula (7) and $X_1$ is an interatomic bond.

When Z is $Z_1$ and L is >N—F in general formula (1), preferably A is a group of general formula (2), $B_1$, C and F are each hydrogen atom, D is a group of general formula (6), wherein $X_3$ is oxygen atom and n is an integer of 1 to 3, E is a group of general formula (7) and $X_1$ is an interatomic bond.

When Z is $Z_1$ and L is >N—F in general formula (1), preferably A is a group of general formula (2), $B_1$, C and F are each hydrogen atom, D is a lower alkyl group, E is a group of general formula (7), $X_1$ is an interatomic bond and Y is a group of general formula (8), wherein m represents an integer of 1 to 4 and $R_{16}$ represents a substituted or unsubstituted aryl group, or a saturated or unsaturated hydrocarbon group having 3 or 4 carbon atoms.

In the present invention, it is preferred that in general formula (1), Z is $Z_2$ and L is >N—F.

When Z is $Z_2$ and L is >N—F in general formula (1), preferably A is a group of general formula (2), F is hydrogen atom and $X_1$ is an interatomic bond.

When Z is $Z_2$ and L is >N—F in general formula (1), preferably A is a group of general formula (2), E is a group of general formula (7), F is hydrogen atom and $X_1$ is an interatomic bond.

When Z is $Z_2$ and L is >N—F in general formula (1), preferably A is a group of general formula (2), D is a group of general formula (6), wherein $X_3$ represents oxygen atom and n represents an integer of 2 or 3, E is a group of general formula (7), F is hydrogen atom and $X_1$ is an interatomic bond.

When Z is $Z_2$ and L is >N—F in general formula (1), preferably A is a group of general formula (2), E is a group of general formula (7), F is hydrogen atom, $X_1$ is an interatomic bond and Y is a group of general formula (8), wherein m represents an integer of 1 to 4 and $R_{16}$ represents a substituted or unsubstituted aryl group.

When Z is $Z_2$ and L is >N—F in general formula (1), preferably A is a group of general formula (2), E is a group of general formula (7), F is hydrogen atom, $X_1$ is an interatomic bond and Y is an unsaturated hydrocarbon group containing 3 or 4 carbon atoms.

When Z is $Z_2$ and L is >N—F in general formula (1), preferably A is a group of general formula (2), D is a group of general formula (6), wherein $X_3$ is oxygen atom, n is an integer of 2 or 3 and $R_9$ and $R_{10}$ are bonded together to form a 5- to 7-membered ring with G, E is a group of general formula (7), F is hydrogen atom, $X_1$ is an interatomic bond and Y is a group of general formula (8), wherein m represents an integer of 1 to 4 and $R_{16}$ represents a substituted or unsubstituted aryl group, or an unsaturated hydrocarbon group containing 3 or 4 carbon atoms.

Dihydropyrimidine derivatives of the following general formulae (9) and (10), tautomers thereof and pharmaceutically acceptable salts thereof are preferred.

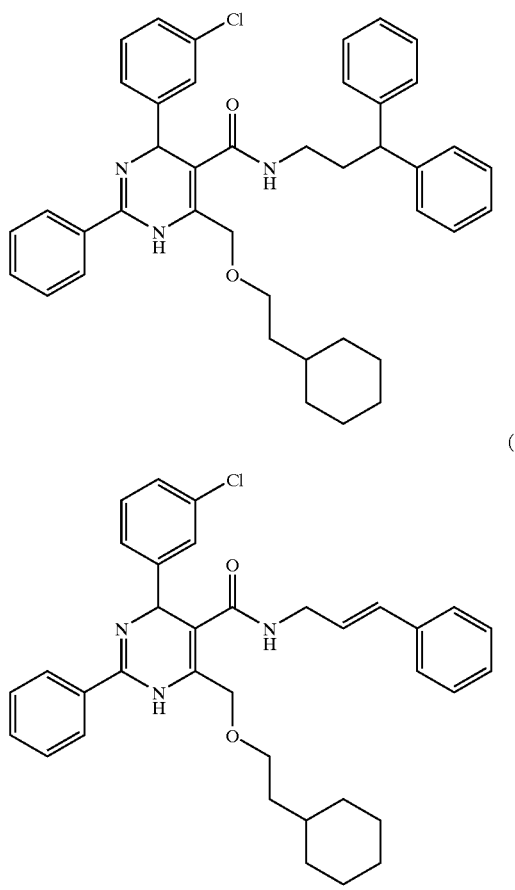

Dihydropyrimidine derivatives (1) of the present invention can be produced by processes described below:

For example, dihydropyrimidine derivatives (1-1) of general formula (1) wherein Z is $Z_1$ and L is >N—F, $B_1$, C and F are each hydrogen atom, D is a group of general formula (5) or (6), wherein $X_3$ is oxygen atom, can be produced as described below.

A benzyl alkoxyacetoacetate (102) can be obtained by reacting an alcohol (101) with a base such as sodium hydride and then reacting the obtained alkoxide with benzyl 4-chloroacetoacetate (100). The benzyl alkoxyacetoacetate (102) thus obtained is subjected to Biginelli reaction (Tetrahedron 49, 6937–6963, 1993) with aldehyde (103) and urea (104) in the presence of an acid catalyst such as hydrochloric acid to synthesize a dihydropyrimidine derivative (105). Then the dihydropyrimidine derivative (105) is subjected to, for example, catalytic reduction to convert it into a carboxylic acid (106), which is condensed with an amine (107) to obtain a 2-oxodihydropyrimidine derivative (1-1).

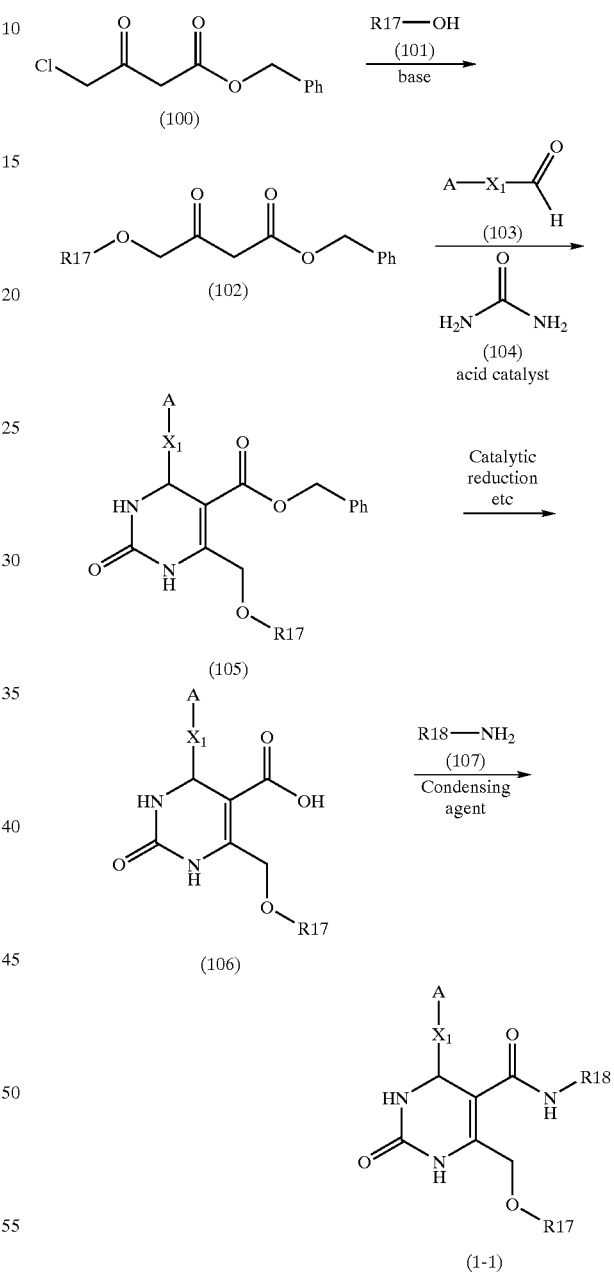

Dihydropyrimidine derivatives (1-2) of general formula (1) wherein Z is $Z_1$, L is oxygen atom, C and F are each hydrogen atom and D is a lower alkyl group (such as methyl group) can be produced as described below.

A β-ketoester (110) is subjected to the dehydration condensation with an aldehyde (103) to obtain an α,β-unsaturated carbonyl compound (111), which is then reacted with an O-methylisourea (112) to obtain a dihydropyrimidine derivative (113).

When O-methylisourea is in the form of a hydrochloride thereof, it is preferably converted into a free amine with a base such as potassium carbonate, sodium acetate or sodium hydrogencarbonate.

The dihydropyrimidine derivative (113) is reacted with nitrophenyl chloroformate in the presence of a base such as sodium hydrogencarbonate, sodium carbonate, triethylamine or sodium hydride to synthesize a carbamate derivative (115). The carbamate derivative (115) thus obtained is reacted with an amine (107) to obtain an urea derivative (116). This urea derivative (116) is reacted with hydrochloric acid or the like to synthesize a 2-oxodihydropyrimidine derivative (117). This 2-oxodihydropyrimidine derivative (117) is catalytically reduced to remove the benzyl ester and also to obtain a 2-oxodihydropyrimidine derivative (1-2).

Dihydropyrimidine derivatives (1-3) of general formula (1) wherein Z is $Z_1$, L is >N—F, C and F are each hydrogen atom and $B_1$ and D are each a lower alkyl group (such as methyl group) can be produced as described below.

A dihydropyrimidine derivative (113) is reacted with, for example, an alkyl halide (120) in the presence of a base such as triethylamine, pyridine or sodium hydride to obtain an N-substituted 3,4-dihydropyrimidine derivative (121). This derivative (121) is reacted with hydrochloric acid or the like to obtain a 2-oxodihydropyrimidine derivative (122), which is converted into a carboxylic acid (123) by the catalytic reduction or the like. The product (123) is condensed with an amine (107) to obtain an 2-oxodihydropyrimidine derivative (1-3).

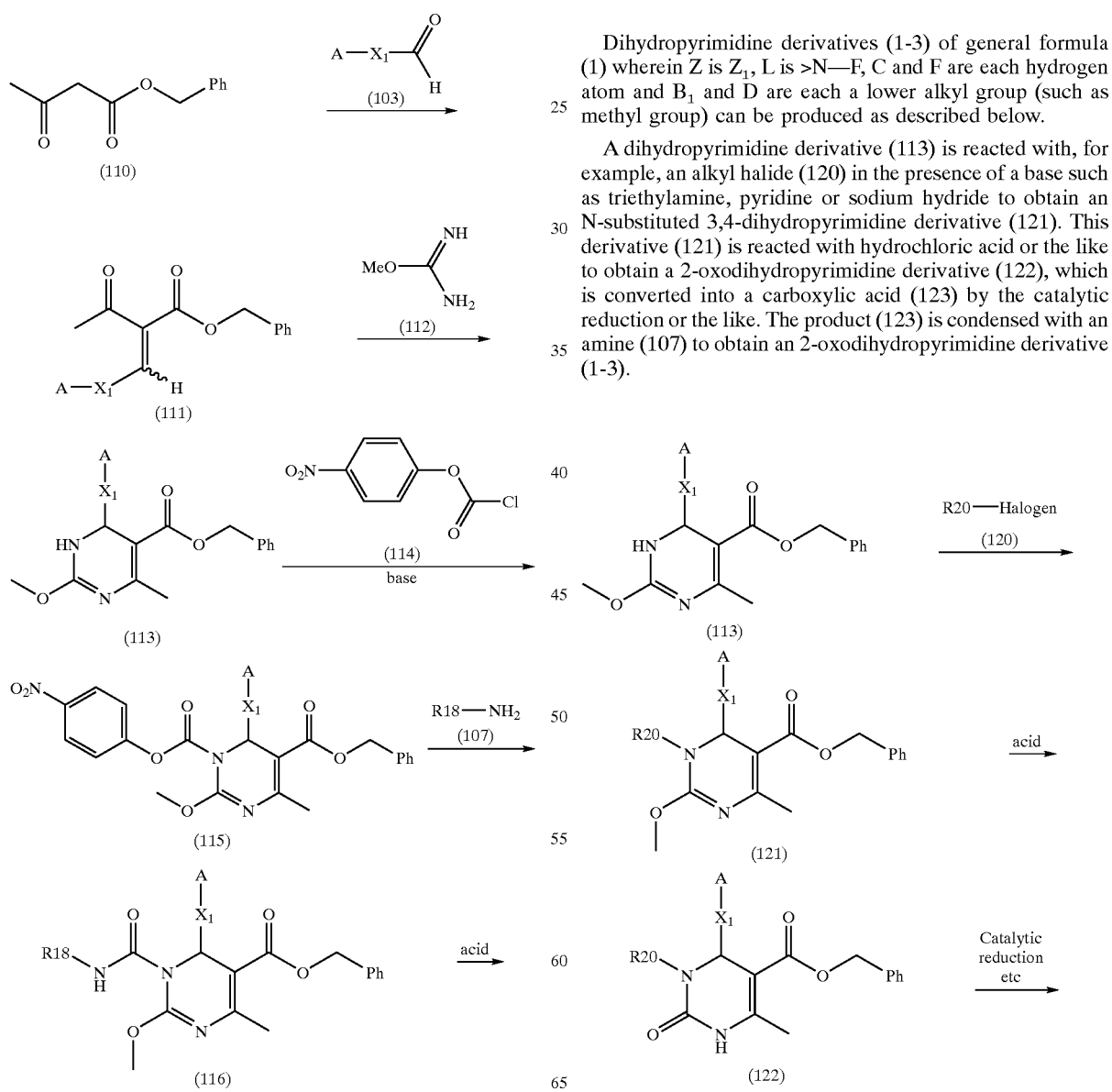

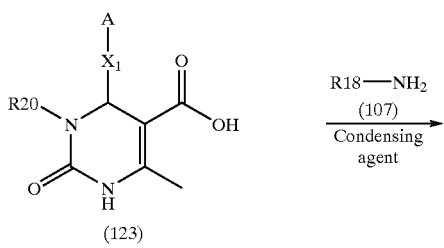

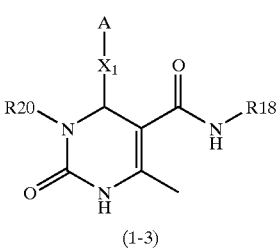

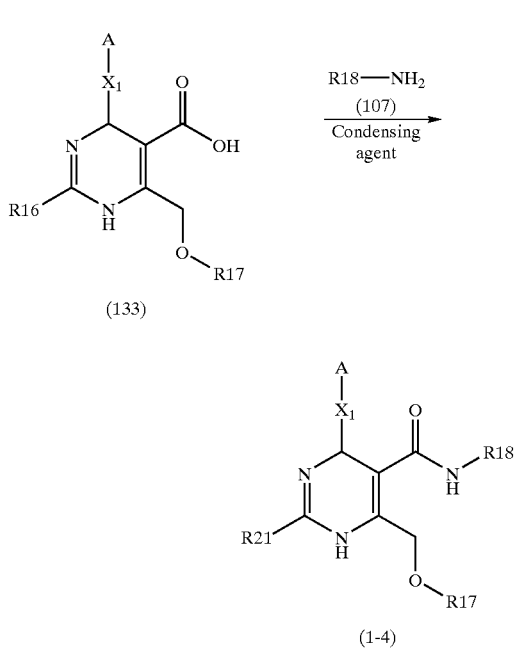

Dihydropyrimidine derivatives (1-4) of general formula (1) wherein Z is $Z_2$, L is >N—F, D is a group of general formula (3), wherein $X_3$ represents oxygen atom, and F is hydrogen atom can be produced by the following reaction scheme:

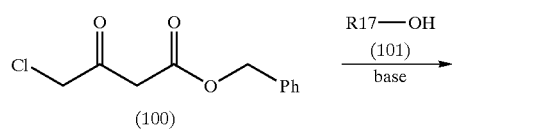

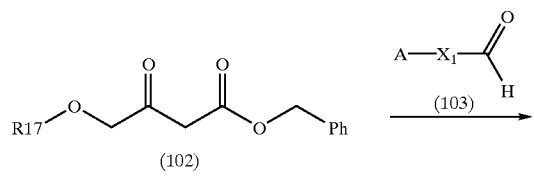

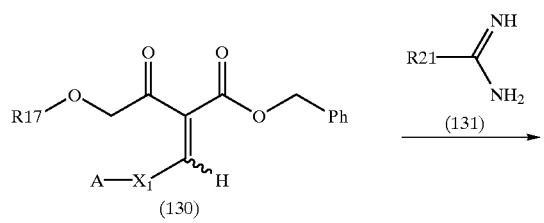

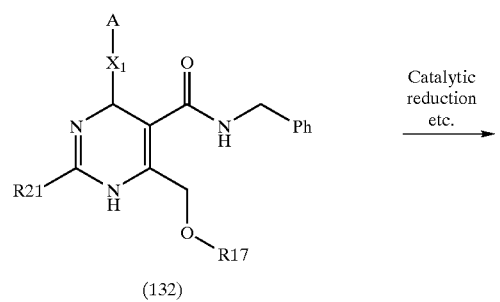

An alkoxide obtained by reacting an alcohol (101) with a base such as sodium hydride is reacted with benzyl 4-chloroacetoaetate (100) to obtain a benzyl alkoxyacetoacetate (102). This ester (102) is subjected to the dehydration condensation with an aldehyde (103) to obtain a compound (130), which is then reacted with an amidine derivative (131) to obtain a dihydropyrimidine derivative (132). When the amidine derivative used is in the form of a salt such as hydrochloride thereof, it is preferably converted into the free amine by reacting it with a base such as potassium carbonate, sodium acetate or sodium hydrogencarbonate. The dihydropyrimidine derivative (132) can be converted into a carboxylic acid (133) by, for example, the catalytic reduction, and the product is condensed with an amine (107) to obtain an amide derivative (1-1).

Benzyl 4-chloroacetoacetate (100) used as the starting material can be obtained by the transesterification of commercially available methyl 4-chloroacetoacetate (134) with benzyl alcohol (135).

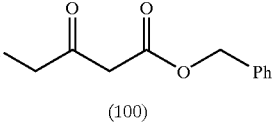

Dihydropyrimidine derivatives (1-5) of general formula (1) wherein Z is $Z_2$, L is >N—F, D is a lower alkyl group, such as methyl group, and F is hydrogen atom can be produced as follows:

An amine (107) is reacted with a diketene (140) in the presence of a base such as triethylamine to obtain a β-ketocarboxylic acid amide (141), which is then subjected to the dehydration condensation with an aldehyde (103) to obtain an α,β-unsaturated carbonyl compound (142), which is then reacted with an amidine derivative to obtain a dihydropyrimidine derivative (1-5).

When the amidine derivative used is in the form of hydrochloride thereof, it is preferably converted into the free amine by using a base such as potassium carbonate, sodium acetate or sodium hydrogencarbonate.

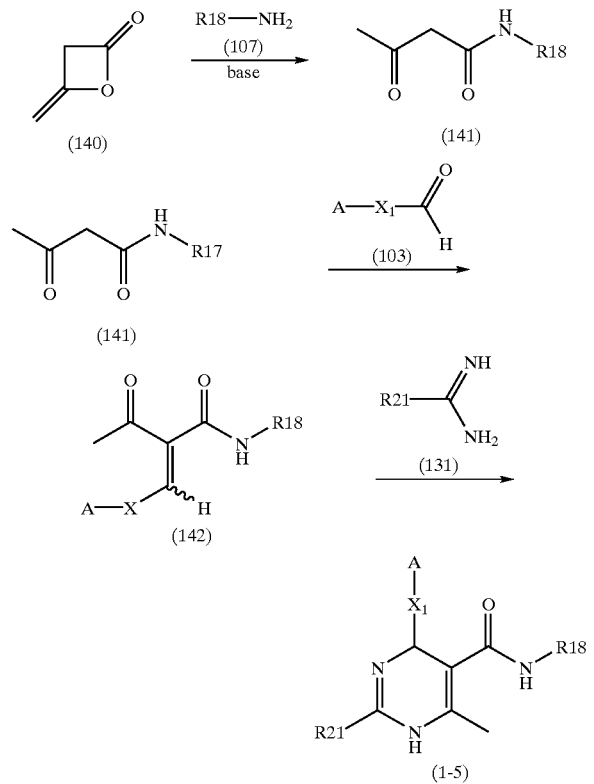

3,4-Dihydropyrimidines of general formula (1a) are considered to be tautomers of 1,4-dihydropyrimidines of general formula (1) in the present invention. The compounds shown as 1,4-dihydropyrimidines in the present invention are considered to be 1,4-dihydropyrimidines, 3,4-dihydropyrimidines and mixtures of them. Optical isomers of 1,4-dihydropyrimidines represented by general formula (1) are possible because they have an asymmetric carbon atom. The compounds of the present invention also include those optical isomers.

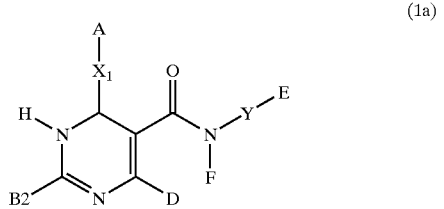

When the compounds of general formula (1) can form salts thereof, the salts are pharmaceutically acceptable ones such as ammonium salts, salts thereof with alkali metals, e.g. sodium and potassium, salts thereof with alkaline earth metals, e.g. calcium and magnesium, salts thereof with aluminum and zinc, salts thereof with organic amines, e.g. morpholine and piperidine, and salts thereof with basic amino acids, e.g. arginine and lysine.

The compounds of general formula (1) and salts thereof are administered as they are or in the form of various medicinal compositions to patients. The dosage forms of the medicinal compositions are, for example, tablets, powders, pills, granules, capsules, suppositories, solutions, sugar-coated tablets and depots. They can be prepared with ordinary preparation assistants by an ordinary method.

For example, the tablets are prepared by mixing the dihydropyrimidine derivative, the active ingredient of the present invention, with any of known adjuvants such as inert diluents, e.g. lactose, calcium carbonate and calcium phosphate; binders, e.g. acacia, corn starch and gelatin; extending agents, e.g. alginic acid, corn starch and pre-gelatinized starch; sweetening agents, e.g. sucrose, lactose and saccharin; corrigents, e.g. peppermint, and cherry; and lubricants, e.g. magnesium stearate, talc and carboxymethyl cellulose.

The N-type calcium channel inhibitor containing one of the compounds of above general formula (1) or one of salts thereof as active ingredient is usable as a therapeutic agent for various diseases, for example, acute stage of ischemic cerebrovascular disorders caused by cerebral infarction or intracerebral bleeding (including subarachnoidal hemorrhage); progressive neurodegenerative diseases such as Alzheimer's disease, AIDS related dementia and Parkinson's disease, dementia due to cerebrovascular disorder and ALS; neuropathy caused by head injury; various pains such as pain caused by spinal injury, diabetes or thromboangiitis obliterans, postoperative pain, migraine and visceral pain; various diseases associated with psychogenic stress such as bronchial asthma, unstable angina and irritable colitis; emotional disorder withdrawal symptoms after addiction to drugs such as ethanol addiction withdrawal symptoms.

The dose of the compound of general formula (1) or salt thereof used for the above-described purpose varies depending on the intended therapeutic effect, administration method, period of the treatment, and age and body weight of the patient. The dose is usually 1 μg to 5 g a day for adults in the oral administration, and 0.01 μg to 1 g a day for adults in the parenteral administration.

The following Examples will further illustrate the present invention, which are only preferred embodiments of the invention and which by no means limit the invention.

EXAMPLE 1

Synthesis of 4-(3-chlorophenyl)-6-[(2-cyclohexylethoxy)methyl]-5-(3,3-diphenylpropylcarbamoyl)-2-phenyl-1,4-dihydropyrimidine 1) Synthesis of benzyl 4-(2-cyclohexylethoxy)acetoacetate:

848 mg (6.62 mmol) of 2-cyclohexane ethanol was dissolved in 10 ml of THF. 530 mg (13.2 mmol) of sodium hydride (60% oily) was added to the obtained solution under cooling with ice, and they were stirred at 40° C. for 1 hour. 1.00 g (4.41 mmol) of benzyl 4-chloroacetoacetate was dissolved in 5 ml of THF, the obtained solution was added dropwise to the reaction mixture for the duration of 1 hour, and they were stirred at room temperature for 2 days. After the extraction with ethyl acetate, the organic layer was washed with 1 N hydrochloric acid and then aqueous sodium hydrogencarbonate solution. The organic layer was dried over anhydrous sodium sulfate and concentrated under reduced pressure. The residue was purified by the silica gel chromatography (hexane/ethyl acetate=10/1) to obtain the title compound.

Yield: 620 mg (1.95 mmol) (44.2%).

MS (ESI, m/z) 317 (M–H)–.

1H-NMR (CDCl3): 0.84–0.96 (3H, m), 1.12–1.26 (3H, m), 1.30–1.54 (2H, m), 1.66–1.70 (5H, m), 3.47 (2H, t), 3.58 (2H, s), 4.06 (2H, s), 5.18 (2H, s), 7.34–7.37 (5H, m).

2) Synthesis of benzyl 3-(3-chlorophenyl)-2-[2-(2-cyclohexylethoxy)acetyl]acrylate (E/Z mixture):

620 mg (1.95 mmol) of benzyl 4-(2-cyclohexylethoxy)acetoacetate, 292 mg (1.95 mmol) of 3-chlorobenzaldehyde and 16.6 mg (0.195 mmol) of piperidine were heated under reflux in the presence of a catalytic amount of p-toluenesulfonic acid in 30 ml of benzene for 6 hours while water was removed. Benzene was evaporated under reduced pressure. Ethyl acetate was added to the reaction mixture. After washing with 1 N hydrochloric acid and then with saturated aqueous sodium hydrogencarbonate solution, the organic layer was dried over anhydrous sodium sulfate and then concentrated under reduced pressure to obtain the unpurified title compound.

Yield: 670 mg (1.52 mmol) (77.9%).

MS (ESI, m/z) 440 (M+).

3) Synthesis of benzyl 4-(3-chlorophenyl)-6-[(2-cyclohexylethoxy)methyl]-2-phenyl-1,4-dihydropyrimidine-5-carboxylate:

119 mg (1.06 mmol) of t-butoxypotassium was dissolved in 5 ml of DMF. 166 mg (1.06 mmol) of benzamidine monohydrochloride was added to the obtained solution under cooling with ice, and they were stirred for 30 minutes. A solution of benzyl 3-(chlorophenyl)-2-[2-(2-cyclohexylethoxy)acetyl]acrylate (E/Z mixture) in 5 ml of DMF was added to the reaction mixture under cooling with ice. The obtained mixture was stirred for 3 hours while the temperature was elevated to room temperature. A catalytic amount of p-toluenesulfonic acid was added to the reaction mixture, and they were heated to 100° C. and stirred overnight. DMF was evaporated under reduced pressure, and the residue was diluted with ethyl acetate and washed with saturated aqueous sodium chloride solution. The organic layer was dried over anhydrous sodium sulfate and then concentrated under reduced pressure. The residue was purified by the silica gel chromatography (hexane/ethyl acetate=10/1) to obtain the title compound.

Yield: 60.0 mg (0.110 mmol) (13.5%)

MS (ESI, m/z) 543 (M+H)+

1H-NMR (CDCl3): 0.85–1.00 (2H, m), 1.12–1.26 (3H, m), 1.35–1.74 (8H, m), 3.60–3.69 (2H, m), 4.79 (2H, dd), 5.12 (2H, dd), 5.85 (1H, s), 7.18–7.34 (10H, m), 7.43–7.48 (4H, m), 7.71–7.74 (2H, m), 8.23 (1H, s).

4) Synthesis of 4-(3-chlorophenyl)-6-[(2-cyclohexylethoxy)methyl]-2-phenyl-1,4-dihydropyrimidine-5-carboxylic acid:

10 ml of ethyl acetate was added to a mixture of 60.0 mg (0.110 mmol) of benzyl 4-(3-chlorophenyl)-6-[(2-cyclohexylethoxy)methyl]-2-phenyl-1,4-dihydropyrimidine-5-carboxylate and a catalytic amount of 10% palladium/carbon, and they were stirred together at room temperature in hydrogen atmosphere under normal pressure for 3 days. The catalyst was filtered out, and the obtained filtrate was concentrated under reduced pressure to obtain the unpurified title compound.

Yield: 60.0 mg (0.132 mmol) (quantitative yield)

1H-NMR (CDCl3): 0.93 (2H, br t), 1.12–1.26 (3H, m), 1.35–1.72 (8H, m), 3.61–3.69 (2H, m), 4.70–4.85 (2H, m), 5.85 (1H, s), 7.14–7.51 (7H, m), 7.72 (2H, d).

5) Synthesis of 4-(3-chlorophenyl)-6-[(2-cyclohexylethoxy)methyl]-5-(3,3-diphenylpropylcarbamoyl)-2-phenyl-1,4-dihydropyrimidine:

60.0 mg (0.110 mmol) of 4-(3-chlorophenyl)-6-[(2-cyclohexylethoxy)methyl]-2-phenyl-1,4-dihydropyrimidine-5-carboxylic acid and 34.9 mg (0.165 mmol) of 3,3-diphenylpropylamine were dissolved in 10 ml of dichloromethane. 31.6 mg (0.165 mmol) of WSC hydrochloride and 16.8 mg (0.110 mmol) of 1-hydroxybenzotriazole (hereinafter referred to as "HOBT") were added to the obtained solution under cooling with ice, and they were stirred at room temperature overnight. The reaction mixture was diluted with dichloromethane and then washed with saturated aqueous sodium hydrogencarbonate solution. The organic layer was dried over anhydrous sodium sulfate and then concentrated under reduced pressure. The residue was purified by the silica gel chromatography (hexane/ethyl acetate=3/1 to 1/1) to obtain the title compound.

Yield: 40 mg (0.0619 mmol) (56.3%).

MS (ESI, m/z) 646 (M+H)+

1H-NMR (CDCl3): 0.86–0.95 (2H, m), 1.10–1.28 (5H, m), 1.53–1.71 (6H, m), 2.12 (2H, br d), 3.15 (2H, br t), 3.50–3.72 (3H, m), 4.85 (1H, br), 5.28 (1H, br), 5.52 (1H, br), 7.09–7.28 (13H, m), 7.39–7.47 (4H, m), 7.69 (2H, br), 8.03 (1H, br).

EXAMPLE 2

Synthesis of 4-(3-chlorophenyl)-6-[(2-cyclohexylethoxy)methyl]-2-phenyl-5-[(3-phenyl-2-propene-1-yl)- carbamoyl]-1,4-dihydropyrimidine 110 mg (0.243 mmol) of 4-(3-chlorophenyl)-6-[(2-cyclohexylethoxy)methyl]-2-phenyl-1,4-dihydropyrimidine-5-carboxylic acid and 38.8 mg (0.292 mmol) of cinnamylamine were dissolved in 10 ml of dichloromethane. 69.9 mg (0.365 mmol) of WSC hydrochloride and 37.2 mg (0.243 mmol) of HOBT were added to the obtained solution under cooling with ice, and they were stirred at room temperature for 3 hours. The reaction mixture was diluted with dichloromethane and then washed with saturated aqueous sodium hydrogencarbonate solution. The organic layer was dried over anhydrous sodium sulfate and then concentrated under reduced pressure. The residue was purified by the silica gel chromatography (hexane/ethyl acetate=10/1 to 1/1) to obtain the title compound.

Yield: 29.1 mg (0.0512 mmol) (21.1%)

MS (ESI, m/z) 568 (M+H)+

1H-NMR (CDCl3): 0.86–0.95 (2H, m), 1.11–1.28 (3H, m), 1.41–1.70 (8H, m), 3.63 (2H, br d), 4.01 (2H, br), 4.89 (2H, br), 5.48 (1H, br), 5.66 (1H, br), 6.09 (1H, br d), 6.29 (1H, br d), 7.20–7.30 (7H, m), 7.36–7.47 (5H, m), 7.70 (2H, br d), 8.08 (1H, br).

EXAMPLE 3

Synthesis of 4-(3-chlorophenyl)-6-methyl-2-oxo-1,2,3,4-tetrahydropyrimidine-5-carboxylic acid (3,3-diphenylpropyl)amide 1) Synthesis of benzyl 4-(3-chlorophenyl)-6-methyl-2-oxo-1,2,3,4-tetrahydropyrimidine-5-carboxylate:

5.00 g (26.0 mmol) of benzyl acetoacetate, 3.66 g (26.0 mmol) of 3-chlorobenzaldehyde and 3.12 g (52 .0 mmol) of urea were dissolved in 50 ml of ethanol. 1 ml of concentrated hydrochloric acid was added to the obtained solution at room temperature, and the obtained mixture was stirred at 100° C. for 24 hours. A catalytic amount of p-toluenesulfonic acid was added to the mixture and they were stirred at 60° C. overnight. The temperature was lowered to room temperature. 10 ml of water was added to the obtained reaction mixture. Crystals thus formed were taken by the filtration and then dried under reduced pressure to obtain the title compound.

Yield: 5.43 g (15.2 mmol) (58.5%)
MS (ESI, m/z) 357 (M+H)+
$^1$H-NMR (CDCl3): 2.37 (3H, s), 5.05 (2H, dd), 5.36 (1H, s), 5.66 (1H, s), 7.11–7.32 (9H, m), 7.86 (1H, s)

2) Synthesis of 4-(3-chlorophenyl)-6-methyl-2-oxo-1,2,3,4-tetrahydropyrimidine-5-carboxylic acid:

50 ml of ethyl acetate was added to a mixture of 2.83 g (7.93 mmol) of benzyl 4-(3-chlorophenyl)-6-methyl-2-oxo-1,2,3,4-tetrahydropyrimidine-5-carboxylate and a catalytic amount of 10% palladium/carbon, and they were stirred together at room temperature in hydrogen atmosphere under normal pressure overnight. The catalyst was filtered out, and the obtained filtrate was concentrated under reduced pressure to obtain the unrefined title compound.

Yield: 1.48 g (5.55 mmol) (69.9%)
MS (ESI, m/z) 267 (M+H)+
$^1$H-NMR (CD3OD): 2.32 (3H, s), 5.32 (1H, d), 7.21–7.36 (4H, m).

3) Synthesis of 4-(3-chlorophenyl)-6-methyl-2-oxo-1,2,3,4-tetrahydropyrimidine-5-carboxylic acid (3,3-diphenylpropyl)amide:

150 mg (0.562 mmol) of 4-(3-chlorophenyl)-6-methyl-2-oxo-1,2,3,4-tetrahydropyrimidine-5-carboxylic acid and 178 mg (0.843 mmol) of 3,3-diphenylpropylamine were dissolved in 10 ml of DMF. 162 mg (0.843 mmol) of 1-ethyl-3-(3-dimethylaminopropyl)carbodiimide hydrochloride (hereinafter referred to as WSC hydrochloride) was added to the obtained solution under cooling with ice, and they were stirred at room temperature overnight. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=50/1 to 10/1) to obtain the title compound.

Yield: 180 mg (0.391 mmol) (69.6%)
MS (ESI, m/z) 460 (M+H)+
$^1$H-NMR (CDCl3): 1.97 (3H, s), 2.07–2.09 (2H, m), 3.00–3.19 (2H, m), 3.68 (1H, t), 5.24 (1H, s), 5.42 (1H, t), 6.44 (1H, s), 8.32 (1H, s).

EXAMPLE 4

Synthesis of 4-(3-chlorophenyl)-6-methyl-2-oxo-1,2,3,4-tetrahydropyrimidine-5-carboxylic acid (3-phenyl-2-propene-1-yl)amide 120 mg (0.450 mmol) of 4-(3-chlorophenyl)-6-methyl-2-oxo-1,2,3,4-tetrahydropyrimidine-5-carboxylic acid and 71.9 mg (0.540 mmol) of 3-phenyl-2-propene-1-ylamine were dissolved in 10 ml of DMF. 129 mg (0.675 mmol) of WSC hydrochloride was added to the obtained solution under cooling with ice, and they were stirred at room temperature overnight. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=50/1 to 10/1) to obtain the title compound.

Yield: 32.3 mg (0.085 mmol) (18.8%)
MS (ESI, m/z) 382 (M+H)+
$^1$H-NMR (CDCl3): 2.24 (3H, d), 3.86–3.92 (2H, m), 5.40 (1H, s), 6.03 (1H, dt), 6.27 (1H, d), 7.25–7.34 (9H, m).

EXAMPLE 5

Synthesis of 4-(3-chlorophenyl)-6-methoxymethyl-2-oxo-1,2,3,4-tetrahydropyrimidine-5-carboxylic acid (3,3-diphenylpropyl)amide 1) Synthesis of benzyl 4-methoxyacetoacetate:

1.00 g (4.41 mmol) of benzyl 4-chloroacetoacetate was dissolved in 10 ml of THF. 2.55 g (13.2 mmol) of sodium methoxide (28% methanol) was added to the obtained solution under cooling with ice, and they were stirred at room temperature for 24 hours. The reaction mixture was concentrated under reduced pressure, and 1 N hydrochloric acid was added to the mixture under cooling with ice. After the extraction with ethyl acetate, the product was washed with saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (hexane/ethyl acetate=10/1 to 5/1) to obtain the title compound.

Yield: 630 mg (3.05 mmol) (69.3%)
MS (ESI, m/z) 205 (M–H)–
$^1$H-NMR (CDCl3): 3.36 (3H, s), 3.56 (2H, s), 4.05 (2H, s), 5.18 (2H, s), 7.35–7.38 (5H, m).

2) Synthesis of benzyl 4-(3-chlorophenyl)-6-methoxymethyl-2-oxo-1,2,3,4-tetrahydropyrimidine-5-carboxylate:

630 mg (3.05 mmol) of benzyl 4-methoxyacetoacetate, 429 mg (3.05 mmol) of 3-chlorobenzaldehyde and 366 mg (6.10 mmol) of urea were dissolved in 50 ml of ethanol. A catalytic amount of concentrated hydrochloric acid was added to the obtained solution at room temperature, and they were stirred at 60° C. for 24 hours. After the concentration under reduced pressure, the reaction mixture was diluted with ethyl acetate and then washed with saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (hexane/ethyl acetate=3/1) to obtain the title compound.

Yield: 330 mg (0.853 mmol) (28.0%)
MS (ESI, m/z) 387 (M+H)+
$^1$H-NMR (CDCl3): 3.44 (3H, s), 4.66 (2H, s), 5.04 (2H, dd), 5.34 (1H, d), 6.46 (1H, s), 7.11–7.36 (9H, m), 7.70 (1H, s).

3) Synthesis of 4-(3-chlorophenyl)-6-methylmethyl-2-oxo-1,2,3,4-tetrahydropyrimidine-5-carboxylic acid:

10 ml of ethyl acetate was added to a mixture of 330 mg (0.853 mmol) of benzyl 4-(3-chlorophenyl)-6-methoxymethyl-2-oxo-1,2,3,4-tetrahydropyrimidine-5-carboxylate and a catalytic amount of 10% palladium/carbon, and they were stirred together at room temperature in hydrogen atmosphere under normal pressure overnight. The catalyst was filtered out, and the obtained filtrate was concentrated under reduced pressure to obtain the unrefined title compound.

Yield: 264 mg (0.890 mmol) (quantitative yield)
MS (ESI, m/z) 295 (M–H)–
$^1$H-NMR (CD3OD): 3.43 (3H, s), 4.66 (2H, dd), 5.33 (1H, s), 7.25–7.34 (4H, m).

4) Synthesis of 4-(3-chlorophenyl)-6-methoxymethyl-2-oxo-1,2,3,4-tetrahydropyrimidine-5-carboxylic acid (3,3-diphenylpropyl)amide:

130 mg (0.438 mmol) of 4-(3-chlorophenyl)-6-methoxymethyl-2-oxo-1,2,3,4-tetrahydropyrimidine-5-carboxylic acid and 139 mg (0.657 mmol) of 3,3-diphenylpropylamine were dissolved in 10 ml of DMF. 126 mg (0.657 mmol) of WSC hydrochloride was added to the obtained solution under cooling with ice, and they were stirred at room temperature overnight. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=50/1) to obtain the title compound.

Yield: 57.4 mg (0.117 mmol) (26.7%)
MS (ESI, m/z) 490 (M+H)+
$^1$H-NMR (CDCl3): 2.12 (2H, q), 3.03–3.21 (2H, m), 3.42 (3H, s), 3.67 (1H, t), 4.47 (2H, dd), 5.12 (1H, d), 5.33 (2H, br), 7.08–7.32 (14H, m).

EXAMPLE 6

Synthesis of 4-(3-chlorophenyl)-6-methoxymethyl-2-oxo-1,2,3,4-tetrahydropyrimidine-5-carboxylic acid (3-phenylpropyl)amide 60.0 mg (0.225 mmol) of 4-(3-chlorophenyl)-6-methoxymethyl-2-oxo-1,2,3,4-tetrahydropyrimidine-5-carboxylic acid and 36.5 mg (0.270 mmol) of 3-phenylpropylamine were dissolved in 10 ml of dichloromethane. 64.7 mg (0.338 mmol) of WSC hydrochloride was added to the obtained solution under cooling with ice, and they were stirred at room temperature overnight. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=100/1 to 10/1) to obtain the title compound.

Yield: 45.0 mg (0.109 mmol) (48.3%)
MS (ESI, m/z) 414 (M+H)+
$^1$H-NMR (CDCl3): 1.80–1.90 (2H, m), 2.62–2.68 (2H, m), 3.22–3.35 (5H, m), 4.59 (1H, dt), 4.75 (1H, d), 5.42 (1H, dt), 5.86 (1H, d), 7.15–7.34 (9H, m), 10.40 (1H, br).

EXAMPLE 7

Synthesis of 6-(2chloroethoxymethyl)-4-(3-chlorophenyl)-2-oxo-1,2,3,4-tetrahydropyrimidine-5-carboxylic acid (3,3-diphenylpropyl)amide 1) Synthesis of benzyl 4-bromoacetoacetate:

5.00 g (26.0 mmol) of benzyl acetoacetate was dissolved in 50 ml of ether. 4.99 g (31.2 mmol) of bromine was added to the obtained solution under cooling with ice, and they were stirred at room temperature for 24 hours. 50 ml of water was added to the reaction mixture under cooling with ice. After the extraction with ether, the organic layer was dried over anhydrous magnesium sulfate and then concentrated under reduced pressure to obtain the unpurified title compound.

Yield: 7.51 g (27.7 mmol) (quantitative yield).
$^1$H-NMR (CDCl3): 3.76 (2H, s), 4.02 (2H, s), 5.19 (2H, s), 7.37 (5H, s).

2) Synthesis of benzyl 4-(2-chloroethoxy)acetoacetate:

1.50 g (37.4 mmol) of sodium hydride (60% oily) was suspended in 30 ml of THF. 1.51 g (18.7 mmol) of 2-chloroethanol was added to the obtained suspension at −20° C., and they were stirred for 30 minutes. 4.23 g (15.6 mmol) of benzyl 4-bromoacetoacetate dissolved in 20 ml of THF was added dropwise to the reaction mixture at −20° C. for the duration of 1 hour. The obtained mixture was stirred overnight while the temperature was elevated to room temperature. 1 N hydrochloric acid was added to the reaction mixture under cooling with ice. After the extraction with ethyl acetate, the product was washed with saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (hexane/ethyl acetate=10/1 to 3/1) to obtain the title compound.

Yield: 850 mg (3.14 mmol) (20.1%).
$^1$H-NMR (CDCl3): 3.57–3.61 (4H, m), 3.72 (2H, t), 4.18 (2H, s), 5.18 (2H, s), 7.37 (5H, s).

3) Synthesis of benzyl 6-(2-chloroethoxymethyl)-4-(3-chlorophenyl)-2-oxo-1,2,3,4-tetrahydropyrimidine-5-carboxylate:

770 mg (2.84 mmol) of benzyl 4-(2-chloroethoxy)acetoacetate, 400 mg (2.84 mmol) of 3-chlorobenzaldehyde and 341 mg (5.68 mmol) of urea were dissolved in 20 ml of ethanol. A catalytic amount of concentrated hydrochloric acid was added to the obtained solution at room temperature, and they were stirred at 80° C. for 24 hours. After the concentration under reduced pressure, the reaction mixture was diluted with ethyl acetate and then washed with saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (hexane/ethyl acetate= 10/1 to 3/1) to obtain the title compound.

Yield: 353 mg (0.810 mmol) (28.6%).
MS (ESI, m/z) 435 (M+H)+.
$^1$H-NMR (CDCl3): 3.47–3.52 (3H, m), 3.81–3.87 (1H, m), 3.98 (1H, d), 4.70 (1H, d), 5.04 (1H, s), 5.18 (2H, dd), 5.61 (1H, s), 7.26–7.41 (9H, m), 9.66 (1H, s).

4) Synthesis of 6-(2-chloroethoxymethyl)-4-(3-chlorophenyl)-2-oxo-1,2,3,4-tetrahydropyrimidine-5-carboxylic acid:

20 ml of ethyl acetate was added to a mixture of 353 mg (0.810 mmol) of benzyl 6-(2-chloroethoxymethyl)-4-(3-chlorophenyl)-2-oxo-1,2,3,4-tetrahydropyrimidine-5-carboxylic acid and a catalytic amount of 10% palladium/carbon, and they were stirred together at room temperature in hydrogen atmosphere under normal pressure overnight. The catalyst was filtered out, and the obtained filtrate was concentrated under reduced pressure to obtain the unrefined title compound.

Yield: 284 mg (0.853 mmol) (quantitative yield).
MS (ESI, m/z) 343 (M−H)−.
$^1$H-NMR (CD3OD): 3.53–3.57 (2H, m), 3.62–3.69 (1H, m), 3.81–3.92 (1H, m), 4.29 (1H, d), 5.12 (1H, s), 7.34 (3H, s), 7.46 (1H, s).

5) Synthesis of 6-(2-chloroethoxymethyl)-4-(3-chlorophenyl)-2-oxo-1,2,3,4-tetrahydropyrimidine-5-carboxylic acid (3,3-diphenylpropyl)amide:

139 mg (0.417 mmol) of 6-(2-chloroethoxymethyl)-4-(3-chlorophenyl)-2-oxo-1,2,3,4-tetrahydropyrimidine-5-carboxylic acid and 106 mg (0.500 mmol) of 3,3-diphenylpropylamine were dissolved in 10 ml of dichloromethane. 120 mg (0.626 mmol) of WSC hydrochloride was added to the obtained solution under cooling with ice, and they were stirred at room temperature overnight. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=50/1) to obtain the title compound.

Yield: 200 mg (0.370 mmol) (88.8%).

MS (ESI, m/z) 538 (M+H)+.

$^1$H-NMR (DMSO-d6): 2.26 (2H, q), 3.13 (2H, t), 3.58 (2H, t), 3.66 (1H, dd), 3.81–3.95 (1H, m), 3.98 (1H, t), 4.23 (1H, d), 4.78 (1H, d), 5.07 (1H, s), 7.10–7.18 (2H, m), 7.25–7.31 (11H, m), 7.43 (1H, s).

EXAMPLE 8

Synthesis of 4-(3-chlorophenyl)-2-oxo-6-(2-piperidine-1-yl-ethoxymethyl)-1,2,3,4-tetrahydropyrimidine-5-carboxylic acid (3,3-diphenylpropyl)amide 135 mg (0.251 mmol) of 6-(2-chloroethoxymethyl)-4-(3-chlorophenyl)-2-oxo-1,2,3,4-tetrahydropyrimidine-5-carboxylic acid and 376 mg (2.51 mmol) of sodium iodide were dissolved in 10 ml of acetone, and the obtained solution was stirred at 70° C. for 5 days. The reaction mixture was diluted with 10 ml of dichloromethane, and crystals thus formed were filtered out. The filtrate was concentrated under reduced pressure. The residue was dissolved in 10 ml of acetonitrile. 64.1 mg (0.753 mmol) of piperidine was added to the solution, and they were stirred at 50° C. for 2 days. After the concentration under reduced pressure, the reaction mixture was diluted with ethyl acetate and then washed with saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=50/1 to 10/1) to obtain the title compound.

Yield: 47.0 mg (0.080 mmol) (31.9%).

MS (ESI, m/z) 587 (M+H)+.

$^1$H-NMR (CDCl3): 1.42 (2H, br), 1.54–1.61 (2H, m), 2.27 (2H, q), 2.37–2.47 (4H, m), 2.58 (1H, q), 3.11 (2H, br), 3.21 (1H, q), 3.53–3.60 (1H, m), 3.75–3.82 (1H, m), 3.96 (1H, t), 4.04 (1H, d), 4.66 (1H, d), 4.90 (1H, s), 5.85 (1H, br), 7.16–7.33 (14H, m), 10.37 (1H, br).

EXAMPLE 9

Synthesis of 6-(2-chloroethoxymethyl)-4-(3-chlorophenyl)-2-oxo-1,2,3,4-tetrahydropyrimidine-5-carboxylic acid (3-phenylpropyl)amide 205 mg (0.594 mmol) of 6-(2-chloroethoxymethyl)-4-(3-chlorophenyl)-2-oxo-1,2,3,4-tetrahydropyrimidine-5-carboxylic acid and 96.4 mg (0.713 mmol) of 3-phenylpropylamine were dissolved in 10 ml of dichloromethane. 171 mg (0.891 mmol) of WSC hydrochloride was added to the obtained solution under cooling with ice, and they were stirred at room temperature overnight. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=50/1 to 30/1) to obtain the title compound.

Yield: 247 mg (0.534 mmol) (89.9%).

MS (ESI, m/z) 462 (M+H)+.

$^1$H-NMR (DMSO-d6): 1.70 (2H, t), 2.57 (2H, t), 3.05–3.13 (2H, m), 3.66 (2H, t), 3.71–3.85 (2H, m), 4.43 (1H, d), 4.79 (1H, t), 5.01 (1H, s), 7.17–7.37 (9H, m), 7.74 (1H, s), 7.99 (1H, t), 10.35 (1H, s).

EXAMPLE 10

Synthesis of 4-(3-chlorophenyl)-6-methyl-2-oxo-1,2,3,4-tetrahydropyrimidine-5-carboxylic acid (3-morpholine-4-yl-propyl)amide 240 mg (0.900 mmol) of 4-(3-chlorophenyl)-6-methyl-2-oxo-1,2,3,4-tetrahydropyrimidine-5-carboxylic acid and 156 mg (1.08 mmol) of N-(3-aminopropyl)morpholine were dissolved in 10 ml of DMF. 259 mg (1.35 mmol) of WSC hydrochloride was added to the obtained solution under cooling with ice, and they were stirred at room temperature overnight. After the concentration under reduced pressure, the reaction mixture was diluted with ethyl acetate and then washed with saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=50/1 to 10/1) to obtain the title compound.

Yield: 92.0 mg (0.234 mmol) (26.0%).

MS (ESI, m/z) 393 (M+H)+.

$^1$H-NMR (CDCl3): 1.51–1.56 (2H, m), 2.08 (3H, s), 2.18–2.34 (8H, m), 3.44–3.59 (4H, m), 5.46 (1H, s), 6.16 (1H, s), 6.77 (1H, t), 7.18–7.31 (4H, m), 8.11 (1H, s).

EXAMPLE 11

Synthesis of 4-(3-chlorophenyl)-6-methyl-2-oxo-1,2,3,4-tetrahydropyrimidine-5-carboxylic acid (3-pyrrolidine-1-yl-propyl)amide 218 mg (0.817 mmol) of 4-(3-chlorophenyl)-6-methyl-2-oxo-1,2,3,4-tetrahydropyrimidine-5-carboxylic acid and 126 mg (0.981 mmol) of 1-(3-aminopropyl)pyrrolidine were dissolved in 10 ml of DMF. 235 mg (1.23 mmol) of WSC hydrochloride was added to the obtained solution under cooling with ice, and they were stirred at room temperature overnight. After the concentration under reduced pressure, the reaction mixture was diluted with ethyl acetate and then washed with saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=50/1 to 10/1) to obtain the title compound.

Yield: 65.1 mg (0.173 mmol) (21.1%).

MS (ESI, m/z) 377 (M+H)+.

$^1$H-NMR (CD3OD): 1.53–1.63 (2H, m), 1.74–1.80 (4H, m), 2.04 (3H, s), 2.22–2.30 (2H, m), 2.41–2.45 (4H, m), 3.09–3.25 (2H, m), 5.35 (1H, s), 7.22–7.35 (4H, m).

EXAMPLE 12

Synthesis of 4-(3-chlorophenyl)-6-methyl-2-oxo-1,2,3,4-tetrahydropyrimidine-5-carboxylic acid (3-imidazole-1-yl-propyl)amide 200 mg (0.750 mmol) of 4-(3-chlorophenyl)-6-methyl-2-oxo-1,2,3,4-tetrahydropyrimidine-5-carboxylic acid and 113 mg (0.900 mmol) of 1-(3-aminopropyl)imidazole were dissolved in 10 ml of DMF. 216 mg (1.13 mmol) of WSC hydrochloride was added to the obtained solution under cooling with ice, and they were stirred at room temperature overnight. After the concentration under reduced pressure, the reaction mixture was diluted with ethyl acetate and then washed with saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=50/1 to 10/1) to obtain the title compound.

Yield: 135 mg (0.361 mmol) (48.1%).

MS (ESI, m/z) 374 (M+H)+.

$^1$H-NMR (CD3OD): 1.81 (2H, t), 2.04 (3H, s), 3.02–3.11 (2H, m), 3.15–3.24 (2H, m), 3.72 (2H, t), 5.39 (1H, s), 6.93 (1H, s), 7.00 (1H, s), 7.23–7.35 (4H, m), 7.50 (1H, s).

EXAMPLE 13

Synthesis of 4-(3-chlorophenyl)-6-methyl-2-oxo-1,2,3,4-tetrahydropyrimidine-5-carboxylic acid [3-(4-methylpiperazine-yl)-propyl]amide 225 mg (0.844 mmol) of 4-(3-chlorophenyl)-6-methyl-2-oxo-1,2,3,4-tetrahydropyrimidine-5-carboxylic acid and 159 mg (1.01 mmol) of 1-(aminopropyl)-4-methylpiperazine were dissolved in 10 ml of DMF. 243 mg (1.27 mmol) of WSC hydrochloride was added to the obtained solution under cooling with ice, and they were stirred at room temperature overnight. After the concentration under reduced pressure, the reaction mixture was diluted with ethyl acetate and then washed with saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=50/1 to 10/1) to obtain the title compound.

Yield: 159 mg (0.384 mmol) (45.5%).

MS (ESI, m/z) 406 (M+H)+.

$^1$H-NMR (CD3OD): 1.55 (2H, t), 2.03 (3H, s), 2.17–2.23 (2H, m), 2.26 (3H, s), 2.43 (8H, br), 3.08–3.26 (2H, m), 5.35 (1H, s), 7.21–7.38 (4H, m).

EXAMPLE 14

Synthesis of 6-(2-azidoethoxymethyl)-4-(3-chlorophenyl)-2-oxo-1,2,3,4-tetrahydropyrimidine-5-carboxylic acid (3-phenylpropyl)amide 180 mg (0.389 mmol) of 6-(2-chloroethoxymethyl)-4-(3-chlorophenyl)-2-oxo-1,2,3,4-tetrahydropyrimidine-5-carboxylic acid (3-phenylpropyl)amide was dissolved in 10 ml of DMF. 38.0 mg (0.584 mmol) of sodium azide and 58.3 mg (0.389 mmol) of sodium iodide were added to the obtained solution, and they were stirred at 60° C. for 2 days. After the concentration under reduced pressure, the reaction mixture was diluted with ethyl acetate and then washed with saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (dichloromethane/methanol=100/1) to obtain the title compound.

Yield: 180 mg (0.384 mmol) (98.7%).

MS (ESI, m/z) 469 (M+H)+.

$^1$H-NMR (CDCl3): 1.78–1.85 (2H, m), 2.62 (2H, t), 3.21–3.31 (4H, m), 3.42–3.49 (1H, m), 3.64–3.70 (1H, m), 4.01 (1H, d), 4.65 (1H, d), 4.94 (1H, s), 6.22 (1H, t), 6.31 (1H, s), 7.14–7.34 (9H, m), 7.96 (1H, s), 10.42 (1H, s).

EXAMPLE 15

Synthesis of 6-(2-azidoethoxymethyl)-4-(3-chlorophenyl)-2-oxo-1,2,3,4-tetrahydropyrimidine-5-carboxylic acid (3,3-diphenylpropyl)amide 195 mg (0.362 mmol) of 6-(2-chloroethoxymethyl)-4-(3-chlorophenyl)-2-oxo-1,2,3,4-tetrahydropyrimidine-5-carboxylic acid (3,3-diphenylpropyl)amide was dissolved in 10 ml of DMF. 35.3 mg (0.543 mmol) of sodium azide and 54.3 mg (0.362 mmol) of sodium iodide were added to the obtained solution, and they were stirred at 60° C. for 2 days. After the concentration under reduced pressure, the reaction mixture was diluted with ethyl acetate and then washed with saturated aqueous sodium chloride solution. The organic layer was dried over anhydrous magnesium sulfate and then concentrated under reduced pressure. The residue was purified by the silica gel chromatography (dichloromethane/methanol=100/1) to obtain the title compound.

Yield: 196 mg (0.359 mmol) (99.1%).

MS (ESI, m/z) 545 (M+H)+.

$^1$H-NMR (CDCl3): 2.24 (2H, q), 3.15–3.28 (4H, m), 3.41–3.48 (1H, m), 3.61–3.68 (1H, m), 3.93 (1H, t), 3.98 (1H, d), 4.61–4.63 (1H, m), 4.81 (1H, s), 5.81 (1H, t), 6.14 (1H, s), 7.15–7.32 (14H, m), 10.40 (1H, s).

EXAMPLE 16

Synthesis of 6-(2-aminoethoxymethyl)-4-(3-chlorophenyl)-2-oxo-1,2,3,4-tetrahydropyrimidine-5-carboxylic acid (3-phenylpropyl)amide 10 ml of ethyl acetate was added to a mixture of 164 mg (0.350 mmol) of 6-(2-azidoethoxymethyl)-4-(3-chlorophenyl)-2-oxo-1,2,3,4-tetrahydropyrimidine-5-carboxylic acid (3-phenylpropyl)amide and a catalytic amount of 10% palladium/carbon, and they were stirred at room temperature in hydrogen atmosphere under normal pressure for 24 hours. The catalyst was filtered out, and the filtrate was concentrated under reduced pressure. The residue was purified by the basic silica gel chromatography (dichloromethane/methanol=100/1 to 20/1) to obtain the title compound.

Yield: 138 mg (0.312 mmol) (89.0%).

MS (ESI, m/z) 443 (M+H)+.

$^1$H-NMR (CDCl3): 1.78–1.88 (2H, m), 2.64 (2H, t), 2.70–2.75 (2H, m), 3.24–3.34 (3H, m), 3.52–3.59 (1H, m), 3.94 (1H, d), 4.65 (1H, d), 4.85 (1H, s), 5.91 (1H, t), 6.31 (1H, s), 7.15–7.33 (9H, m), 10.41 (1H, br).

EXAMPLE 17

Synthesis of 6-(2-aminoethoxymethyl)-4-(3-chlorophenyl)-2-oxo-1,2,3,4-tetrahydropyrimidine-5-carboxylic acid (3,3-diphenylpropyl)amide 10 ml of ethyl acetate was added to a mixture of 180 mg (0.330 mmol) of 6-(2-azidoethoxymethyl)-4-(3-chlorophenyl)-2-oxo-1,2,3,4-tetrahydropyrimidine-5-carboxylic acid (3,3-diphenylpropyl)amide and a catalytic amount of 10% palladium/carbon, and they were stirred at room temperature in hydrogen atmosphere under normal pressure overnight. The catalyst was filtered out, and the filtrate was concentrated under reduced pressure. The residue was purified by the basic silica gel chromatography (dichloromethane/methanol=100/1 to 20/1) to obtain the title compound.

Yield: 162 mg (0.312 mmol) (94.5%).

MS (ESI, m/z) 519 (M+H)+.

$^1$-NMR (CDCl3): 2.27 (2H, q), 2.66–2.78 (2H, m), 3.20–3.33 (3H, m), 3.52–3.58 (1H, m), 3.89–3.97 (2H, m), 4.63 (1H, d), 4.73 (1H, s), 5.60 (1H, t), 6.07 (1H, s), 7.14–7.33 (14H, m), 10.40 (1H, br).

EXAMPLE 18

Synthesis of 4-(3-chlorophenyl)-6-methyl-2-oxo-1,2,3,4-tetrahydropyrimidine-5-carboxylic acid (3-phenylpropyl)amide The title compound was obtained in the same manner as that of Example 3.

MS (ESI, m/z) 357 (M+H)+.

$^1$H-NMR (CDCl3): 1.67 (2H, quint), 2.07 (3H, s), 2.45 (2H, t), 3.09–3.31 (2H, m), 5.24 (1H, t), 5.31 (1H, s), 6.09 (1H, s), 7.05 (2H, d), 7.16–7.30 (7H, m), 8.04 (1H, s).

EXAMPLE 19

Synthesis of benzyl 4-(3-chlorophenyl)-3-(3,3-diphenylpropylcarbamoyl)-6-methyl-2-oxo-1,2,3,4-tetrahydropyrimidine-5-carboxylate 1) Synthesis of benzyl 2-acetyl-3-(3-chlorophenyl)acrylate (E/Z mixture):

8.00 g (41.6 mmol) of benzyl acetoacetate, 5.85 g (41.6 mmol) of 3-chlorobenzaldehyde, 354 mg (4.16 mmol) of piperidine and 342 mg (4.16 mmol) of acetic acid were dissolved in 100 ml of isopropanol, and the obtained solution was stirred at room temperature for 24 hours. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure to obtain the crude title compound.

Yield: 13.5 mg (42.9 mmol) (quantitative yield).

2) Synthesis of benzyl 4-(3-chlorophenyl)-2-methoxy-6-methyl-1,4-dihydropyrimidine-5-carboxylate:

5.00 g (15.9 mmol) of benzyl 2-acetyl-3-(3-chlorophenyl)acrylate, 3.56 g (20.6 mmol) of 0-methylisourea sulfate and 5.34 g (63.6 mmol) of sodium hydrogencarbonate were dissolved in 30 ml of DMF, and he obtained solution was stirred at 70° C. for 24 hours. The precipitate was filtered out, and the filtrate was washed with saturated aqueous sodium chloride solution. The organic layer was dried over anhydrous magnesium sulfate and then concentrated under reduced pressure. The residue was purified by the silica gel chromatography (hexane/ethyl acetate=5/1 to 1/1) to obtain the title compound.

Yield: 2.54 mg (6.99 mmol) (44.0%).

MS (ESI, m/z) 371 (M+H)+.

$^1$H-NMR (CDCl3): 2.35 (3H, s), 3.72 (3H, s), 5.07 (2H, d), 5.60 (1H, s), 5.96 (1H, br), 7.11–7.38 (9H, m).

3) Synthesis of 5-benzyl 1-(4-nitrophenyl) 6-(3-chlorophenyl)-2-methoxy-4-methyl-6H-pyrimidine-1,5-dicarboxylate:

558 mg (1.50 mmol) of benzyl 4-(3-chlorophenyl)-2-methoxy-6-methyl-1,4-dihydropyrimidine-5-carboxylate and 364 mg (1.81 mmol) of p-nitrophenyl chloroformate were dissolved in 10 ml of dichloromethane. 1 ml of saturated sodium hydrogencarbonate solution was added to the obtained solution at 0° C., and they were stirred at room temperature for 24 hours. The reaction mixture was diluted with dichloromethane and then washed with water and saturated aqueous sodium chloride solution. The organic layer was dried over anhydrous magnesium sulfate and then concentrated under reduced pressure. The product was washed with ether and then dried under reduced pressure to obtain the title compound.

Yield: 618 mg (1.15 mmol) (76.8%).

MS (ESI, m/z) 536 (M+H)+.

$^1$H-NMR (CDCl3): 2.51 (3H, s), 3.97 (3H, s), 5.16 (2H, dd), 6.30 (1H, s), 7.18–7.38 (1H, m), 8.29 (2H, d).

4) Synthesis of benzyl 6-(3-chlorophenyl)-2-methoxy-4-methyl-1-(3,3-diphenylpropylcarbamoyl)-1,6-dihydroyrimidine-5-carboxylate:

10 ml of acetonitrile was added to a mixture of 200 mg (0.373 mmol) of 5-benzyl 1-(4-nitrophenyl) 6-(3-chlorophenyl)-2-methoxy-4-methyl-6H-pyrimidine-1,5-dicarboxylate and 78.9 mg (0.373 mmol) of 3,3-diphenylpropylamine, and they were stirred at 60° C. for 30 minutes. The solvent was evaporated under reduced pressure to obtain the title compound.

Yield: 149 mg (0.245 mmol) (65.7%).

MS (ESI, m/z) 608 (M+H)+.

$^1$H-NMR (CDCl3): 2.31 (2H, dd), 2.44 (3H, s), 3.20–3.35 (2H, m), 3.89–3.94 (4H, m), 5.12 (2H, dd), 6.63 (1H, t), 6.67 (1H, s), 6.71 (1H, br), 7.13–7.27 (19H, m).

5) Synthesis of benzyl 4-(3-chlorophenyl)-3-(3,3-diphenylpropylcarbamoyl)-6-methyl-2-oxo-1,2,3,4-tetrahydropyrimidine-5-carboxylate:

149 mg (0.245 mmol) of benzyl 6-(3-chlorophenyl)-2-methoxy-4-methyl-1-(3,3-diphenylpropylcarbamoyl)-1,6-dihydroyrimidine-5-carboxylate was dissolved in a mixture of 5 ml of ethyl acetate and 5 ml of methanol. 10 ml of 1 N hydrochloric acid was added to the obtained solution, and they were stirred at room temperature for 1 hour. After the concentration under reduced pressure, the reaction mixture was diluted with ethyl acetate and then washed with 1 N aqueous sodium hydroxide solution and saturated aqueous sodium chloride solution. The organic layer was dried over anhydrous magnesium sulfate and then concentrated under reduced pressure. The residue was purified by the basic silica gel chromatography (100% dichloromethane) to obtain the crude title compound.

Yield: 141 mg (0.237 mmol) (96.9%).

MS (ESI, m/z) 594 (M+H)+.

$^1$H -NMR (CDCl3): 2.28 (2H, dd), 2.35 (3H, s), 3.12–3.35 (2H, m), 3.92 (1H, t), 5.14 (2H, dd), 6.71 (1H, s), 7.11–7.32 (19H, m), 7.77 (1H, s), 8.74 (1H, t).

EXAMPLE 20

Synthesis of 4-(3-chlorophenyl)-3-(3,3-diphenylpropylcarbamoyl)-6-methyl-2-oxo-1,2,3,4-tetrahydropyrimidine-5-carboxylic acid 10 ml of ethyl acetate was added to a mixture of 141 mg (0.237 mmol) of benzyl 4-(3-chlorophenyl)-3-(3,3-diphenylpropylcarbamoyl)-6-methyl-2-oxo-1,2,3,4-tetrahydropyrimidine-5-carboxylate and a catalytic amount of 10% palladium/carbon, and they were stirred at room temperature in hydrogen atmosphere under normal pressure overnight. The catalyst was filtered out, and the obtained filtrate was concentrated under reduced pressure. The residue was washed with hexane/ethyl acetate (1/1) and then dried under reduced pressure to obtain the title compound.

Yield: 118 mg (0.234 mmol) (98.8%).

MS (ESI, m/z) 504 (M+H)+.

$^1$H-NMR (CDCl3): 2.34 (2H, q), 2.42 (3H, s), 3.13–3.24 (1H, m), 3.27–3.36 (1H, m), 3.94 (1H, t), 6.70 (1H, s), 7.07–7.32 (14H, m), 8.67 (1H, t).

EXAMPLE 21

Synthesis of 3-carbamoyl-4-(3-chlorophenyl)-6-methyl-2-oxo-1,2,3,4-tetrahydropyrimidine-5-carboxylic acid (3,3-diphenylpropyl)amide 1) Synthesis of 5-benzyl 1-(4-nitrophenyl) 6-(3-chlorophenyl)-4-methyl-2-oxo-3,6-dihydro-2H-pyrimidine-1,5-dicarboxylate:

217 mg (0.405 mmol) of 5-benzyl 1-(4-nitrophenyl) 6-(3-chlorophenyl)-2-methoxy-4-methyl-6H-pyrimidine-1,5-dicarboxylate was dissolved in a mixture of 5 ml of THF and 5 ml of methanol. 1 ml of 3 N hydrochloric acid was added to the obtained solution, and they were stirred at room temperature for 12 hours. After the concentration under reduced pressure, the reaction mixture was diluted with ethyl acetate and then washed with saturated aqueous sodium chloride solution. The organic layer was dried over anhydrous magnesium sulfate and then concentrated under reduced pressure to obtain the title compound.

Yield: 213 mg (0.408 mmol) (quantitative yield).

MS (ESI, m/z) 520 (M–H)–.

$^1$H-NMR (CDCl3): 2.42 (3H, s), 5.18 (2H, dd), 6.39 (1H, s), 7.21–7.36 (11H, m), 8.23 (2H, d), 8.81 (1H, s).

2) Synthesis of benzyl 3-carbamoyl-4-(3-chlorophenyl)-6-methyl-2-oxo-1,2,3,4-tetrahydropyrimidine-5-carboxylate:

213 mg (0.408 mmol) of 5-benzyl 1-(4-nitrophenyl) 6-(3-chlorophenyl)-4-methyl-2-oxo-3,6-dihydro-2H-pyrimidine-1,5-dicarboxylate and 78.4 mg (0.816 mmol) of ammonium carbonate were dissolved in a mixture of 10 ml of ethanol and 5 ml of dichloromethane. The obtained solution was stirred at room temperature for 12 hours. After the concentration under reduced pressure, the reaction mixture was diluted with ethyl acetate and then washed with saturated aqueous sodium chloride solution. The organic layer was dried over anhydrous magnesium sulfate and then concentrated under reduced pressure. The product was washed with hexane/ethyl acetate (1/1) and then dried under reduced pressure to obtain the title compound.

Yield: 135 mg (0.338 mmol) (82.8%).

MS (ESI, m/z) 400 (M+H)+.

$^1$H-NMR (CDCl3): 2.42 (3H, s), 5.16 (2H, dd), 5.30 (1H, br), 6.71 (1H, s), 6.82 (1H, br), 7.20–7.32 (9H, m), 8.48 (1H, br).

3) Synthesis of 3-carbamoyl-4-(3-chlorophenyl)-6-methyl-2-oxo-1,2,3,4-tetrahydropyrimidine-5-carboxylic acid:

10 ml of ethyl acetate was added to a mixture of 135 mg (0.338 mmol) of benzyl 3-carbamoyl-4-(3-chlorophenyl)-6-methyl-2-oxo-1,2,3,4-tetrahydropyrimidine-5-carboxylate and a catalytic amount of 10% palladium/carbon, and they were stirred at room temperature in hydrogen atmosphere under normal pressure overnight. The catalyst was filtered out, and the obtained filtrate was concentrated under reduced pressure. The residue was washed with hexane/ethyl acetate (1/1) and then dried under reduced pressure to obtain the title compound.

Yield: 109 mg (0.352 mmol) (quantitative yield).

MS (ESI, m/z) 308 (M+H)+.

$^1$H-NMR (DMSO-d6): 2.29 (3H, s), 6.51 (1H, s), 7.16–7.20 (2H, m), 7.33–7.39 (2H, m), 7.56 (1H, br), 8.16 (1H, br), 10.02 (1H, br).

4) Synthesis of 3-carbamoyl-4-(3-chlorophenyl)-6-methyl-2-oxo-1,2,3,4-tetrahydropyrimidine-5-carboxylic acid (3,3-diphenylpropyl)amide:

102 mg (0.329 mmol) of 3-carbamoyl-4-(3-chlorophenyl)-6-methyl-2-oxo-1,2,3,4-tetrahydropyrimidine-5-carboxylic acid and 83.5 mg (0.395 mmol) of (3,3-diphenylpropyl)amine were dissolved in 10 ml of DMF. 94.6 mg (0.494 mmol) of WSC hydrochloride was added to the obtained solution under cooling with ice, and they were stirred at room temperature overnight. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the basic silica gel chromatography (dichloromethane/methanol=100/1 to 10/1) to obtain the crude title compound.

Yield: 124 mg (0.247 mmol) (74.9%).

MS (ESI, m/z) 503 (M+H)+.

$^1$H-NMR (CDCl3): 2.18–2.25 (5H, m), 3.20 (2H, dd), 3.77 (1H, t), 5.38 (1H, t), 5.55 (1H, br), 6.44 (1H, s), 7.11–7.30 (14H, m), 7.46 (1H, br), 8.50 (1H, br).

EXAMPLE 22

Synthesis of benzyl 4-(3-chlorophenyl)-3-(3-phenylpropylcarbamoyl)-6-methyl-2-oxo-1,2,3,4-tetrahydropyrimidine-5-carboxylate The title compound was obtained in the same manner as that of Example 19.

MS (ESI, m/z) 518 (M+H)+.

$^1$H-NMR (CDCl3): 1.85 (2H, quint), 2.37 (3H, s), 2.62 (2H, t), 3.20–3.40 (2H, m), 5.14 (2H, dd), 6.73 (1H, s), 7.11–7.31 (14H, m), 7.75 (1H, s), 8.75 (1H, t).

EXAMPLE 23

Synthesis of 4-(3-chlorophenyl)-6-methyl-2-oxo-3-(3-phenylpropylcarbamoyl)-1,2,3,4-tetrahydropyrimidine-5-carboxylic acid The title compound was obtained in the same manner as that of Example 20.

MS (ESI, m/z) 428 (M+H)+.

$^1$H-NMR (CDCl3): 1.88 (2H, quint), 2.43 (3H, s), 2.64 (2H, t), 3.21–3.43 (2H, m), 6.73 (1H, s), 7.07–7.33 (9H, m), 8.70 (1H, t).

EXAMPLE 24

Synthesis of 4-(3-chlorophenyl)-3-ethoxycarbonyl-6-methyl-2-oxo-1,2,3,4-tetrahydropyrimidine-5-carboxylic acid (3,3-diphenylpropyl)amide 1) Synthesis of benzyl 4-(3-chlorophenyl)-3-ethoxycarbonyl-6-methyl-2-oxo-1,2,3,4-tetrahydropyrimidine-5-carboxylate:

10 ml of pyridine was added to a mixture of 512 mg (1.38 mmol) of benzyl 4-(3-chlorophenyl)-2-methoxy-6-methyl-1,4-dihydropyrimidine-5-carboxylate and 180 mg (1.66 mmol) of ethyl chloroformate, and they were stirred at room temperature for 1 hour. The reaction mixture was diluted with ethyl acetate, then washed with water and saturated aqueous sodium chloride solution and concentrated under reduced pressure. The product was dissolved in a mixture of 5 ml of methanol and 5 ml of THF. 3 N hydrochloric acid was added to the obtained solution, and they were stirred at room temperature for 10 minutes. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (hexane/ethyl acetate= 10/1 to 1/1) to obtain the crude title compound.

Yield: 419 mg (0.977 mmol) (70.8%).
MS (ESI, m/z) 429 (M+H)+.
$^1$H-NMR (CDCl3): 1.33 (3H, t), 2.39 (3H, s), 4.28–4.38 (2H, m), 5.17 (2H, dd), 6.34 (1H, s), 7.01 (1H, br), 7.19–7.36 (9H, m).

2) Synthesis of 4-(3-chlorophenyl)-3-ethoxycarbonyl-6-methyl-2-oxo-1,2,3,4-tetrahydropyrimidine-5-carboxylic acid:

10 ml of ethyl acetate was added to a mixture of 345 mg (0.804 mmol) of benzyl 4-(3-chlorophenyl)-3-ethoxycarbonyl-6-methyl-2-oxo-1,2,3,4-tetrahydropyrimidine-5-carboxylate and a catalytic amount of 10% palladium/carbon, and they were stirred at room temperature in hydrogen atmosphere under normal pressure for 2 days. The catalyst was filtered out, and the obtained filtrate was concentrated under reduced pressure to obtain the title compound.

Yield: 291 mg (0.859 mmol) (quantitative yield).
MS (ESI, m/z) 339 (M+H)+.
$^1$H-NMR (CD3OD): 1.31 (3H, t), 2.37 (3H, s), 4.35–4.36 (2H, m), 6.30 (1H, s), 7.27–7.34 (4H, m).

3) Synthesis of 4-(3-chlorophenyl)-3-ethoxycarbonyl-6-methyl-2-oxo-1,2,3,4-tetrahydropyrimidine-5-carboxylic acid (3,3-diphenylpropyl)amide:

117 mg (0.346 mmol) of 4-(3-chlorophenyl)-3-ethoxycarbonyl-6-methyl-2-oxo-1,2,3,4-tetrahydropyrimidine-5-carboxylic acid and 110 mg (0.519 mmol) of 3,3-diphenylpropylamine were dissolved in 10 ml of dichloromethane. 99.5 mg (0.519 mmol) of WSC hydrochloride was added to the obtained solution under cooling with ice, and they were stirred at room temperature overnight. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was washed with hexane/ethyl acetate (1/1) and then dried under reduced pressure to obtain the title compound.

Yield: 146 mg (0.274 mmol) (79.3%).
MS (ESI, m/z) 532 (M+H)+.
$^1$H-NMR (CDCl3): 1.35 (3H, t), 2.21–2.30 (5H, m), 3.18–3.30 (2H, m), 3.80 (1H, t), 4.26–4.41 (2H, m), 5.18 (1H, t), 6.06 (1H, s), 6.60 (1H, br), 7.12–7.38 (14H, m).

EXAMPLE 25

Synthesis of 4-(3-chlorophenyl)-3-ethoxycarbonyl-6-methyl-2-oxo-1,2,3,4-tetrahydropyrimidine-5-carboxylic acid (3-phenylpropyl)amide The title compound was obtained in the same manner as that of Example 24.

MS (ESI, m/z) 456 (M+H)+.
$^1$H-NMR (CDCl3): 1.34 (2H, t), 1.80 (2H, quint), 2.23 (3H, s), 3.23–3.36 (2H, m), 4.33 (2H, tt), 5.24 (1H, t), 6.09 (1H, s), 7.08–7.37 (8H, m), 7.38 (1H, br).

EXAMPLE 26

Synthesis of 4-(3-chlorophenyl)-6-methyl-2-oxo-1,2,3,4-tetrahydropyrimidine-5-carboxylic acid (2-pyridine-4-ylethyl)amide The title compound was obtained in the same manner as that of Example 3.

MS (ESI, m/z) 371 (M+H)+, 369 (M–H)–.
$^1$H-NMR (DMSO-d6): 1.92 (2H, s), 2.65 (2H, t), 3.27–3.33 (2H, m), 5.20 (1H, d), 7.06–7.13 (3H, m), 7.21 (1H, s), 7.31–7.33 (1H, m), 7.53 (1H, s), 7.69 (1H, t), 8.36 (2H, q), 8.60 (1H, s).

EXAMPLE 27

Synthesis of 4-(3-chlorophenyl)-6-methyl-2-oxo-1,2,3,4-tetrahydropyrimidine-5-carboxylic acid (2-pyridine-3-ylethyl)amide The title compound was obtained in the same manner as that of Example 3.

MS (ESI, m/z) 371 (M+H)+, 369 (M–H)–.
$^1$H-NMR (DMSO-d6): 1.90 (3H, s), 2.68 (2H, t), 3.30 (2H, t), 5.19 (1H, d), 7.11 (1H, dt), 7.18–7.23 (2H, m), 7.28–7.36 (2H, m), 7.44 (1H, dt), 7.54 (1H, s), 7.70 (1H, t), 8.32 (1H, d), 8.36 (1H, dd), 8.60 (1H, s).

EXAMPLE 28

Synthesis of benzyl 4-(3-chlorophenyl)-3-[(2-methoxyphenyl)ethylcarbamoyl]-6-methyl-2-oxo-1,2,3,4-tetrahydro-pyrimidine-5-carboxylate The title compound was obtained in the same manner as that of Example 19.

$^1$H-NMR (CDCl3): 2.30 (3H, s), 2.85 (2H, td), 3.53 (2H, qd), 3.77 (3H, s), 5.07 (1H, d), 5.21 (1H, d), 6.73 (1H, s), 6.78–6.85 (2H, m), 7.05 (1H, dd), 7.13–7.35 (10H, m), 7.48 (1H, s), 8.66 (1H, t).

EXAMPLE 29

Synthesis of benzyl 4-(3-chlorophenyl)-3-[(2-(4-hydroxyphenyl)ethylcarbamoyl]-6-methyl-2-oxo-1,2,3,4-tetrahydro-pyrimidine-5-carboxylate The title compound was obtained in the same manner as that of Example 19.

MS (ESI, m/z) 520 (M+H)+, 518 (M–H)–.
$^1$H-NMR (CDCl3): 2.31 (3H, s), 2.70 (2H, q), 3.49 (2H, brs), 5.14 (2H, ABq), 5.51 (1H, brs), 6.69–6.71 (3H, m), 6.98 (2H, d), 7.16–7.31 (12H, m), 8.70 (1H, s).

EXAMPLE 30

Synthesis of benzyl 4-(3-chlorophenyl)-6-methyl-2-oxo-3-(phenoxyethylcarbamoyl)-1,2,3,4-tetrahydropyrimidine-5-carboxylate The title compound was obtained in the same manner as that of Example 19.

MS (ESI, m/z) 520 (M+H)+, 518 (M–H)–.
$^1$H-NMR (CDCl3): 2.35 (3H, s), 3.61–3.76 (2H, m), 4.05 (2H, t), 5.13 (2H, ABq), 6.72 (1H, s), 6.85 (2H, d), 6.93 (1H, t), 7.13–7.35 (10H,m), 9.05 (1H, t).

EXAMPLE 31

Synthesis of 4-(3-chlorophenyl)-3-[(2-(4-hydroxyphenyl)ethylcarbamoyl)-6-methyl-2-oxo-1,2,3,4-tetrahydro-pyrimidine-5-carboxylic acid The title compound was obtained in the same manner as that of Example 20.

MS (ESI, m/z) 428 (M–H)–.
$^1$H-NMR (DMSO-d6): 2.27 (3H, s), 2.61–2.64 (2H, m), 3.34–3.56 (2H, m), 6.51 (1H, s), 6.64 (2H, d), 6.96 (2H, d), 7.12–7.17 (2H, m), 7.31–7.39 (2H, m), 8.78 (1H, t), 10.00 (1H, s).

EXAMPLE 32

Synthesis of 4-(3-chlorophenyl)-6-methyl-2-oxo-3-(phenoxyethylcarbamoyl)-1,2,3,4-tetrahydropyrimidine-5-carboxylic acid:

The title compound was obtained in the same manner as that of Example 20.

MS (ESI, m/z) 428 (M−H)−.

$^1$H-NMR (DMSO-d6): 2.28 (3H, s), 3.58–3.36 (2H, m), 4.04 (2H, q), 6.53 (1H, s), 6.90–6.94 (3H, m), 7.14–7.38 (6H, m), 9.03 (1H, t), 10.07 (1H, s).

EXAMPLE 33

Synthesis of 4-(3-chlorophenyl)-3-[2-(methoxyphenyl)ethylcarbamoyl]-6-methyl-2-oxo-1,2,3,4-tetrahydro-pyrimidine-5-carboxylic acid The title compound was obtained in the same manner as that of Example 20.

MS (ESI, m/z) 442 (M−H)−.

$^1$H-NMR (DMSO-d6): 2.26 (3H, s), 2.75 (2H, t), 6.51 (1H, s), 6.83 (1H, t), 6.93 (1H, d), 7.07–7.39 (6H, m), 8.77 (1H, t), 9.97 (1H, s).

EXAMPLE 34

Synthesis of ethyl [6-(3-chlorophenyl)-5-(3,3-diphenylpropylcarbamoyl)-4-methyl-2-oxo-3,6-dihydro-2H-pyrimidine-1-yl]acetate 1) Synthesis of 5-benzyl 6-(3-chlorophenyl)-1-ethoxycarbonylmethyl-2-methoxy-4-methyl-6H-pyrimidine-5-carboxylate:

500 mg (1.35 mmol) of benzyl 4-(3-chlorophenyl)-2-methoxy-6-methyl-1,4-dihydropyrimidine-5-carboxylate was dissolved in 5 ml of DMF. 108 mg (2.70 mmol) of sodium hydride (60% oily) was added to the obtained solution under cooling with ice, and they were stirred for 30 minutes. 248 mg (2.02 mmol) of ethyl chloroacetate was added to the reaction mixture at 0° C., and they were stirred for 12 hours while the temperature was elevated to room temperature. After the concentration under reduced pressure, the reaction mixture was diluted with ethyl acetate, washed with water and saturated aqueous sodium chloride solution and concentrated under reduced pressure. The residue was purified by the silica gel chromatography (hexane/ethyl acetate=10/1 to 1/1) to obtain the title compound.

Yield: 219 mg (0.479 mmol) (35.5%).

MS (ESI, m/z) 457 (M+H)+.

$^1$H-NMR (CDCl3): 1.20 (3H, t), 2.41 (3H, s), 3.65 (1H, d), 3.87 (3H, s), 4.04–4.12 (3H, m), 5.02 (2H, dd), 5.27 (1H, s), 7.11–7.38 (9H, m).

2) Synthesis of benzyl 4-(3-chlorophenyl)-3-ethoxycarbonylmethyl-6-methyl-2-oxo-1,2,3,4-tetrahydropyrimidine-5-carboxylate:

219 mg (0.479 mmol) of 5-benzyl 6-(3-chlorophenyl)-1-ethoxycarbonylmethyl-2-methoxy-4-methyl-6H-pyrimidine-5-carboxylate was dissolved in 5 ml methanol/5 ml THF. 3 N hydrochloric acid was added to the obtained solution, and they were stirred at room temperature for 1 hour. After the concentration under reduced pressure, the reaction mixture was diluted with ethyl acetate, washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (100% dichloromethane) to obtain the crude title compound.

Yield: 176 mg (0.396 mmol) (82.7%).

MS (ESI, m/z) 443 (M+H)+.

$^1$H-NMR (CDCl3): 1.23 (3H, t), 2.36 (3H, s), 3.46 (1H, d), 4.15 (2H, tt), 4.41 (1H, d), 5.05 (2H, dd), 5.28 (1H, s), 7.12–7.34 (9H, m), 8.47 (1H, s).

3) Synthesis of 4-(3-chlorophenyl)-3-ethoxycarbonylmethyl-6-methyl-2-oxo-1,2,3,4-tetrahydropyrimidine-5-carboxylic acid:

10 ml of ethyl acetate was added to a mixture of 130 mg (0.293 mmol) of benzyl 4-(3-chlorophenyl)-3-ethoxycarbonylmethyl-6-methyl-2-oxo-1,2,3,4-tetrahydropyrimidine-5-carboxylate and a catalytic amount of 10% palladium/carbon, and they were stirred at room temperature in hydrogen atmosphere under normal pressure for 2 days. The catalyst was filtered out, and the obtained filtrate was concentrated under reduced pressure to obtain the title compound.

Yield: 111 mg (0.315 mmol) (quantitative yield).

MS (ESI, m/z) 353 (M+H)+.

$^1$H-NMR (CDCl3): 1.25 (3H, t), 2.36 (3H, s), 3.49 (1H, d), 4.11–4.22 (2H, m), 4.46 (1H, d), 5.29 (1H, s), 7.20–7.33 (4H, m), 8.90 (1H, s).

4) Synthesis of ethyl [6-(3-chlorophenyl)-5-(3,3-diphenylpropylcarbamoyl)-4-methyl-2-oxo-3,6-dihydro-2H-pyrimidine-1-yl]acetate:

109 mg (0.309 mmol) of 4-(3-chlorophenyl)-3-ethoxycarbonylmethyl-6-methyl-2-oxo-1,2,3,4-tetrahydropyrimidine-5-carboxylic acid and 97.9 mg (0.463 mmol) of 3,3-diphenylpropylamine were dissolved in 20 ml of dichloromethane. 88.8 mg (0.463 mmol) of WSC hydrochloride was added to the obtained solution under cooling with ice, and they were stirred at room temperature overnight. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was washed with hexane/ethyl acetate (1/1) and then dried under reduced pressure to obtain the title compound.

Yield: 164 mg (0.301 mmol) (97.4%).

MS (ESI, m/z) 546 (M+H)+.

$^1$H-NMR (CDCl3): 1.24 (3H, t), 2.05 (3H, s), 2.06–2.16 (2H, m), 3.02–3.28 (2H, m), 3.49 (1H, d), 3.74 (1H, t), 4.09–4.20 (2H, m), 4.42 (1H, d), 5.15 (1H, t), 5.23 (1H, s), 7.11–7.28 (14H, m), 8.36 (1H, br).

EXAMPLE 35

Synthesis of [6-(3-chlorophenyl)-5-(3,3-diphenylpropylcarbamoyl)-4-methyl-2-oxo-3,6-dihydro-2H-pyrimidine-1-yl]acetic acid 59.7 mg (0.109 mmol) of ethyl [6-(3-chlorophenyl)-5-(3,3-diphenylpropylcarbamoyl)-4-methyl-2-oxo-3,6-dihydro-2H-pyrimidine-1-yl]acetate was dissolved in 10 ml of methanol. 0.219 ml of 1 N aqueous sodium hydroxide solution was added to the obtained solution at room temperature, and they were stirred for 12 hours. 1 N hydrochloric acid was added to the reaction mixture. Methanol was evaporated under reduced pressure. Water was added to the residue, and precipitates thus formed were taken by the filtration, then washed with hexane/ethyl acetate (3/1) and dried under reduced pressure to obtain the title compound.

Yield: 43.5 mg (0.0840 mmol) (77.0%).

MS (ESI, m/z) 518 (M+H)+.

$^1$H-NMR (CDCl3): 1.99–2.05 (5H, m), 2.82–2.94 (2H, m), 3.04 (1H, d), 3.77 (1H, t), 4.15 (1H, d), 5.41 (1H, s), 7.11–7.34 (14H, m), 7.59 (1H, t), 8.74 (1H, s).

EXAMPLE 36

Synthesis of benzyl 4-(3-chlorophenyl)-6-methyl-2-oxo-3-(2-pyridine-4-yl-ethylcarbamoyl) 1,2,3,4-tetrahydropyrimidine-5-carboxylate The title compound was obtained in the same manner as that of Example 19.

MS (ESI, m/z) 505 (M+H)+.

$^1$H-NMR (CDCl3): 2.40 (3H, s), 2.78–2.90 (2H, m), 3.55 (2H, dd), 5.15 (2H, dd), 6.70 (1H, s), 6.80 (1H, br), 7.07–7.09 (2H, m), 7.16–7.19 (2H, m), 7.21–7.34 (7H, m), 8.48–8.50 (2H, m), 8.82 (1H, t).

EXAMPLE 37

Synthesis of 4-(3-chlorophenyl)-6-methyl-2-oxo-3-(2-pyridine-4-yl-ethylcarbamoyl)-1,2,3,4-tetrahydropyrimidine-5-carboxylic acid The title compound was obtained in the same manner as that of Example 20.

MS (ESI, m/z) 415 (M+H)+.

$^1$H-NMR (CD3OD): 2.28 (3H, s), 2.81–2.96 (2H, m), 3.47–3.66 (2H, m), 6.68 (1H, s), 7.19–7.31 (6H, m), 8.38 (2H, d), 9.20 (1H, t).

EXAMPLE 38

Synthesis of benzyl 4-(3-chlorophenyl)-3-[2-(4-methoxyphenyl)-ethylcarbamoyl]-6-methyl-2-oxo-1,2,3,4-tetrahydropyrimidine-5-carboxylate The title compound was obtained in the same manner as that of Example 19.

MS (ESI, m/z) 534 (M+H)+.

$^1$H-NMR (CDCl3): 2.30 (3H, s), 2.70–2.82 (2H, m), 3.50 (2H, dd), 3.73 (3H, s), 5.15 (2H, dd), 6.73 (1H, s), 6.79 (2H, d), 7.06 (2H, d), 7.16–7.34 (9H, m), 7.58 (1H, s), 8.71 (1H, t).

EXAMPLE 39

Synthesis of 4-(3-chlorophenyl)-3-[2-(4-methoxyphenyl)ethylcarbamoyl]-6-methyl-2-oxo-1,2,3,4-tetrahydropyrimidine-5-carboxylic acid The title compound was obtained in the same manner as that of Example 20.

MS (ESI, m/z) 444 (M+H)+.

$^1$H-NMR (DMSO-d6): 2.26 (3H, s), 2.65–2.71 (2H, m), 3.37 (2H, dd), 3.69 (3H, s), 6.50 (1H, s), 6.81 (2H, d), 7.07–7.16 (4H, m), 7.31–7.39 (2H, m), 8.79 (1H, t), 10.00 (1H, s).

EXAMPLE 40

Synthesis of benzyl 4-(3-chlorophenyl)-6-methyl-2-oxo-3-(3-phenyl-2-propene-1-ylcarbamoyl)-1,2,3,4-tetrahydropyrimidine-5-carboxylate The title compound was obtained in the same manner as that of Example 19.

MS (ESI, m/z) 514 (M-H)-.

$^1$H-NMR (CDCl3): 2.39 (3H, s), 4.00–4.08 (2H, m), 5.15 (2H, ABq), 6.14–6.23 (1H, m), 6.50 (1H, d), 6.75 (1H, s), 7.08 (1H, s), 7.14–7.34 (14H, m), 8.88 (1H, t).

EXAMPLE 41

Synthesis of ethyl 6-(3-chlorophenyl)-4-methyl-2-oxo-5-(3-phenyl-2-propene-1-ylcarbamoyl)-3,6-dihydro-2H-pyrimidine-1-carboxylate The title compound was obtained in the same manner as that of Example 24.

MS (ESI, m/z) 452 (M-H)-.

$^1$H-NMR (DMSO-d6): 1.21 (3H, t), 2.09 (3H, s), 3.89–3.93 (2H, m), 4.17–4.25 (2H, m), 6.03 (1H, s), 6.19–6.26 (1H, m), 6.35 (1H, d), 7.18–7.42 (9H, m), 8.18 (1H, t), 9.67 (1H, s).

EXAMPLE 42

Synthesis of 3-carbamoyl-4-(3-chlorophenyl)-6-methyl-2-oxo-1,2,3,4-tetrahydropyrimidine-5-carboxylic acid (3-phenyl-2-propene-1-yl)amide The title compound was obtained in the same manner as that of Example 21.

MS (ESI, m/z) 423 (M-H)-.

$^1$H-NMR (DMSO-d6): 2.08 (3H, s), 3.90 (2H, brs), 6.16–6.25 (1H, m), 6.33 (1H, d), 6.41 (1H, s), 7.19–7.38 (9H, m), 7.46 (1H, brs), 8.14 (1H, t), 8.23 (1H, brs), 9.63 (1H, s).

EXAMPLE 43

Synthesis of 4-(3-chlorophenyl)-6-methyl-2-oxo-3-(3-phenyl-2-propene-1-ylcarbamoyl)-1,2,3,4-tetrahydropyrimidine-5-carboxylic acid The title compound was obtained in the same manner as that of Example 20.

MS (ESI, m/z) 424 (M-H)-.

$^1$H-NMR (DMSO-d6): 2.28 (3H, s), 2.48–2.50 (2H, m), 6.51 (1H, s), 7.15–7.36 (11H, m), 8.83 (1H, t), 10.00 (1H, s).

EXAMPLE 44

Synthesis of ethyl 6-(3-chlorophenyl)-4-methyl-2-oxo-5-(pyridine-4-ylethylcarbamoyl)-3,6-dihydro-2H-pyrimidine-1-carboxylate The title compound was obtained in the same manner as that of Example 24.

MS (ESI, m/z) 443 (M+H)+, 441 (M-H)-.

$^1$H-NMR (DMSO-d6): 1.21 (3H, t), 1.92 (3H, s), 2.76 (2H, t), 3.38 (2H, q), 4.15–4.26 (2H, m), 5.93 (1H, s), 7.11–7.16 (3H, m), 7.19 (1H, s), 7.36 (2H, q), 7.96 (1H, t), 8.38 (2H, dd), 9.62 (1H, s).

EXAMPLE 45

Synthesis of ethyl [6-(3-chlorophenyl)-4-methyl-2-oxo-5-(3-phenyl-2-propene-1-ylcarbamoyl)-3,6-dihydro-2H-pyrimidine-1-yl]acetate The title compound was obtained in the same manner as that of Example 34.

MS (ESI, m/z) 468 (M+H)+, 466 (M-H)-.

$^1$H-NMR (DMSO-d6): 1.11 (3H, t), 2.03 (3H, s), 3.63 (1H, d), 3.74–3.83 (2H, m), 3.95–4.10 (3H, m), 5.38 (1H, s), 6.00–6.17 (2H, m), 7.17–7.32 (9H, m), 7.82 (1H, t), 8.93 (1H, s).

EXAMPLE 46

Synthesis of ethyl [6-(3-chlorophenyl)-4-methyl-2-oxo-5-(4-pyridine-4-ylethylcarbamoyl)-3,6-dihydro-2H-pyrimidine-1-yl]acetate The title compound was obtained in the same manner as that of Example 34.

MS (ESI, m/z) 457 (M+H)+, 455 (M-H)-.

¹H-NMR (DMSO-d6): 1.11 (3H, t), 1.87 (3H, s), 2.58–2.64 (2H, m), 3.23–3.30 (1H, m), 3.57 (1H, d), 3.95–4.12 (4H, m), 5.30 (1H, s), 7.01 (2H, t), 7.13–7.17 (1H, m), 7.23 (1H, s), 7.32–7.34 (2H, m), 7.63 (1H, t), 8.35–8.37 (2H, m), 8.88 (1H, s).

EXAMPLE 47

Synthesis of [6-(3-chlorophenyl)-4-methyl-2-oxo-5-(3-phenyl-2-propene-1-ylcarbamoyl)-3,6-dihydro-2H-pyrimidine-1-yl]acetic acid The title compound was obtained in the same manner as that of Example 35.

MS (ESI, m/z) 438 (M–H)–.

¹H-NMR (DMSO-d6): 2.05 (1H, s), 3.39 (1H, s), 3.80 (2H, q), 4.11 (1H, d), 5.40 (1H, s), 6.01–6.09 (1H, m), 6.15 (1H, d), 7.18–7.39 (9H, m), 7.82 (1H, t), 8.92 (1H, s).

EXAMPLE 48

Synthesis of [6-(3-chlorophenyl)-4-methyl-2-oxo-5-(4-pyridine-4-ylethylcarbamoyl)-3,6-dihydro-2H-pyrimidine-1-yl]acetic acid The title compound was obtained in the same manner as that of Example 35.

MS (ESI, m/z) 429 (M+H)+, 427 (M–H)–.

¹H-NMR (DMSO-d6): 1.88 (3H, s), 2.61–2.68 (2H, m), 2.70 (1H, s), 3.27–3.30 (2H, m), 4.13 (1H, d), 5.43 (1H, s), 7.07–7.14 (4H, m), 7.30–7.32 (2H, m), 7.67 (1H, t), 8.38 (2H, d), 8.56 (1H, s).

EXAMPLE 49

Synthesis of benzyl 4-(3-chlorophenyl)-6-methyl-2-oxo-3-(2-pyridine-3-yl-ethylcarbamoyl)-1,2,3,4-tetrahydropyrimidine-5-carboxylate The title compound was obtained in the same manner as that of Example 19.

MS (ESI, m/z) 505 (M+H)+.

¹H-NMR (CDCl3): 2.36 (3H, s), 2.81–2.85 (2H, m), 3.48–3.58 (2H, m), 5.14 (2H, dd), 6.69 (1H, s), 7.15–7.32 (10H, m), 7.48 (1H, dt), 8.03 (1H, s), 8.43–8.45 (2H, m), 8.85 (1H, t).

EXAMPLE 50

Synthesis of 4-(3-chlorophenyl)-6-methyl-2-oxo-3-(2-pyridine-3-yl-ethylcarbamoyl)-1,2,3,4-tetrahydropyrimidine-5-carboxylic acid The title compound was obtained in the same manner as that of Example 20.

MS (ESI, m/z) 415 (M+H)+.

¹H-NMR (DMSO-d6): 2.47 (3H, s), 2.76–2.80 (2H, m), 3.45 (2H, dd), 6.48 (1H, s), 7.09–7.15 (2H, m), 7.25–7.39 (3H, m), 7.59 (1H, dd), 8.38–8.40 (2H, m), 8.82 (1H, t), 10.01 (1H, s).

EXAMPLE 51

Synthesis of 3-(4-benzhydrylpiperazine-1-carbonyl)-4-(3-chlorophenyl)-6-methyl-2-oxo-1,2,3,4-tetrahydropyrimidine-5-carboxylic acid The title compound was obtained in the same manner as that of Example 20.

MS (ESI, m/z) 545 (M+H)+.

¹H-NMR (DMSO-d6): 2.22 (3H, s), 3.32 (8H, br), 4.25 (1H, br), 5.57 (1H, br s), 7.19–7.41 (14H, m), 9.73 (1H, br s).

EXAMPLE 52

Synthesis of methyl [[4-(3-chlorophenyl)-6-methyl-2-oxo-1,2,3,4-tetrahydropyrimidine-5-carbonyl]-(3-phenyl-2-propene-1-yl)-amino]acetate 1) Synthesis of methyl (3-phenyl-2-propene-1-ylamino) acetate:

2.00 g (15.9 mmol) of methyl aminoacetate hydrochloride was dissolved in 100 ml of acetonitrile. 4.40 g (31.8 mmol) of potassium carbonate and 3.10 g (15.9 mmol) of cinnamyl bromide were added to the obtained solution, and they were stirred at 60° C. for 4 hours. After the extraction with ethyl acetate, the extract was dried over magnesium sulfate. Ethyl acetate was evaporated under reduced pressure. The residue was purified by the silica gel chromatography (hexane/ethyl acetate=1/1 to 1/3) to obtain the title compound.

Yield: 280 mg (1.20 mmol) (7.5%).

¹H-NMR (CDCl3): 1.27 (3H, s), 3.36–3.44 (4H, m), 6.20–6.29 (1H, m), 6.53 (1H, d), 7.19–7.38 (5H, m).

2) Synthesis of methyl [[4-(3-chlorophenyl)-6-methyl-2-oxo-1,2,3,4-tetrahydropyrimidine-5-carbonyl]-(3-phenyl-2-propene-1-yl)-amino]acetate:

320 mg (1.20 mmol) of 4-(3-chlorophenyl)-6-methyl-2-oxo-1,2,3,4-tetrahydropyrimidine-5-carboxylic acid was dissolved in 2 ml of DMF. 280 mg (1.20 mmol) of methyl (3-phenyl-2-propene-1-ylamino)acetate and 276 mg (1.44 mmol) of WSC hydrochloride were added to the obtained solution, and they were stirred at room temperature overnight. After the extraction with ethyl acetate, the extract was dried over magnesium sulfate. Ethyl acetate was evaporated under reduced pressure. The residue was purified by the silica gel chromatography (methylene chloride/methanol= 200/1 to 50/1) to obtain the title compound.

Yield: 250 mg (0.550 mmol) (45.8%).

MS (ESI, m/z) 452 (M–H)–.

¹H-NMR (DMSO-d6): 1.82 (3H, s), 3.33 (3H, s), 3.85 (2H, brs), 4.02 (2H, brs), 5.05 (1H, brs), 6.40 (1H, d), 7.20–7.39 (9H, m), 7.48 (1H, s), 8.67 (1H, s).

EXAMPLE 53

Synthesis of [[4-(3-chlorophenyl)-6-methyl-2-oxo-1,2,3,4-tetrahydropyrimidine-5-carbonyl]-(3-phenyl-2-propene-1-yl)-amino]acetic acid 100 mg (0.220 mmol) of methyl [[4-(3-chlorophenyl)-6-methyl-2-oxo-1,2,3,4-tetrahydropyrimidine-5-carbonyl]-(3-phenyl-2-propene-1-yl)-amino]acetate was dissolved in 2 ml of methanol. 0.480 ml of 1 N aqueous sodium hydroxide solution was added to the obtained solution, and they were stirred at room temperature overnight. The solvent was evaporated under reduced pressure, and the residue was washed with water. After the slurry washing, the title compound was obtained.

Yield: 66.0 mg (0.140 mmol) (63.6%).

MS (ESI, m/z) 438 (M–H)–.

¹H-NMR (DMSO-d6): 1.78 (3H, s), 3.71 (2H, brs), 4.00 (2H, brs), 5.05 (1H, s), 6.38 (1H, d), 7.21–7.38 (9H, m), 7.46 (1H, s), 8.64 (1H, s).

EXAMPLE 54

Synthesis of 4-(3-chlorophenyl)-6-methyl-2-oxo-1,2,3,4-tetrahydropyrimidine-5-carboxylic acid (4-phenylbutyl)amide The title compound was obtained in the same manner as that of Example 3.

MS (ESI, m/z) 396 (M–H)–.
$^1$H-NMR (CDCl3): 1.36–1.43 (4H, m), 2.53 (2H, t), 3.11–3.24 (2H, m), 5.33 (1H, s), 5.37 (1H, s), 6.20 (1H, s), 7.08–7.28 (9H, m), 8.13 (1H, s).

EXAMPLE 55

Synthesis of benzyl 4-(3-chlorophenyl)-6-methyl-2-oxo-3-(4-phenylbutylcarbamoyl)-1,2,3,4-tetrahydropyrimidine-5-carboxylate The title compound was obtained in the same manner as that of Example 19.

MS (ESI, m/z) 530 (M–H)–.
$^1$H-NMR (CDCl3): 1.52–1.69 (5H, m), 2.38 (3H, s), 2.61 (2H, t), 3.21–3.37 (2H, m), 5.15 (2H, ABq), 6.73 (1H, s), 7.03 (1H, s), 7.12–7.35 (9H, m), 8.69 (1H, t).

EXAMPLE 56

Synthesis of 4-(3-chlorophenyl)-6-methyl-2-oxo-3-(4-phenylbutylcarbamoyl)-1,2,3,4-tetrahydropyrimidine-5-carboxylic acid The title compound was obtained in the same manner as that of Example 20.

MS (ESI, m/z) 440 (M–H)–.
$^1$H-NMR (DMSO-d6): 1.47–1.58 (4H, m), 2.50 (3H, d), 2.57 (2H, t), 3.22 (2H, q), 6.53 (1H, s), 7.13–7.36 (9H, m), 8.81 (1H, t), 9.97 (1H, s).

EXAMPLE 57

Synthesis of 2-amino-4-(3-chlorophenyl)-6-methyl-1,4-dihydropyrimidine-5-carboxylic acid (3,3-diphenylpropyl)amide 1) Synthesis of 4-(3-chlorophenyl)-2-methoxy-6-methyl-1,4-dihydropyrimidine-5-carboxylic acid:

10 ml of ethyl acetate was added to a mixture of 460 mg (1.24 mmol) of benzyl 4-(3-chlorophenyl)-2-methoxy-6-methyl-1,4-dihydropyrimidine-5-carboxylate and a catalytic amount of 10% palladium/carbon, and they were stirred at room temperature in hydrogen atmosphere under normal pressure for 2 days. The catalyst was filtered out, and the filtrate was concentrated under reduced pressure to obtain the title compound.

Yield: 343 mg (1.22 mmol) (quantitative yield).
MS (ESI, m/z) 443 (M+H)+.
$^1$H-NMR (CDCl3): 2.35 (3H, s), 3.75 (3H, s), 5.50 (1H, s), 7.16–7.37 (4H, m).

2) Synthesis of 4-(3-chlorophenyl)-2-methoxyl-6-methyl-1,4-dihydropyrimidine-5-carboxylic acid (3,3-diphenylpropyl)amide:

158 mg (0.563 mmol) of 4-(3-chlorophenyl)-2-methoxy-6-methyl-1,4-dihydropyrimidine-5-carboxylic acid and 178 mg (0.844 mmol) of 3,3-diphenylpropylamine were dissolved in 20 ml of dichloromethane. 162 mg (0.844 mmol) of WSC hydrochloride was added to the obtained solution under cooling with ice, and they were stirred at room temperature overnight. After the concentration under reduced pressure, the reaction mixture was diluted with ethyl acetate and then washed with saturated aqueous sodium chloride solution. The organic layer was dried over anhydrous magnesium sulfate and then concentrated under reduced pressure. The residue was purified by the silica gel chromatography (hexane/ethyl acetate=2/1) to obtain the title compound.

Yield: 111 mg (0.234 mmol) (41.6%).
MS (ESI, m/z) 474 (M+H)+.
$^1$H-NMR (CDCl3): 2.09–2.14 (5H, m), 3.05–3.23 (2H, m), 3.68–3.73 (4H, m), 5.15 (1H, br), 5.37 (1H, br), 5.84 (1H, br), 7.08–7.34 (14H, m).

3) Synthesis of 2-amino-4-(3-chlorophenyl)-6-methyl-1,4-dihydropyrimidine-5-carboxylic acid (3,3-diphenylpropyl)amide:

111 mg (0.234 mmol) of 4-(3-chlorophenyl)-2-methoxyl-6-methyl-1,4-dihydropyrimidine-5-carboxylic acid (3,3-diphenylpropyl)amide was dissolved in 5 ml of ethanol. 67.4 mg (0.702 mmol) of ammonium carbonate and 11.8 mg (0.187 mmol) of ammonium acetate were added to the obtained solution, and they were stirred at 80° C. for 2 days. The reaction mixture was diluted with ethyl acetate. An insoluble matter thus formed was filtered out, and the filtrate was concentrated under reduced pressure. The residue was purified by the basic silica gel chromatography (100% dichloromethane) to obtain the title compound.

Yield: 35.0 mg (0.0758 mmol) (32.4%).
MS (ESI, m/z) 460 (M+H)+.
$^1$H-NMR (CDCl3): 2.03–2.15 (5H, m), 3.01–3.12 (1H, m), 3.16–3.28 (1H, m), 3.70 (1H, t), 5.14 (1H, t), 5.26 (1H, s), 5.85 (1H, br), 7.09–7.30 (14H, m), 7.71 (1H, br).

EXAMPLE 58

Synthesis of 4-(3-chlorophenyl)-6-methyl-2-methylsulfanyl-1,4-dihydropyrimidine-5-carboxylic acid (3-phenyl-2-propene-1-yl)amide 1) Synthesis of 3-oxo-N-(3-phenyl-2-propene-1-yl)butyramide:

3.06 g (23.0 mmol) of cinnamylamine, 2.32 ml (30.1 mmol) of ketene dimer and 0.321 ml (2.30 mmol) of triethylamine were stirred in 23 ml of toluene under heating at 70° C. for 3 hours. Saturated aqueous sodium hydrogencarbonate solution was added to the reaction mixture. After the extraction with ethyl acetate, the organic layer was dried over anhydrous sodium sulfate and then concentrated under reduced pressure to obtain the title compound.

Yield: 5.08 g (23.4 mmol) (quantitative yield).
MS (ESI, m/z) 216 (M–H)–.
$^1$H-NMR (CDCl3): 2.29 (3H, s), 3.47 (2H, s), 4.07 (2H, t), 6.20 (1H, dt), 6.54 (1H, d), 7.15–7.40 (5H, m).

2) Synthesis of 3-acetyl-3-(3-chlorophenyl)-N-(3-phenyl-2-propene-1-yl)acrylamide:

300 mg (1.38 mmol) of 3-oxo-N-(3-phenyl-2-propene-1-yl)butyramide and 194 mg (1.38 mmol) of 3-chlorobenzaldehyde were dissolved in 20 ml of 2-propanol. 4.14 mg (0.0690 mmol) of piperidine and 5.67 mg (0.0690 mmol) of acetic acid were added to the obtained solution, and they were stirred at room temperature for 2 days. The solvent was evaporated under reduced pressure. Ethyl acetate was added to the residue. The obtained mixture was washed with 1 N hydrochloric acid and then with saturated aqueous sodium hydrogencarbonate solution. The organic layer was dried over anhydrous magnesium sulfate and then concentrated under reduced pressure. The residue was purified by the silica gel chromatography (hexane/ethyl acetate=10/1) to obtain the title compound.

Yield: 413 mg (1.21 mmol) (88.0%).
MS (ESI, m/z) 340 (M+H)+.
$^1$H-NMR (CDCl3): 2.43 (3H, s), 4.10–4.16 (2H, m), 6.05–6.17 (2H, m), 6.70 (1H, d), 7.22–7.32 (7H, m), 7.41–7.45 (2H, m), 7.52 (1H, s).

3) Synthesis of 4-(3-chlorophenyl)-6-methyl-2-methylsulfanyl-1,4-dihydro-pyrimidine-5-carboxylic acid (3-phenyl-2-propene-1-yl)amide:

120 mg (0.353 mmol) of 3-acetyl-3-(3-chlorophenyl)-N-(3-phenyl-2-propene-1-yl)acrylamide was dissolved in 10 ml of DMF. 78.6 mg (0.283 mmol) of methylisothiourea monosulfate and 34.7 mg (0.424 mmol) of sodium acetate were added to the obtained solution at room temperature, and they were stirred at that temperature overnight. DMF was evaporated under reduced pressure. The residue was diluted with ethyl acetate and washed with saturated aqueous sodium chloride solution. The organic layer was dried over anhydrous magnesium sulfate and then concentrated under reduced pressure. 2-propanol was added to the residue, and they were heated to 120° C. and stirred overnight. The residue was purified by the silica gel chromatography (hexane/ethyl acetate=5/1) to obtain the title compound.

Yield: 58.0 mg (0.141 mmol) (39.8%).

MS (ESI, m/z) 412 (M+H)+.

$^1$H-NMR (CDCl3): 2.24 (3H, s), 2.40 (3H, s), 3.92–4.04 (2H, m), 5.39 (1H, br), 5.50 (1H, s), 6.06 (1H, dt), 6.32 (2H, d), 7.21–7.33 (9H, m).

EXAMPLE 59

Synthesis of 4-(3-chlorophenyl)-6-methyl-2-methylsulfanyl-1,4-dihydropyrimidine-5-carboxylic acid (3,3-diphenylpropyl)amide The title compound was obtained in the same manner as that of Example 58.

MS (ESI, m/z) 490 (M+H)+.

$^1$H-NMR (CDCl3): 2.15 (5H, br), 2.37 (2H, br), 3.08–3.25 (2H, m), 3.73 (1H, t), 5.20 (1H, br), 5.40 (1H, s), 6.30 (1H, br), 7.09–7.33 (14H, m).

EXAMPLE 60

Synthesis of 4-(3,4-dichlorophenyl)-6-methyl-2-phenyl-1,4-dihydropyrimidine-5-carboxylic acid (3-phenylpropyl)amide 1) Synthesis of 2-acetyl-3-(3,4-dichlorophenyl)-N-(3-phenylpropyl)acrylamide:

1.75 g (8.00 mmol) of 3-oxo-N-(3-phenylpropyl) butyramide was dissolved in 20 ml of benzene. 1.40 g (8.00 mmol) of 3,4-dichlorobenzaldehyde and 0.08 ml (0.80 mmol) of piperidine were added to the obtained solution, and they were stirred at 110° C. for 2 hours. After the concentration under reduced pressure, the reaction mixture was diluted with ethyl acetate and then washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (hexane/ethyl acetate=3/1) to obtain the title compound.

Yield: 1.87 mg (4.69 mmol) (62.0%).

$^1$H-NMR (CDCl3): 1.82–1.92 (2H, m), 2.42 (3H, s), 2.62 (2H, t), 3.36–3.43 (2H, m), 5.80 (1H, s), 7.11–7.29 (6H, m), 7.35–7.45 (3H, m), 7.62 (1H, d).

2) Synthesis of 4-(3,4-dichlorophenyl)-6-methyl-2-phenyl-1,4-dihydropyrimidine-5-carboxylic acid (3-phenylpropyl) amide:

100 mg (0.266 mmol) of 2-acetyl-3-(3,4-dichlorophenyl)-N-(3-phenylpropyl)acrylamide was dissolved in 2 ml of DMF. 63.0 mg (0.400 mmol) of benzamidine hydrochloride and 26.0 mg (0.317 mmol) of sodium acetate were added to the obtained solution, and they were stirred at 60° C. overnight. Ethyl acetate was added to the reaction mixture and then the obtained mixture was washed with 1 N hydrochloric acid, saturated aqueous sodium hydrogencarbonate solution and saturated aqueous sodium chloride solution. The organic layer was dried over anhydrous magnesium sulfate and then concentrated under reduced pressure. The residue was purified by the silica gel chromatography (hexane/ethyl acetate=1/3) to obtain the title compound.

Yield: 41.0 mg (0.086 mmol) (32.0%).

MS (ESI, m/z) 478 (M+H)+, 476 (M−H)−.

$^1$H-NMR (CDCl3): 1.72–1.82 (2H, m), 2.31 (2H, t), 2.54 (2H, t), 3.20–3.32 (2H, m), 5.35 (1H, s), 5.59 (1H, s), 7.09 (2H, d), 7.19–7.30 (4H, m), 7.40–7.50 (4H, m), 7.68 (2H, d), 8.01 (1H, s).

EXAMPLE 61

Synthesis of 4-(3,4-dichlorophenyl)-6-methyl-2-pyridine-3-yl-1,4-dihydropyrimidine-5-carboxylic acid (3-phenylpropyl)amide The title compound was obtained in the same manner as that of Example 60.

MS (ESI, m/z) 479 (M+H)+, 477 (M−H)−.

$^1$H-NMR (DMSO-d6): 1.59–1.69 (2H, m), 2.14 (3H, s), 3.02–3.15 (2H, m), 3.17 (2H, t), 5.68 (1H, s), 7.08–7.32 (5H, m), 7.45–7.50 (2H, m), 7.57 (1H, d), 7.75 (1H, s), 8.16–8.20 (1H, m), 8.67 (1H, dd), 9.00 (1H, s), 9.18 (1H, s).

EXAMPLE 62

Synthesis of 4-(3,4-dichlorophenyl)-2,6-dimethyl-1,4-dihydropyrimidine-5-carboxylic acid (3-phenylpropyl)amide The title compound was obtained in the same manner as that of Example 60.

MS (ESI, m/z) 414 (M+H)+.

$^1$H-NMR (DMSO-d6): 1.59 (2H, t), 2.02 (3H, s), 2.38 (2H, t), 3.03 (2H, t), 7.03–7.27 (6H, m), 7.49 (1H, s), 7.58 (1H, d), 7.96 (1H, s).

EXAMPLE 63

Synthesis of 4-(3,4-dichlorophenyl)-6-methyl-2-phenyl-1,4-dihydropyrimidine-5-carboxylic acid (3, 3-diphenylpropyl)amide The title compound was obtained in the same manner as that of Example 60.

MS (ESI, m/z) 554 (M+H)+, 552 (M−H)−.

$^1$H-NMR (CDCl3): 2.16–2.22 (2H, m), 2.27 (3H, s), 3.15–3.26 (2H, m), 3.78 (1H, t), 5.29 (1H, s), 5.54 (1H, s), 7.12–7.19 (5H, m), 7.24–7.29 (5H, m), 7.41–7.51 (5H, m), 7.66 (2H, d), 8.00 (1H, s).

EXAMPLE 64

Synthesis of 4-(3,4-dichlorophenyl)-6-methyl-2-pyridine-3-yl-1,4-dihydropyrimidine-5-carboxylic acid (3,3-diphenylpropyl)amide The title compound was obtained in the same manner as that of Example 60.

MS (ESI, m/z) 555 (M+H)+, 553 (M−H)−.

$^1$H-NMR (DMSO-d6): 2.06–2.14 (2H, m), 2.15 (3H, s), 2.89–3.04 (2H, m), 3.82 (1H, t), 5.69 (1H, s), 7.13–7.32 (10H,m), 7.45–7.50 (2H, m), 7.57 (1H, s), 8.17 (1H, d), 8.67 (1H, d), 9.00 (1H, s), 9.18 (1H, s).

EXAMPLE 65

Synthesis of 4-(3,4-dichlorophenyl)-2,6-dimethyl-1,4-dihydropyrimidine-5-carboxylic acid (3,3-diphenylpropyl)amide The title compound was obtained in the same manner as that of Example 60.

MS (ESI, m/z) 492 (M+H)+, 490 (M–H)–.

$^1$H-NMR (DMSO-d6): 1.98–2.04 (2H, m), 2.06 (3H, s), 2.17 (3H, s), 2.83–2.92 (2H, m), 3.72 (1H, t), 5.75 (1H, s), 7.10–7.18 (5H, m), 7.20–7.29 (5H, m), 7.37 (1H, dd), 7.64 (1H, s), 7.65 (1H, d), 8.11 (1H, s).

EXAMPLE 66

Synthesis of 4-(3-chlorophenyl)-6-methyl-2-pyridine-3-yl-1,4-dihydropyrimidine-5-carboxylic acid (3,3-diphenylpropyl)amide The title compound was obtained in the same manner as that of Example 58.

MS (ESI, m/z) 521 (M+H)+.

$^1$H-NMR (CDCl3): 2.10–2.20 (2H, m), 2.27 (3H, br), 3.10–3.18 (2H, m), 3.73 (1H, t), 5.26 (1H, br), 5.55 (1H, s), 7.09–7.35 (14H, m), 7.39 (1H, s), 8.02 (1H, d), 8.66 (1H, d), 8.88 (1H, t).

EXAMPLE 67

Synthesis of 4-(3-chlorophenyl)-6-methyl-2-phenyl-1,4-dihydro-pyrimidine-5-carboxylic acid (3,3-diphenylpropyl)amide The title compound was obtained in the same manner as that of Example 58.

MS (ESI, m/z) 520 (M+H)+.

$^1$H-NMR (CDCl3): 2.12–2.20 (2H, m), 2.28 (3H, s), 3.10–3.21 (2H, m), 3.74 (1H, t), 5.26 (1H, br), 5.54 (1H, s), 7.10–7.30 (13H, m), 7.37–7.46 (4H, m), 7.67 (2H, d).

EXAMPLE 68

Synthesis of 4-(3-chlorophenyl)-6-methyl-2-phenyl-1,4-dihydropyrimidine-5-carboxylic acid (3-phenyl-2-propene-1-yl)amide The title compound was obtained in the same manner as that of Example 60.

MS (ESI, m/z) 442 (M+H)+, 440 (M–H)–.

$^1$H-NMR (DMSO-d6): 2.19 (3H, s), 3.86–3.92 (2H, m), 5.70 (1H, s), 6.19–6.30 (2H, m), 7.42–7.38 (7H, m), 7.42–7.49 (3H, m), 7.84 (2H, d), 7.93 (1H, d), 9.01 (1H, s).

EXAMPLE 69

Synthesis of 4-(3-chlorophenyl)-6-methyl-2-pyridine-3-yl-1,4-dihydropyrimidine-5-carboxylic acid (3-phenyl-2-propene-1-yl)amide The title compound was obtained in the same manner as that of Example 60.

MS (ESI, m/z) 443 (M+H)+, 441 (M–H)–.

$^1$H-NMR (DMSO-d6): 2.48 (3H, s), 3.82–3.87 (2H, m), 5.73 (1H, s), 6.12–6.28 (2H, m), 7.21–7.40 (9H, m), 7.44–7.48 (1H, m), 7.94 (1H, s), 8.16 (1H, d), 8.65 (1H, d), 9.16 (1H, s), 9.20 (1H, s).

EXAMPLE 70

Synthesis of 4-(3,5-dichlorophenyl)-6-methyl-2-phenyl-1,4-dihydropyrimidine-5-carboxylic acid (3,3-diphenylpropyl)amide The title compound was obtained in the same manner as that of Example 60.

MS (ESI, m/z) 554 (M+H)+, 552 (M–H)–.

$^1$H-NMR (DMSO-d6): 2.10–2.13 (2H, m), 2.14 (3H, s), 2.95–3.00 (2H, m), 3.84 (1H, t), 5.65 (1H, s), 7.13–7.30 (12H, m), 7.43–7.50 (4H, m), 7.77 (1H, s), 7.83 (2H, d), 9.09 (1H, s).

EXAMPLE 71

Synthesis of 4-(3,5-dichlorophenyl)-6-methyl-2-pyridine-3-yl-1,4-dihydropyrimidine-5-carboxylic acid (3,3-diphenylpropyl)amide:

The title compound was obtained in the same manner as that of Example 60.

MS (ESI, m/z) 555 (M+H)+, 553 (M–H)–.

$^1$H-NMR (DMSO-d6): 2.12–2.47 (2H, m), 2.48 (3H, s), 2.90–2.97 (2H, m), 3.83 (1H, t), 5.68 (1H, s), 7.13–7.28 (12H, m), 7.44–7.48 (2H, m), 7.75 (1H, s), 8.15 (1H, d), 8.65 (1H, d), 8.98 (1H, s), 9.20 (1H, s).

EXAMPLE 72

Synthesis of 4-(3,5-dichlorophenyl)-2,6-dimethyl-1,4-dihydropyrimidine-5-carboxylic acid (3,3-diphenylpropyl)amide The title compound was obtained in the same manner as that of Example 60.

MS (ESI, m/z) 492 (M+H)+, 490 (M–H)–.

$^1$H-NMR (DMSO-d6): 2.06 (3H, s), 2.16–2.22 (2H, m), 2.50 (3H, s), 2.84–2.92 (2H, m), 3.74 (1H, t), 5.76 (1H, s), 7.12–7.25 (10H, m), 7.45 (2H, d), 7.57 (2H, d), 8.13 (1H, s).

EXAMPLE 73

Synthesis of 4-(3,5-dichlorophenyl)-6-methyl-2-phenyl-1,4-dihydropyrimidine-5-carboxylic acid (3-phenylpropyl)amide The title compound was obtained in the same manner as that of Example 60.

MS (ESI, m/z) 478 (M+H)+, 476 (M–H)–.

$^1$H-NMR (DMSO-d6): 1.61–1.66 (2H, m), 2.42–2.68 (2H, m), 2.71 (3H, s), 3.09–3.16 (2H, m), 5.63 (1H, s), 7.09–7.16 (4H, m), 7.22–7.27 (4H, m), 7.42–7.49 (4H, m), 7.77–7.84 (3H, m).

EXAMPLE 74

Synthesis of 4-(3,5-dichlorophenyl)-6-methyl-2-pyridine-3-yl-1,4-dihydropyrimidine-5-carboxylic acid (3-phenylpropyl)amide The title compound was obtained in the same manner as that of Example 60.

MS (ESI, m/z) 479 (M+H)+, 477 (M–H)–.

$^1$H-NMR (DMSO-d6): 1.60–1.70 (2H, m), 2.43–2.51 (2H, m), 2.52 (3H, s), 3.07–3.17 (2H, m), 5.68 (1H, s), 7.10–7.18 (3H, m), 7.23–7.29 (4H, m), 7.44–7.51 (2H, m), 7.80 (1H, s), 8.20 (1H, dd), 8.67 (1H, t), 9.01 (1H, d), 9.26 (1H, s).

EXAMPLE 75

Synthesis of 4-(3,4-dichlorophenyl)-6-methyl-2-phenyl-1,4-dihydropyrimidine-5-carboxylic acid (3-phenyl-2-propene-1-yl)amide The title compound was obtained in the same manner as that of Example 60.

MS (ESI, m/z) 476 (M+H)+, 474 (M−H)−.

¹H-NMR (DMSO-d6): 2.18 (3H, s), 3.84–3.89 (2H, m), 5.67 (1H, s), 6.09–6.18 (2H, m), 7.17–7.31 (6H, m), 7.40–7.49 (4H, m), 7.56 (1H, d), 7.81 (2H, d), 7.93 (1H, s), 9.04 (1H, s).

EXAMPLE 76

Synthesis of 4-(3,4-dichlorophenyl)-6-methyl-2-pyridine-3-yl-1,4-dihydropyrimidine-5-carboxylic acid (3-phenylpropene-1-yl)amide The title compound was obtained in the same manner as that of Example 60.

MS (ESI, m/z) 477 (M+H)+, 475 (M−H)−.

¹H-NMR (DMSO-d6): 2.19 (3H, s), 3.82–3.87 (2H, m), 5.67 (1H, s), 6.11–6.19 (1H, m), 6.26 (1H, d), 7.17–7.38 (7H, m), 7.41–7.51 (4H, m), 7.83 (2H, d), 8.00 (1H, s), 8.20 (1H, dt), 8.68 (1H, dd), 9.00 (1H, d), 9.25 (1H, s).

EXAMPLE 77

Synthesis of 4-(3,5-dichlorophenyl)-6-methyl-2-phenyl-1,4-dihydropyrimidine-5-carboxylic acid (3-phenyl-2-propene-1-yl)amide The title compound was obtained in the same manner as that of Example 60.

MS (ESI, m/z) 476 (M+H)+, 474 (M−H)−.

¹H-NMR (DMSO-d6): 2.18 (3H, s), 3.82–3.87 (2H, m), 5.67 (1H, s), 6.11–6.19 (1H, m), 6.26 (1H, d), 7.17–7.38 (7H, m), 7.41–7.51 (4H, m), 7.83 (2H, d), 8.00 (1H, s), 9.11 (1H, s).

EXAMPLE 78

Synthesis of 4-(3,5-dichlorophenyl)-6-methyl-2-pyridine-3-yl-1,4-dihydropyrimidine-5-carboxylic acid (3-phenyl-2-propene-1-yl)amide The title compound was obtained in the same manner as that of Example 60.

MS (ESI, m/z) 477 (M+H)+, 475 (M−H)−.

¹H-NMR (DMSO-d6): 2.17 (3H, s), 3.85–3.92 (2H, m), 5.70 (1H, s), 6.09–6.18 (1H, m), 6.25 (1H, d), 7.17–7.30 (7H, m), 7.45–7.49 (2H, m), 8.01 (1H, s), 8.17 (1H, dt), 8.66 (1H, dd), 8.98 (1H, d), 9.29 (1H, s).

EXAMPLE 79

Synthesis of 4-(3,4-dichlorophenyl)-6-methyl-2-methylsulfanyl-1,4-dihydropyrimidine-5-carboxylic acid (3-phenylpropyl)amide The title compound was obtained in the same manner as that of Example 58.

MS (ESI, m/z) 448 (M+H)+.

¹H-NMR (CDCl3): 1.75 (2H, t), 2.16 (3H, s), 2.40 (3H, s), 2.53 (2H, t), 3.15–3.32 (2H, m), 5.25 (1H, br), 5.43 (1H, s), 6.25 (1H, br), 7.08–7.10 (2H, m), 7.17–7.29 (6H, m).

EXAMPLE 80

Synthesis of 4-(3,4-dichlorophenyl)-6-methyl-2-methylsulfanyl-1,4-dihydropyrimidine-5-carboxylic acid (3,3-diphenylpropyl)amide The title compound was obtained in the same manner as that of Example 58.

MS (ESI, m/z) 524 (M+H)+.

¹H-NMR (CDCl3): 2.14 (5H, br), 2.37 (3H, s), 3.16 (2H, br d), 3.77 (1H, br), 5.19 (1H, br), 5.39 (1H, s), 6.31 (1H, br), 7.14–7.28 (12H, m), 7.37–7.39 (2H, m).

EXAMPLE 81

Synthesis of 4-(3,4-dichlorophenyl)-6-methyl-2-methylsulfanyl-1,4-dihydropyrimidine-5-carboxylic acid (3-phenyl-2-propene-1-yl)amide The title compound was obtained in the same manner as that of Example 58.

MS (ESI, m/z) 446 (M+H)+.

¹H-NMR (CDCl3): 2.23 (3H, s), 2.40 (3H, s), 3.92–4.10 (2H, m), 5.40 (1H, br), 5.50 (1H, s), 6.07 (1H, dt), 6.34 (2H, d), 7.20–7.43 (8H, m).

The structural formulae of the compounds obtained in Examples 1 to 81 are shown below.

TABLE 1

| Example | Structure |
|---|---|
| 1 | 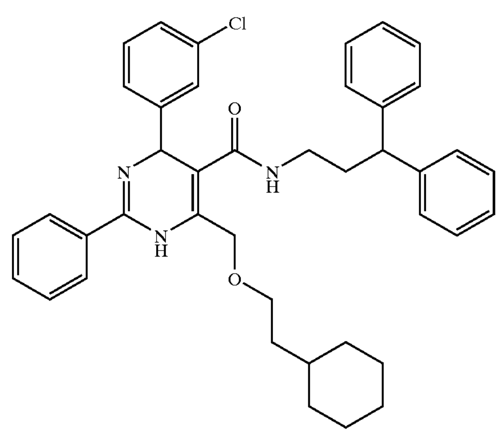 |

TABLE 1-continued
| Example | Structure |
|---|---|
| 2 | 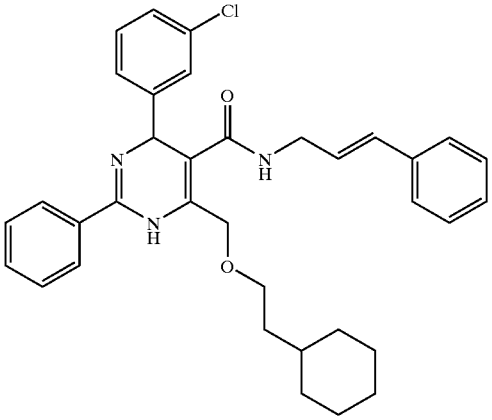 |
| 3 | 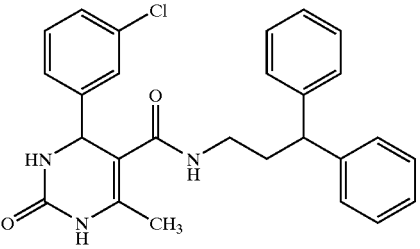 |
| 4 | 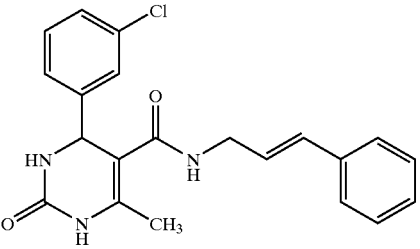 |
| 5 | 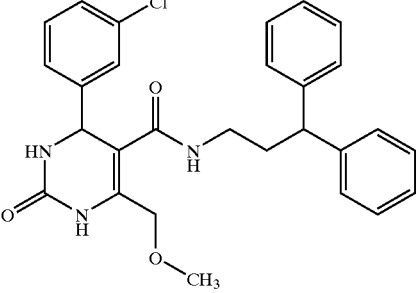 |
| 6 | 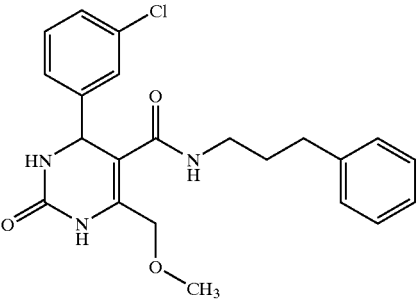 |

TABLE 1-continued
| Example | Structure |
|---|---|
| 7 | 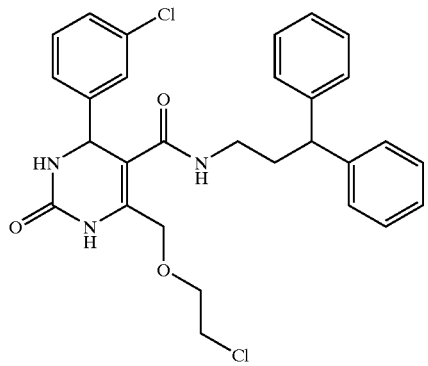 |
| 8 | 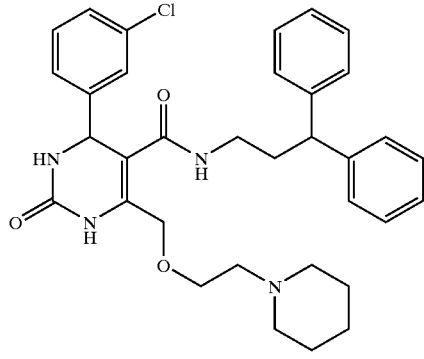 |
| 9 | 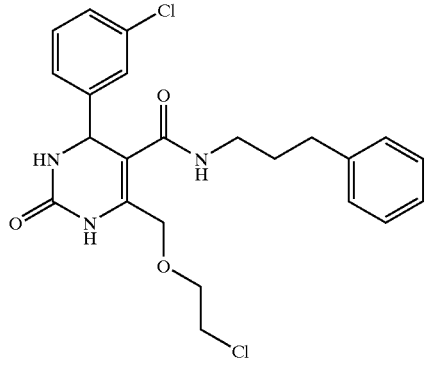 |
| 10 | 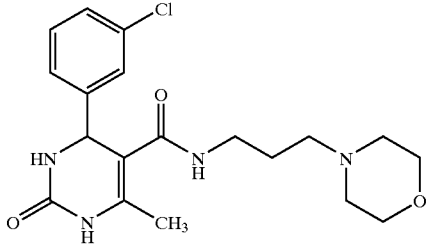 |

TABLE 1-continued
| Example | Structure |
|---|---|
| 11 | 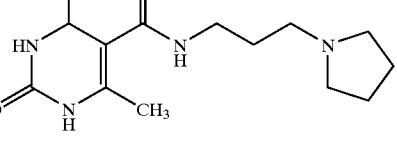 |
| 12 | 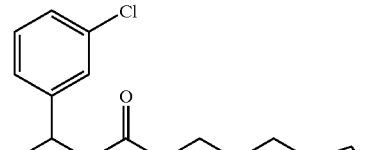 |
| 13 | 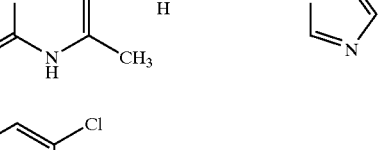 |
| 14 | 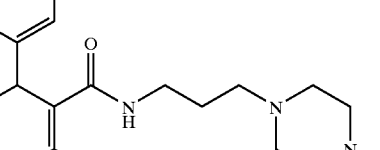 |
| 15 | 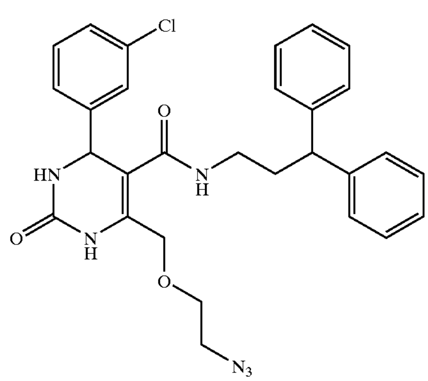 |

TABLE 1-continued

| Example | Structure |
|---|---|
| 16 | (structure) |
| 17 | (structure) |
| 18 | (structure) |
| 19 | (structure) |
| 20 | (structure) |

TABLE 1-continued

| Example | Structure |
|---|---|
| 21 | 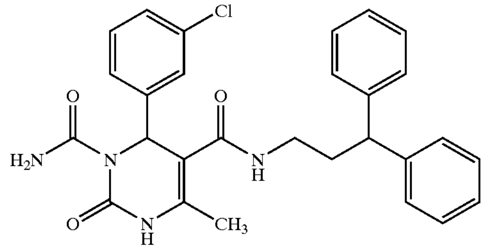 |
| 22 | 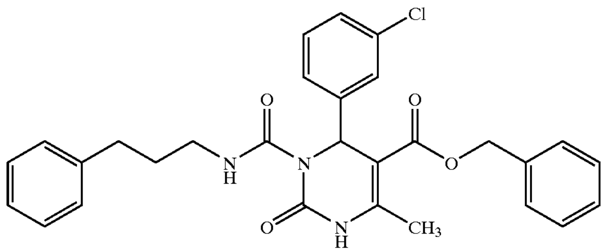 |
| 23 | 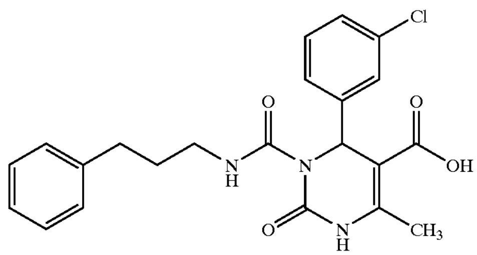 |
| 24 | 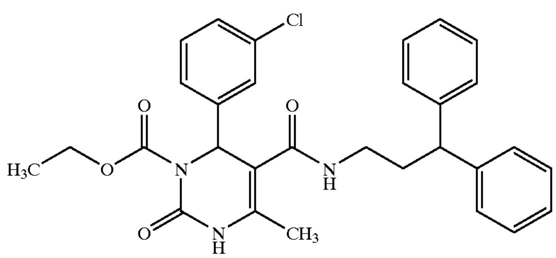 |
| 25 | 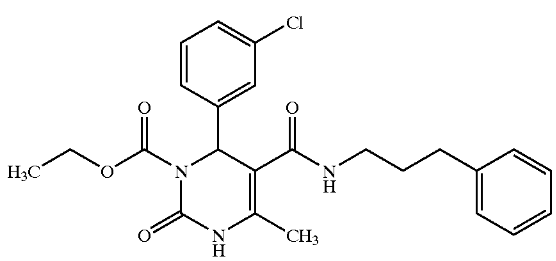 |
| 26 | 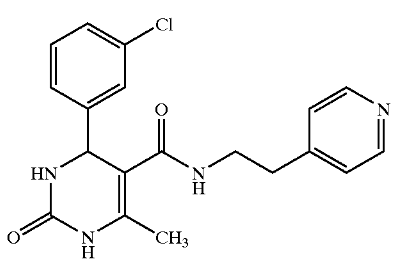 |

TABLE 1-continued

| Example | Structure |
|---|---|
| 27 | (structure) |
| 28 | (structure) |
| 29 | (structure) |
| 30 | (structure) |
| 31 | (structure) |
| 32 | (structure) |

TABLE 1-continued

| Example | Structure |
|---|---|
| 33 | 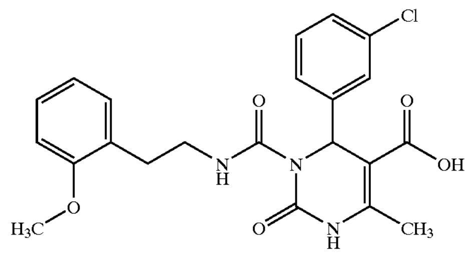 |
| 34 | 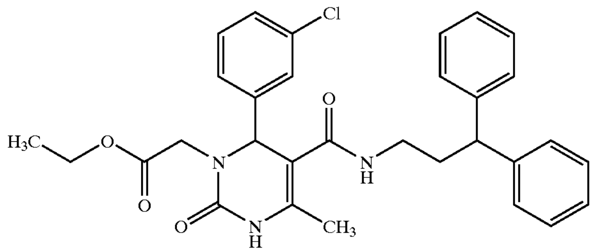 |
| 35 | 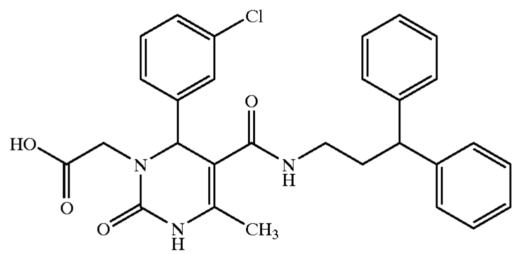 |
| 36 | 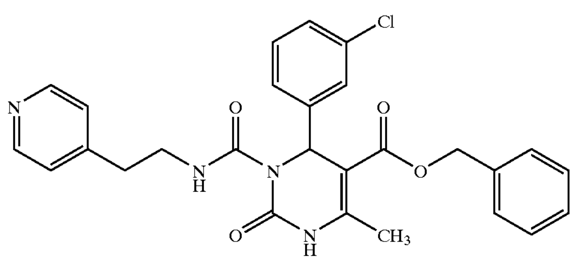 |
| 37 | 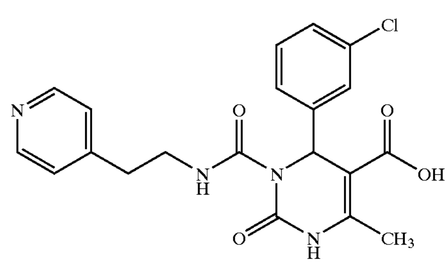 |
| 38 | 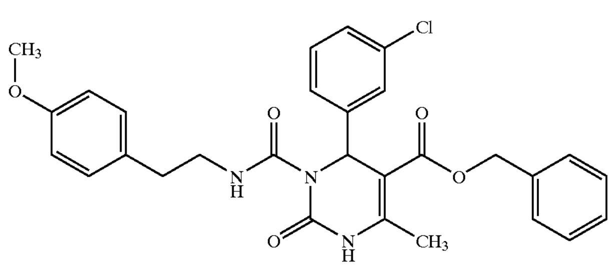 |

TABLE 1-continued

| Example | Structure |
|---------|-----------|
| 39 | 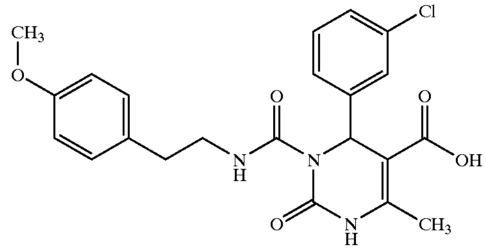 |
| 40 | 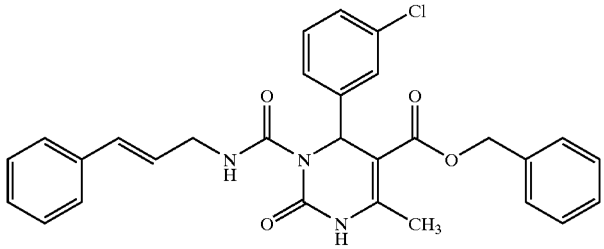 |
| 41 | 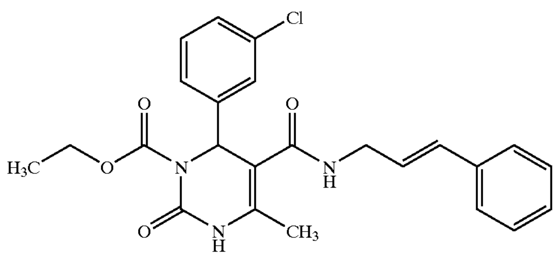 |
| 42 | 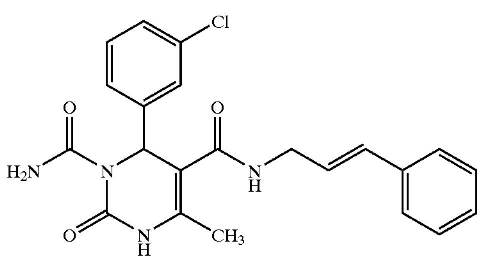 |
| 43 | 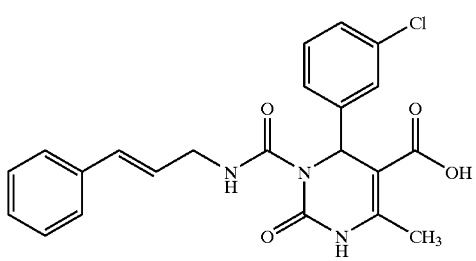 |
| 44 | 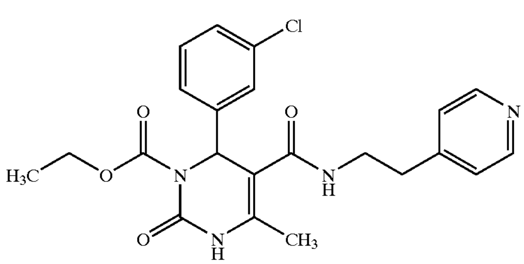 |

TABLE 1-continued

| Example | Structure |
|---------|-----------|
| 45 | 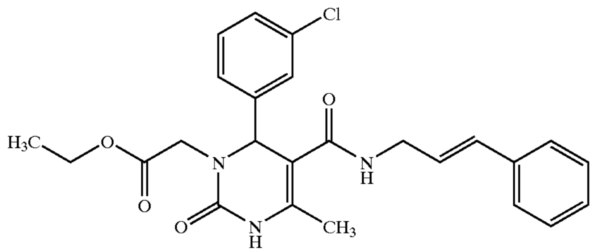 |
| 46 | 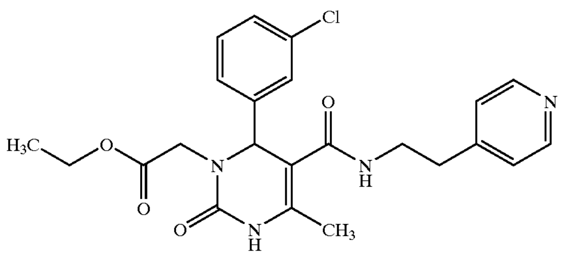 |
| 47 | 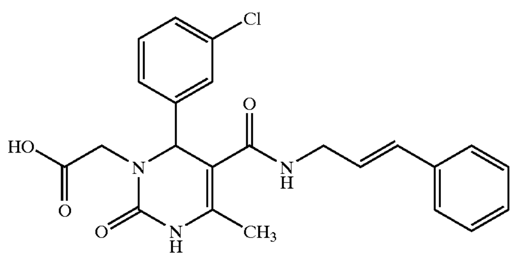 |
| 48 | 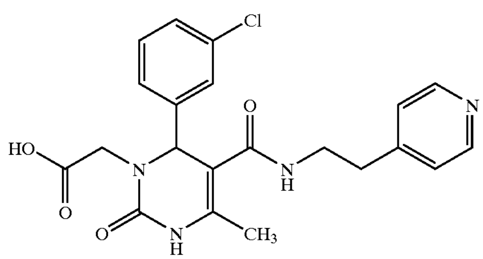 |
| 49 | 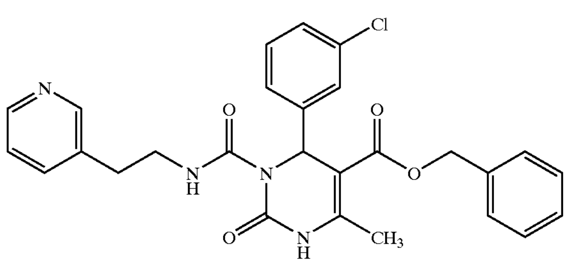 |
| 50 | 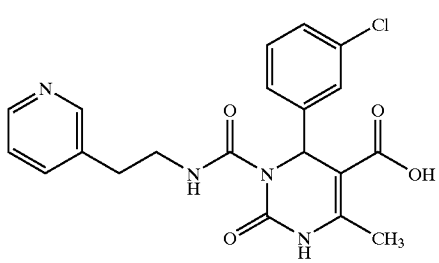 |

TABLE 1-continued
| Example | Structure |
|---|---|
| 51 | 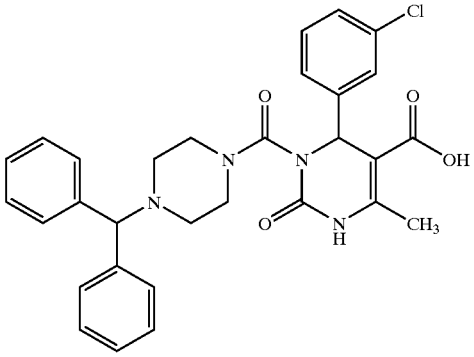 |
| 52 | 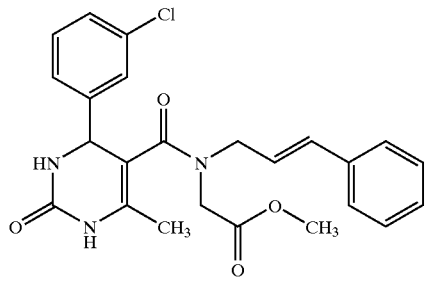 |
| 53 | 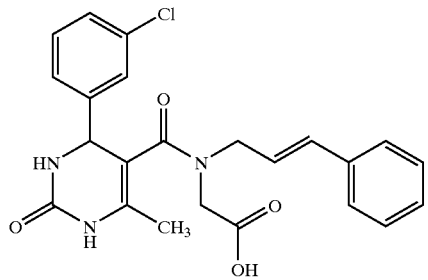 |
| 54 | 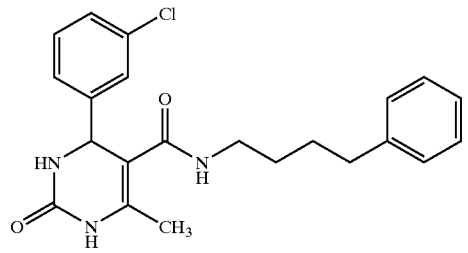 |
| 55 | 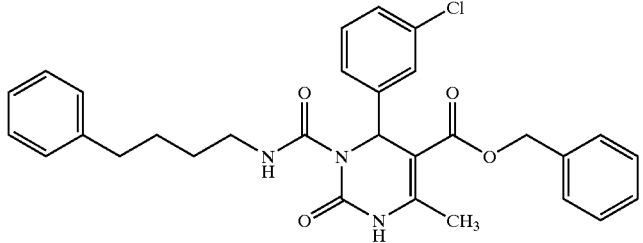 |

TABLE 1-continued

| Example | Structure |
|---------|-----------|
| 56 | (4-phenylbutyl)aminocarbonyl-substituted 4-(3-chlorophenyl)-6-methyl-2-oxo-1,2,3,4-tetrahydropyrimidine-5-carboxylic acid |
| 57 | 2-amino-4-(3-chlorophenyl)-6-methyl-N-(3,3-diphenylpropyl)-1,4-dihydropyrimidine-5-carboxamide |
| 58 | 4-(3-chlorophenyl)-6-methyl-2-(methylthio)-N-cinnamyl-1,4-dihydropyrimidine-5-carboxamide |
| 59 | 4-(3-chlorophenyl)-6-methyl-2-(methylthio)-N-(3,3-diphenylpropyl)-1,4-dihydropyrimidine-5-carboxamide |
| 60 | 4-(3,4-dichlorophenyl)-6-methyl-2-phenyl-N-(3-phenylpropyl)-1,4-dihydropyrimidine-5-carboxamide |

TABLE 1-continued

| Example | Structure |
|---|---|
| 61 | 4-(3,4-dichlorophenyl)-6-methyl-N-(3-phenylpropyl)-2-(pyridin-3-yl)-1,4-dihydropyrimidine-5-carboxamide |
| 62 | 4-(3,4-dichlorophenyl)-2,6-dimethyl-N-(3-phenylpropyl)-1,4-dihydropyrimidine-5-carboxamide |
| 63 | 4-(3,4-dichlorophenyl)-N-(3,3-diphenylpropyl)-6-methyl-2-phenyl-1,4-dihydropyrimidine-5-carboxamide |
| 64 | 4-(3,4-dichlorophenyl)-N-(3,3-diphenylpropyl)-6-methyl-2-(pyridin-3-yl)-1,4-dihydropyrimidine-5-carboxamide |

TABLE 1-continued

| Example | Structure |
|---|---|
| 65 | 4-(3,4-dichlorophenyl)-N-(3,3-diphenylpropyl)-2,6-dimethyl-1,4-dihydropyrimidine-5-carboxamide |
| 66 | 4-(3-chlorophenyl)-N-(3,3-diphenylpropyl)-6-methyl-2-(pyridin-3-yl)-1,4-dihydropyrimidine-5-carboxamide |
| 67 | 4-(3-chlorophenyl)-N-(3,3-diphenylpropyl)-6-methyl-2-phenyl-1,4-dihydropyrimidine-5-carboxamide |
| 68 | 4-(3-chlorophenyl)-N-cinnamyl-6-methyl-2-phenyl-1,4-dihydropyrimidine-5-carboxamide |
| 69 | 4-(3-chlorophenyl)-N-cinnamyl-6-methyl-2-(pyridin-3-yl)-1,4-dihydropyrimidine-5-carboxamide |

TABLE 1-continued
| Example | Structure |
|---|---|
| 70 | 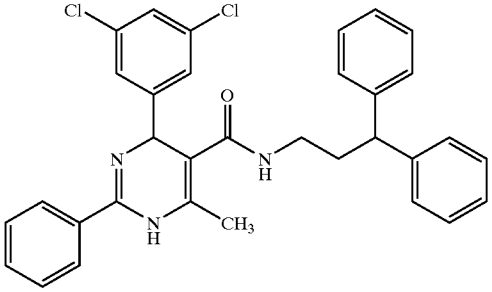 |
| 71 | 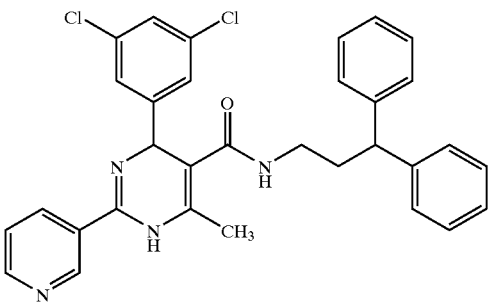 |
| 72 | 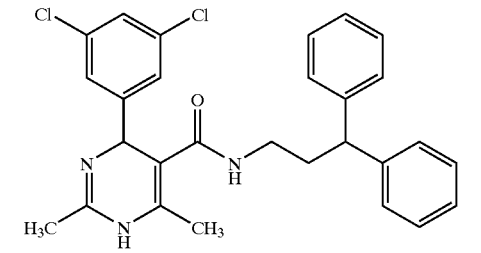 |
| 73 | 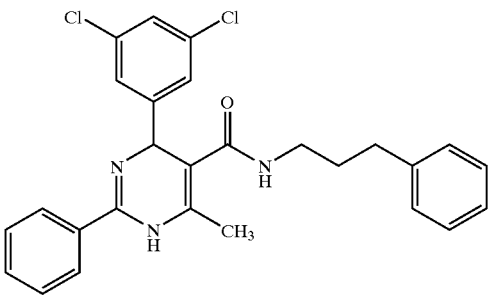 |
| 74 | 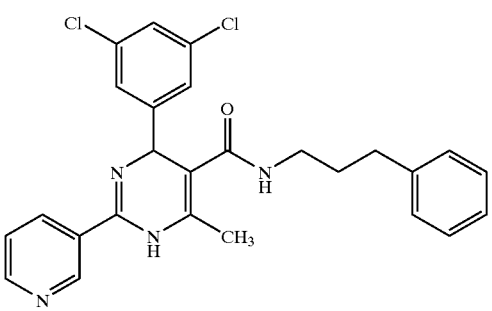 |

TABLE 1-continued

| Example | Structure |
|---|---|
| 75 | 4-(3,4-dichlorophenyl)-6-methyl-2-phenyl-N-cinnamyl-1,4-dihydropyrimidine-5-carboxamide |
| 76 | 4-(3,4-dichlorophenyl)-6-methyl-2-(pyridin-3-yl)-N-cinnamyl-1,4-dihydropyrimidine-5-carboxamide |
| 77 | 4-(3,5-dichlorophenyl)-6-methyl-2-phenyl-N-cinnamyl-1,4-dihydropyrimidine-5-carboxamide |
| 78 | 4-(3,5-dichlorophenyl)-6-methyl-2-(pyridin-3-yl)-N-cinnamyl-1,4-dihydropyrimidine-5-carboxamide |

TABLE 1-continued

| Example | Structure |
|---|---|
| 79 | 4-(3,4-dichlorophenyl)-2-(methylthio)-6-methyl-N-(3-phenylpropyl)-1,4-dihydropyrimidine-5-carboxamide |
| 80 | 4-(3,4-dichlorophenyl)-N-(3,3-diphenylpropyl)-2-(methylthio)-6-methyl-1,4-dihydropyrimidine-5-carboxamide |
| 81 | 4-(3,4-dichlorophenyl)-2-(methylthio)-6-methyl-N-cinnamyl-1,4-dihydropyrimidine-5-carboxamide |

TEST EXAMPLE

Antagonistic Activity on N-Type Calcium Channel
(Fluorescence Dye Method)

Human neuroblastoma cells IMR-32 were obtained from ATCC (American Type Culture Collection). The medium used was a Phenol Red-free Eagle minimum essential medium (GIBCO) containing earle's salts supplement, 2 mM of L-glutamine (GIBCO), 1 mM of sodium pyruvate (pH 6.5) (GIBCO), antibiotic/antimicotic mixture (GIBCO) and 10% fetal calf serum (Cell Culture Technologies). 3 ml of $1 \times 10^5$/ml IMR-32 cells were spread on a glass dish (Iwaki Glass Co., Ltd.) having a diameter of 35 mm which was treated with poly-D-lysin (SIGMA) and collagen (COLLAGEN VITROGEN 100, Collagen Co.). After the culture for 2 days, 1 mM (final concentration) of dibutyl cAMP and 2.5 µM of bromodeoxyuridine (SIGMA) were added. After the culture for additional 10 to 14 days, the cells were subjected to the activity determination. The medium for IMR-32 cells thus prepared was replaced with 1 ml of Phenol Red-free Eagle minimum essential medium (GIBCO) containing 1 ml of 10 µM fura-2/AM (Dojin Kagaku, Co.) and earle's salts supplement, and the incubation was conducted at 25° C. for 1 hour.

Then the medium was replaced with Phenol Red-free Eagle minimum essential medium (GIBCO) containing earle's salts supplement, from which fura-2/AM had been removed. After the incubation at 37° C. for 1 hour, the medium was replaced with a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose). Antagonistic activity on N-type calcium channel was determined and analyzed by using a fluorescence microscope (Nikon Corporation) and an image analysis device ARGUS 50 (Hamamatsu Photonics). In particular, a recording medium (20 mM of HEPES-KOH, 115 mM of NaCl, 5.4 mM of KCl, 0.8 mM of $MgCl_2$, 1.8 mM of $CaCl_2$ and 13.8 mM of D-glucose) containing 1 µM of Nifedipine was given to the cells by reflux by a Y-tube method. Then a stimulating agent containing 60 mM of potassium chloride was rapidly given by the Y-tube method. Stimulating agents containing 60 mM of potassium chloride and 0.1, 1 or 10 µM of test compound were successively rapidly given by the Y-tube method to determine the antagonistic activity on the channel. Finally, a stimulating agent containing 60 mM of potassium chloride and 1 µM of omega conotoxin GVIA (Peptide institute, Inc.) was rapidly given by the Y-tube method to realize a condition of 100% inhibition of N-type calcium channel.

TEST EXAMPLE

Antagonistic Activity on L-Type Calcium Channel

The activity of the dihydropyrimidine derivatives of the present invention to inhibit L-type calcium channel was determined by the following method in which the relaxation reaction on the KCl contraction of samples of thoracic aorta extracted from rats was employed.

1) Method of Preparation of Samples of Thoracic Aorta Extracted from Rats:

The slips of thoracic aorta extracted from a Wistar rat was used. The blood vessels were cut to obtain ring-shaped samples having a width of about 3 mm. The endothelial cells of the blood vessel were mechanically removed. The samples were suspended in a strain gage in Tyrode's solution (158.3 mM of NaCl, 4.0 mM of KCl, 1.05 mM of $MgCl_2$, 0.42 mM of $NaH_2PO_4$, 10 mM of $NaHCO_3$, 2 mM of $CaCl_2$ and 5 mM of glucose) in which a gaseous mixture of $O_2$ (95%) and $CO_2$ (5%) was introduced. A static tension of 2 g was applied hereto. The tension of the blood vessel was amplified with transducer and a tension amplifier (EF-601G; Nihon Koden Corporation) and recorded with a multi-pen recorder (Rikadenki Kogyo Co., Ltd.). The experiments were conducted at 37° C.

2) Determination of Relaxation After KCl Contraction:

After the tension had been stabilized, the nutrient solution in the sample tank was replaced with High $K^+$ Tyrode's solution (112.3 mM of NaCl, 50 mM of KCl, 1.05 mM of $MgCl_2$, 0.42 mM of $NaH_2PO_4$, 10 mM of $NaHCO_3$, 2 mM of $CaCl_2$ and 5 mM of glucose) to conduct the contraction reaction. 30 minutes after, the solution in the sample tank was replaced with the normal Tyrode's solution. The solution in the sample tank was again replaced with the High $K^+$ Tyrode's solution and the contraction reaction was observed. After attaining the maximum contraction reaction, the test compound was cumulatively added at intervals of 90 minutes to attain concentrations of $10^{-9}$, $10^{-8}$, $10^{-7}$ and $10^{-6}$ M. The rate of the test compound to control the maximum contraction reaction was employed as the index of the inhibition activity on L-type calcium channel.

Table 3 shows the results of the determination of the activity of inhibiting the N-type calcium channel (pIC50) and L-type calcium channel (IC50). pIC50 indicates the antagonistic activity of the test compound. It is a negative logarithm of a concentration of a medicine necessitated for 50% inhibition.

TABLE 2

| Example | N-type inhibition pIC50 | L-type inhibition IC50 |
| --- | --- | --- |
| 1 | 5.90 | 4.75 |
| 2 | 5.23 | 4.03 |
| 3 | 6.05 | 4.93 |
| 6 | 6.01 | 5.06 |

The same procedure as that of the above-described tests of the N-type calcium channel antagonistic activity of the compounds obtained in the Examples was repeated except for the following changes: 60 mM of potassium chloride-containing stimulating agent was rapidly given by the Y-tube method while the calcium concentration change in the cells was examined in terms of N-type calcium channel activity. Then Stimulating agents containing 60 mM of potassium chloride and 0.1, 1 or 10 μM of test compound were successively and rapidly given by the Y-tube method. A change in calcium concentration in the cells was determined. N-type calcium channel antagonistic activities calculated from the inhibition rates are shown in Table 3.

TABLE 3

| Example | N-type inhibition pIC50 | L-type inhibition IC50 |
| --- | --- | --- |
| 1 | 5.1 | 4.8 |
| 3 | 5.6 | 5.2 |
| 6 | 5.3 | 5.1 |
| 15 | 5.6 | 5.6 |
| 45 | 5.4 | 5.3 |
| 64 | 5.9 | 5.7 |
| 67 | 5.8 | 5.7 |
| 68 | 5.9 | 5.5 |
| 75 | 5.7 | 5.4 |

Thus it is apparent that the new dihydropyrimidine derivatives have excellent N-type calcium channel antagonistic activity and that they were highly selective to L-type calcium channels.

The new dihydropyrimidine derivatives of the present invention had selective N-type calcium channel antagonistic activity. Thus, the new dihydropyrimidine derivatives of the present invention are effective in the treatment of acute stage of ischemic cerebrovascular disorders caused by cerebral infarction or intracerebral bleeding (including subarachnoidal hemorrhage); progressive neurodegenerative diseases such as Alzheimer's disease, AIDS related dementia, Parkinson's disease, dementia due to cerebrovascular disorder and ALS; cerebral disorders caused by head injury; pains and cold flush caused by diabetes or thromboangiitis obliterans; various pains such as postoperative pain, migraine and visceral pain; various diseases associated with psychogenic stress such as bronchial asthma, unstable angina and irritable colitis; emotional disorder and withdrawal symptoms after addiction to drugs such as ethanol withdrawal symptoms.

What is claimed is:

1. A dihydropyrimidine compound of the following formula (I), a tautomer thereof or a pharmaceutically acceptable salt thereof:

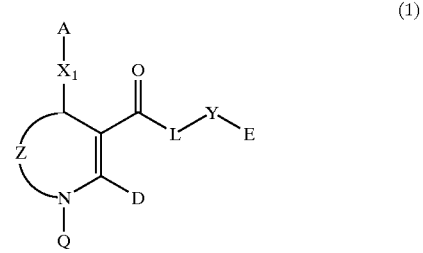

(1)

wherein

Z represents a group of the following formula (Z1), which is bonded to the nitrogen atom at the symbol "*":

(Z1)

wherein $B_1$ represents a hydrogen atom, a carboxy-lower alkyl group, a lower alkyloxycarbonyl-lower alkyl group or a group of the following general formula (3) or (4):

(3)

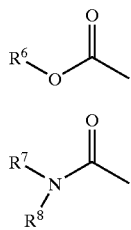

(4)

wherein $R^6$ to $R^8$ each represent a hydrogen atom or a linear, branched or cyclic, saturated or unsaturated hydrocarbon group having 1 to 6 carbon atoms, $X_2$ represents an oxygen atom or sulfur atom, A represents a group of the following formula (2), or a substituted or unsubstituted 1-naphthyl, 2-naphthyl, indole-2-yl, indole-3-yl, thiophene-3-yl, thiophene-2-yl, furan-3-yl, furan-2-yl, pyridine-4-yl, pyridine-3-yl or pyridine-2-yl group wherein the substituents in these groups are those described later with reference $R^1$ to $R^5$ in the formula (2):

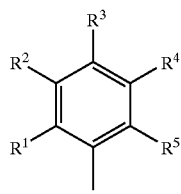

(2)

wherein $R^1$, $R^2$, $R^3$, $R^4$ and $R^5$ may be the same or different from each other and each represent a hydrogen atom, a halogen atom, hydroxyl group, carboxyl group, amino group, cyano group, nitro group, a lower alkyl group, a lower alkoxyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, an amino-lower alkyl group, an amino-lower alkoxyl group, an amino-lower alkenyl group, a carboxy-lower alkyl group, a carboxy-lower alkoxyl group, a carboxy-lower alkenyl group, a benzyloxy group, a benzoyl or a pyridylcarbonyl group, Q represents a hydrogen atom or a lower alkyl group, D represents a hydrogen atom, a lower alkyl group, dimethoxymethyl group, cyano group, a benzyl group, a pyridylmethyl group, a hydroxy-lower alkyl group, a halogeno-lower alkyl group, an amino-lower alkyl group, a carboxy-lower alkyl group or a group of the following formula (5) or (6):

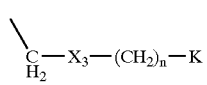

(5)

-continued

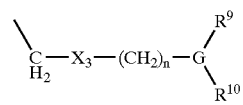

(6)

wherein $X_3$ represents O, S or N—$R^{8'}$, n represents an integer of 0 to 6

K in the formula (5) represents a hydrogen atom, a halogen atom, hydroxyl group, carboxyl group, amino group, cyano group, nitro group, azido group, a substituted or unsubstituted phenyl group or a substituted or unsubstituted heteroaryl group, wherein said heteroaryl group is selected from the group consisting of a pyridyl group, a furyl group and a thienyl group and wherein the substituents in these groups are those described with reference $R^1$ to $R^5$ in the formula (2), G in the formula (6) represents N or C—H, wherein $R^{8'}$ to $R^{10}$ may be the sauce or different from each other, and they each represent hydrogen atom, a linear, branched or cyclic, saturated or unsaturated hydrocarbon group having 1 to 6 carbon atoms, a substituted or unsubstituted phenyl group, a substituted or unsubstituted heteroaryl group wherein said heteroaryl group is selected from the group consisting of a pyridyl group, a furyl group and a thienyl group, a hydroxy-lower alkyl group, a hydroxy-lower alkenyl group, a halogeno-lower alkyl group, a halogeno-lower alkenyl group, an amino-lower alkyl group, an amino-lower alkenyl group, a carboxy-lower alkyl group, a carboxy-lower alkenyl group, a benzyl group, a pyridylmethyl group, cyano-lower alkyl group or a cyano-lower alkenyl group, and the chains may contain a hetero atom wherein the substituents in the substituted phenyl, pyridyl, furyl and thienyl groups of $R^{8'}$ are halogen atoms, alkyl groups and alkoxy groups and the substituents in the substituted phenyl, pyridyl, furyl and thienyl groups of $R^9$ and $R^{10}$ are those described with reference $R^1$ to $R^5$ in the formula (2), or $R^9$ and $R^{10}$ may together form a ring selected from the group consisting of a cyclopentyl group, a cyclohexyl group, a piperidino-1-yl group, a piperidine-4-yl group, a pyrrolidine-1-yl group, a pyrrolidine-8-yl group, a piperidinone-1-yl group, a pyrrolidinone-1-yl group, a piperazine-1-yl group and a morpholine-4-yl group, E represents a group of the following general formula (7) or a substituted or unsubstituted heteroaryl group, wherein said heteroaryl group is selected from the group consisting of thiophen-3-yl, thiophen-2-yl, furan-3-yl, furan-2-yl, pyridine-4-yl, pyridine-3-yl, pyridine-2-yl and imidazol-1-yl wherein the substitute is selected from the group consisting of halogens, lower alkyl groups and alkoxyl groups:

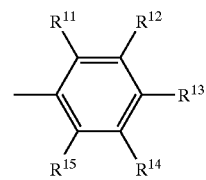

(7)

wherein $R^{11}$, $R^{12}$, $R^{13}$, $R^{14}$ and $R^{15}$ may be the same or different from each other and each represent a hydrogen atom, a halogen atom, hydroxyl group, carboxyl group, amino group, cyano group, nitro group, a lower alkyl group, a lower alkoxyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, an amino-lower alkyl group, an amino-lower alkoxyl group, an amino-lower alkenyl group, a carboxy-lower alkyl group, a carboxy-lower alkoxyl group, a carboxy-lower alkenyl group, benzyl group, benzyloxy group, a lower alkoxycarbonyl group, benzoyl, pyridylcarbonyl group, a substituted or unsubstituted phenyl group, a substituted or unsubstituted heteroaryl group wherein said heteroaryl group is selected from the group consisting of a pyridyl group, a furyl group and a thienyl group, or cyclopentyl group, cyclohexyl group, piperidyl group, pyrrolidinyl group and piperazinyl group wherein the substituents in the substituted phenyl, pyridyl, furyl and thienyl groups are halogen atoms, alkyl groups and alkoxyl groups, $X_1$ represents an interatomic bond L represents >N-J wherein J represents a hydrogen atom, a lower alkyl group, a carboxy-lower alkyl group or a lower alkyloxycarbonyl-lower alkyl group, Y represents a saturated or unsaturated linear hydrocarbon group having 1 to 6 carbon atoms, which may contain a hetero atom in the group thereof, or a group of the following general formula (8):

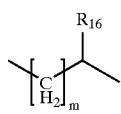

(8)

wherein $R^{16}$ represents a substituted or unsubstituted phenyl group, a substituted or unsubstituted heteroaryl group, wherein said heteroaryl group is selected from the group consisting of pyridyl, furyl and thienyl groups wherein the substituent is selected from the group consisting of halogens, lower alkyl groups and alkoxyl groups, and m represents an integer of 0 to 5.

2. The dihydropyrimidine compound, tautomer thereof or pharmaceutically acceptable salt thereof according to claim 1, wherein $B_1$ represents a hydrogen atom.

3. The dihydropyrimidine compound, tautomer thereof or pharmaceutically acceptable salt thereof according to claim 1, wherein $B_1$ represents a group of general formula (3).

4. The dihydropyrimidine compound, tautomer thereof or pharmaceutically acceptable salt thereof according to claim 1, wherein $B_1$ represents a group of general formula (4).

5. The dihydropyrimidine compound, tautomer thereof or pharmaceutically acceptable salt thereof according to claim 1, wherein represents a carboxy-lower alkyl group or a lower alkyloxycarbonyl-lower alkyl group.

6. A dihydropyrimidine compound of the following formula (1), a tautomer thereof or a pharmaceutically acceptable salt thereof:

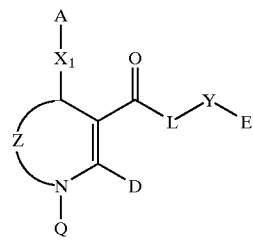

(1)

wherein

Z represents a group of the following formula (Z1), which is bonded to the nitrogen atom at the symbol "*":

(Z1)

wherein $B_1$ represents a hydrogen atom, a carboxy-lower alkyl group, a lower alkyloxycarbonyl-lower alkyl group or a group of the following general formula (4):

(4)

wherein $R^7$ represents a hydrogen atom, a linear, branched or cyclic, saturated or unsaturated hydrocarbon group having 1 to 6 carbon atoms, and $R^8$ a benzyl group, 3-phenylpxopyl group, 3-phenyl-2-propene-1-yl group, 3,3-diphenylpropyl group, 3-(pyridine-2-yl)propyl group, 3-(pyridine-2-yl)-2-propene-1-yl group, 2-(2-methoxyphenyl)ethyl group, 2-(4-methoxyphenyl)ethyl group, 2-(4-hydroxyphenyl)ethyl group, 2-phenoxyethyl group, 2-(pyridine-4-yl) ethyl group or 4-phenyl butyl group, $X_2$ represents an oxygen atom or sulfur atom, A represents a group of the following formula (2), or a substituted or unsubstituted 1-naphthyl, 2-naphthyl, indole-2-yl indole-3-yl, thiophene-3-yl, thiophene-2-yl, furan-3-yl, furan-2-yl, pyridine-4-yl, pyridine-3-yl or pyridine-2-yl group wherein the substituents in these groups are those described below with reference $R^1$ to $R^5$ in the formula (2):

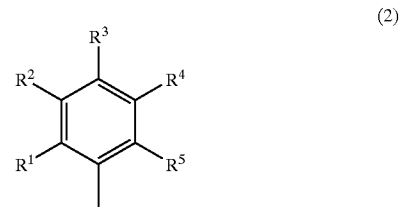

(2)

wherein $R^1$, $R^2$, $R^3$, $R^4$ and $R^5$ may be the same or different from each other and each represent a hydrogen atom, a halogen atom, hydroxyl group, carboxyl group, amino group, cyano group, nitro group, a lower alkyl group, a lower alkoxyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, an amino-lower alkyl group, an amino-lower alkoxyl group, an amino-lower alkenyl group, a carboxy-lower alkyl group, a carboxy-lower alkoxyl group, a carboxy-lower alkenyl group, a benzyloxy group, a benzoyl or a pyridylcarbonyl group, Q represents a hydrogen atom or a lower alkyl group, D represents a hydrogen atom, a lower alkyl group, dimethoxymethyl group, cyano group, a benzyl group, a pyridylmethyl group, a hydroxy-lower alkyl group, a halogeno-lower alkyl group, an amino-lower alkyl group, a carboxy-lower alkyl group or a group of the following formula (5) or (6):

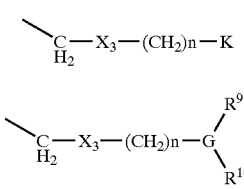

wherein $X_3$ represents O, S or N—$R^{8'}$, n represents an integer of 0 to 6,

K in the formula (5) represents a hydrogen atom, a halogen atom, hydroxyl group, carboxyl group, amino group, cyano group, nitro group, azido group, a substituted or unsubstituted phenyl group or a substituted or unsubstituted heteroaryl group, wherein said heteroaryl group is selected from the group consisting of a pyridyl group, a furyl group and a thienyl group and wherein the substituents in these groups are those described with reference to $R^1$ to $R^5$ in the formula (2), G in the formula (6) represents N or C—H, wherein $R^{8'}$ to $R^{10}$ may be the same or different from each other, and they each represent hydrogen atom, a linear, branched or cyclic, saturated or unsaturated hydrocarbon group having 1 to 6 carbon atoms, a substituted or unsubstituted phenyl group, a substituted or unsubstituted heteroaryl group wherein said heteroaryl group is selected from the group consisting of a pyridyl group, a furyl group and a thienyl group, a hydroxy-lower alkyl group, a hydroxy-lower alkenyl group, a halogeno-lower alkyl group, a halogeno-lower alkenyl group, an amino-lower alkyl group, an amino-lower alkenyl group, a carboxy-lower alkyl group, a carboxy-lower alkenyl group, a benzyl group, a pyridylmethyl group, cyano-lower alkyl group or a cyano-lower alkenyl group, and the chains may contain a hetero atom wherein the substituents in the substituted phenyl, pyridyl, furyl and thienyl groups of $R^{8'}$ are halogen atoms, alkyl groups and alkoxy groups and the substituents in the substituted phenyl, pyridyl, furyl and thienyl groups of $R^9$ and $R^{10}$ are those described with reference $R^1$ to $R^5$ in the formula (2), or $R^9$ and $R^{10}$ may together form a ring selected from the group consisting of a cyclopentyl group, a cyclohexyl group, a piperidine-1-yl group, a piperidine-4-yl group, a pyrrolidine-1-yl group, a pyrrolidine-8-yl group, a piperidinone-1-yl group, a pyrrolidinone-1-yl group, a piperazine-1-yl group and a morpholine-4-yl group, E represents a hydrogen atom, $X_1$ represents an interatomic bond, L represents oxygen atom, and Y represents an interatomic bond.

7. A dihydropyrimidine compound of the following formula (1), a tautomer thereof or a pharmaceutically acceptable salt thereof:

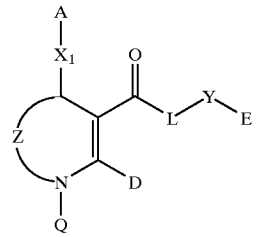

wherein

Z represents a group of the following formula (Z2), which is bonded to the nitrogen atom at the symbol "*":

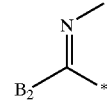

wherein $B_2$ represents an amino group, a lower alkyl group, a lower alkylamino group, a lower alkylthio group, benzyl group, a pyridylmethyl group, a hydroxy-lower alkyl group, a halogeno-lower alkyl group, unsubstituted heteroaryl group, wherein said heteroaryl group is selected from the group consisting of a pyridyl group, a furyl group and a thienyl group, and wherein the substituents in the substituted phenyl, pyridyl, furyl and thienyl groups are halogen atoms, hydroxyl group, carboxyl group, amino group, cyano group, nitro group, lower alkyl groups, lower alkoxyl groups, halogeno-lower alkyl groups, hydroxyl-lower alkyl groups and lower-alkoxycarbonyl groups, $X_2$ represents an oxygen atom or sulfur atom, A represents a group of the following formula (2), or a substituted or unsubstituted 1-naphthyl, 2-naphthyl, indole-2-yl, indole-3-yl, thiophene-3-yl, thiophene-2-yl, furan-3-yl, furan-2-yl, pyridine-4-yl, pyridine-3-yl or pyridine-2-yl group wherein the substituents in these groups are those described below with reference $R^1$ to $R^5$ in the formula (2):

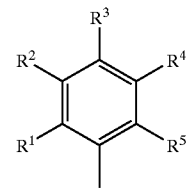

wherein $R^1$, $R^2$, $R^3$, $R^4$ and $R^5$ may be the same or different from each other and each represent a hydrogen atom, a halogen atom, hydroxyl group, carboxyl group, amino group, cyano group, nitro group, a lower alkyl group, a lower alkoxyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, an amino-lower alkyl group, an amino-lower alkoxyl group, an amino-lower alkenyl group, a carboxy-lower alkyl group, a carboxy-lower alkoxyl group, a carboxy-lower alkenyl group, a benzyloxy group, a benzoyl or a pyridylcarbonyl group, Q represents a hydrogen atom or a lower alkyl group, D represents a hydrogen atom, a lower alkyl group, dimethoxymethyl group, cyano group, a benzyl group, a pyridylmethyl group, a hydroxy-lower alkyl group, a halogeno-lower alkyl group, an amino-lower alkyl group, a carboxy-lower alkyl group or a group of the following formula (5) or (6):

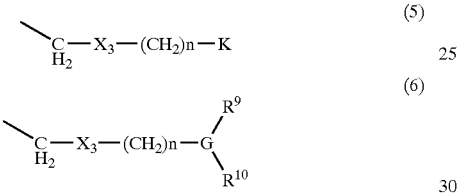

wherein $X_3$ represents O, S or N—$R^{8'}$, n represents an integer of 0 to 6,

K in the formula (5) represents a hydrogen atom, a halogen atom, hydroxyl group, carboxyl group, amino group, cyano group, nitro group, azido group, a substituted or unsubstituted phenyl group or a substituted or unsubstituted heteroaryl group, wherein said heteroaryl group is selected from the group consisting of a pyridyl group, a furyl group and a thienyl group and wherein the substituents in these groups are those described with reference to $R^1$ to $R^5$ in the formula (2), G in the formula (6) represents N or C—H, wherein $R^{8'}$ to $R^{10}$ may be the same or different from each other, and they each represent hydrogen atom, a linear, branched or cyclic, saturated or unsaturated hydrocarbon group having 1 to 6 carbon atoms, a substituted or unsubstituted phenyl group, a substituted or unsubstituted heteroaryl group wherein said heteroaryl group is selected from the group consisting of a pyridyl group, a furyl group and a thienyl group, a hydroxy-lower alkyl group, a hydroxy-lower alkenyl group, a halogeno-lower alkyl group, a halogeno-lower alkenyl group, an amino-lower alkyl group, an amino-lower alkenyl group, a carboxy-lower alkyl group, a carboxy-lower alkenyl group, a benzyl group, a pyridylmethyl group, cyano-lower alkyl group or a cyano-lower alkenyl group, and the chains may contain a hetero atom wherein the substituents in the substituted phenyl, pyridyl, furyl and thienyl groups of $R^{8'}$ are halogen atoms, alkyl groups and alkoxy groups and the substituents in the substituted phenyl, pyridyl, furyl and thienyl groups of $R^9$ and $R^{10}$ are those described with reference $R^1$ to $R^5$ in the formula (2), or $R^9$ and $R^{10}$ may together form a ring selected from the group consisting of a cyclopentyl group, a cyclohexyl group, a piperidine-1-yl group, a piperidine-4-yl group, a pyrrolidine-1-yl group, a pyrrolidine-3-yl group, a piperidinone-1-yl group, a pyrrolidinone-1-yl group, a piperazine-1-yl group and a morpholine-4-yl group, E represents a group of the following general formula (7) or a substituted or unsubstituted heteroaryl group, wherein said heteroaryl group is selected from the group consisting of thiophen-3-yl, thiophen-2-yl, furan-3-yl, furan-2-yl, pyridine-4-yl, pyridine-3-yl, pyridine-2-yl and imidazol-1-yl wherein the substituent is selected from the group consisting of halogens, lower alkyl groups and alkoxyl groups:

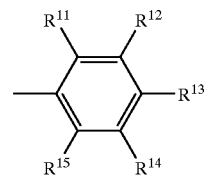

wherein $R^{11}$, $R^{12}$, $R^{13}$, $R^{14}$ and $R^{15}$ may be the same or different from each other and each represent a hydrogen atom, a halogen atom, hydroxyl group, carboxyl group, amino group, cyano group, nitro group, a lower alkyl group, a lower alkoxyl group, a lower alkylamino group, a lower alkylthio group, a lower alkanoyl group, a hydroxy lower alkyl group, a hydroxy-lower alkoxyl group, a hydroxy-lower alkenyl group, a halogeno-lower alkyl group, a halogeno-lower alkoxyl group, an amino-lower alkyl group, an amino-lower alkoxyl group, an amino-lower alkenyl group, a carboxy lower alkyl group, a carboxy-lower alkoxyl group, a carboxy-lower alkenyl group, benzyl group, benzyloxy group, a lower alkoxycarbonyl group, benzoyl, pyridylcarbonyl group, a substituted or unsubstituted phenyl group, a substituted or unsubstituted heteroaryl group wherein said heteroaryl group is selected from the group consisting of a pyridyl group, a furyl group and a thienyl group, or cyclopentyl group, cyclohexyl group, piperidyl group, pyrrolidinyl group and piperazinyl group wherein the substituents in the substituted phenyl, pyridyl, furyl and thienyl groups are halogen atoms, alkyl groups and alkoxyl groups, $X_1$ represents an interatomic bond L represents >N-J wherein J represents a hydrogen atom, a lower alkyl group, a carboxy-lower alkyl group or a lower alkyloxycarbonyl-lower alkyl group, Y represents a saturated or unsaturated linear hydrocarbon group having 1 to 6 carbon atoms, which may contain a hetero atom in the group thereof, or a group of the following general formula (8):

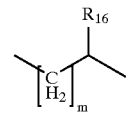

wherein $R_{16}$ represents a substituted or unsubstituted phenyl group, a substituted or unsubstituted heteroaryl group, wherein said heteroaryl group is selected from the group consisting of pyridyl, furyl and thienyl groups wherein the substituent is selected from the group consisting of halogens, lower alkyl groups and alkoxyl groups, and m represents an integer of 0 to 5.

8. The dihydropyrimidine compound, tautomer thereof or pharmaceutically acceptable salt thereof according to claim 7, wherein $B_2$ is selected from the group consisting of substituted or unsubstituted phenyl groups, a substituted or unsubstituted furyl groups and substituted or unsubstituted thienyl groups.

9. The dihydropyrimidine compound, tautomer thereof or pharmaceutically acceptable salt thereof according to claim 7, wherein $B_2$ represents an amino group, or a lower alkylamino group.

10. The dihydropyrimidine compound, tautomer thereof or pharmaceutically acceptable salt thereof according to claim 7, wherein $B_2$ represents a lower alkylthio group.

11. The dihydropyrimidine compound, tautomer thereof or pharmaceutically acceptable salt thereof according to claim 7, wherein $B_2$ represents a lower alkyl group.

12. A pharmaceutical composition comprising a dihydropyrimidine compound, tautomer thereof and pharmaceutically acceptable salt thereof according to claim 1 and one or more adjuvants.

13. A pharmaceutical composition comprising a dihydropyrimidine compound, tautomer thereof and pharmaceutically acceptable salt thereof according to claim 6 and one or more adjuvants.

14. A pharmaceutical composition comprising a dihydropyrimidine compound, tautomer thereof and pharmaceutically acceptable salt thereof according to claim 7 and one or more adjuvants.

15. A method of antagonizing N-type calcium channels, comprising contacting N-type calcium channels with an effective amount of the compound of claim 1.

16. A method of antagonizing N-type calcium channels, comprising contacting N-type calcium channels with an effective amount of the compound of claim 6.

17. A method of antagonizing N-type calcium channels, comprising contacting N-type calcium channels with an effective amount of the compound of claim 7.

* * * * *